(12) United States Patent
Sano et al.

(10) Patent No.: US 12,116,370 B2
(45) Date of Patent: Oct. 15, 2024

(54) CONDENSED HETEROCYCLIC COMPOUND HAVING A BRIDGEHEAD NITROGEN ATOM OR SALT THEREOF, AGRICULTURAL OR HORTICULTURAL INSECTICIDE COMPRISING THE COMPOUND, AND METHOD FOR USING THE INSECTICIDE

(71) Applicant: Nihon Nohyaku Co., Ltd., Tokyo (JP)

(72) Inventors: Yusuke Sano, Osaka (JP); Ikki Yonemura, Osaka (JP)

(73) Assignee: Nihon Nohyaku Co., Ltd., Tokyo (JP)

( * ) Notice: Subject to any disclaimer, the term of this patent is extended or adjusted under 35 U.S.C. 154(b) by 556 days.

(21) Appl. No.: 17/595,759

(22) PCT Filed: May 26, 2020

(86) PCT No.: PCT/JP2020/020643
§ 371 (c)(1),
(2) Date: Nov. 23, 2021

(87) PCT Pub. No.: WO2020/241606
PCT Pub. Date: Dec. 3, 2020

(65) Prior Publication Data
US 2022/0242869 A1 Aug. 4, 2022

(30) Foreign Application Priority Data
May 27, 2019 (JP) .................. 2019-098298

(51) Int. Cl.
C07D 487/04 (2006.01)
A01N 43/90 (2006.01)
A01P 7/04 (2006.01)

(52) U.S. Cl.
CPC .......... *C07D 487/04* (2013.01); *A01N 43/90* (2013.01); *A01P 7/04* (2021.08)

(58) Field of Classification Search
CPC ......... C07D 487/04; A01N 43/90; A01P 7/04; A01P 5/00; A01P 7/02; A61P 33/14
See application file for complete search history.

(56) References Cited

U.S. PATENT DOCUMENTS

| | | |
|---|---|---|
| 2011/0039843 A1 | 2/2011 | Iwakoshi et al. |
| 2012/0015975 A1 | 1/2012 | Takahashi et al. |
| 2012/0108586 A1 | 5/2012 | Iwakoshi et al. |
| 2012/0178779 A1 | 7/2012 | Takahashi et al. |
| 2012/0196891 A1 | 8/2012 | Iwakoshi |
| 2012/0245167 A1 | 9/2012 | Iwakoshi et al. |
| 2013/0190271 A1 | 7/2013 | Iwakoshi et al. |
| 2013/0252981 A1 | 9/2013 | Takahashi et al. |
| 2016/0015952 A1 | 1/2016 | Omachi et al. |
| 2016/0255837 A1 | 9/2016 | Edmunds et al. |
| 2017/0073342 A1 | 3/2017 | Fischer et al. |
| 2017/0318809 A1 | 11/2017 | Edmunds et al. |
| 2019/0241564 A1 | 8/2019 | Fischer et al. |
| 2020/0045975 A1 | 2/2020 | Sano et al. |
| 2020/0085054 A1 | 3/2020 | Yonemura et al. |
| 2020/0085056 A1 | 3/2020 | Yonemura et al. |
| 2020/0181172 A1 | 6/2020 | Hager et al. |
| 2021/0059255 A1 | 3/2021 | Tanaka et al. |
| 2021/0371424 A1* | 12/2021 | Sano ............... A01N 43/40 |

FOREIGN PATENT DOCUMENTS

| | | |
|---|---|---|
| EP | 3372595 A1 | 9/2018 |
| JP | 2009-280574 A | 12/2009 |
| JP | 2010-275301 A | 12/2010 |
| JP | 2011-079774 A | 4/2011 |
| JP | 2012-131780 A | 7/2012 |
| JP | 2016-528189 A | 9/2016 |
| WO | WO 2012/086848 A1 | 6/2012 |
| WO | WO 2014/142135 A1 | 9/2014 |
| WO | WO 2015/121136 A1 | 8/2015 |
| WO | WO 2017/065183 A1 | 4/2017 |
| WO | WO 2018/070502 A1 | 4/2018 |

(Continued)

OTHER PUBLICATIONS

English language machine translation of WO 2020054712 A1, translated Jul. 16, 2024. (Year: 2020).*

(Continued)

*Primary Examiner* — Eric Olson
*Assistant Examiner* — Benjamin M Brandsen
(74) *Attorney, Agent, or Firm* — Knobbe Martens Olson & Bear LLP

(57) ABSTRACT

Objects of the present invention are to develop and provide a compound or a salt thereof, and a novel agricultural or horticultural insecticide containing the compound or the salt thereof, and to provide an agent for eliminating ectoparasites or endoparasites of animals. The objects can be achieved by a compound in which a pyridine ring containing an oxime group is bound to a condensed heterocyclic compound having a bridgehead nitrogen atom represented by the following general formula (1):

[Chem. 1]

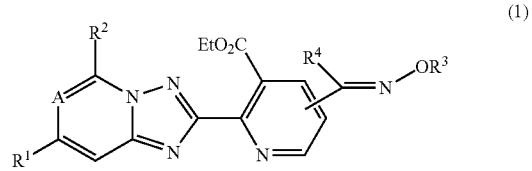

(1)

or a salt thereof, an agricultural or horticultural insecticide containing the compound or the salt thereof as an active ingredient, an animal endoparasite or ectoparasite control agent containing the compound or the salt thereof as an active ingredient, and a method for using the insecticide or the control agent.

7 Claims, No Drawings

(56) References Cited

FOREIGN PATENT DOCUMENTS

| WO | WO 2018/124128 A1 | 7/2018 |
| WO | WO 2018/124129 A1 | 7/2018 |
| WO | WO 2018/199209 A1 | 11/2018 |
| WO | WO 2019/038195 A1 | 2/2019 |
| WO | WO 2019/131575 A1 | 7/2019 |
| WO | WO 2020/054712 A1 | 3/2020 |

OTHER PUBLICATIONS

International Search Report for PCT/JP2020/020643 dated Aug. 18, 2020.

* cited by examiner

CONDENSED HETEROCYCLIC COMPOUND HAVING A BRIDGEHEAD NITROGEN ATOM OR SALT THEREOF, AGRICULTURAL OR HORTICULTURAL INSECTICIDE COMPRISING THE COMPOUND, AND METHOD FOR USING THE INSECTICIDE

CROSS REFERENCE TO RELATED APPLICATIONS

This application is a U.S. National Phase Application of PCT International Application Number PCT/JP2020/020643, filed on May 26, 2020, designating the United States of America and published in the Japanese language, which is an International Application of and claims the benefit of priority to Japanese Patent Application No. 2019-098298, filed on May 27, 2019. The disclosures of the above-referenced applications are hereby expressly incorporated by reference in their entireties.

TECHNICAL FIELD

The present invention relates to an agricultural or horticultural insecticide comprising a condensed heterocyclic compound having a bridgehead nitrogen atom or a salt thereof as an active ingredient, and a method for using the insecticide.

BACKGROUND ART

Various compounds have been examined for their potential as agricultural or horticultural insecticides, and among them, certain kinds of condensed heterocyclic compounds have been reported to be useful as insecticides (for example, see Patent Literature 1 to 11). The literature, however, does not specifically disclose any compound in which a pyridine ring containing an oxime group is bound to a condensed heterocyclic ring having a bridgehead nitrogen atom.

CITATION LIST

Patent Literature

Patent Literature 1: JP-A 2009-280574
Patent Literature 2: JP-A 2010-275301
Patent Literature 3: JP-A 2011-79774
Patent Literature 4: JP-A 2012-131780
Patent Literature 5: WO 2012/086848
Patent Literature 6: WO 2014/142135
Patent literature 7: WO 2015/121136
Patent literature 8: WO 2017/065183
Patent literature 9: WO 2018/124129
Patent Literature 10: WO 2018/199209
Patent literature 11: WO 2019/038195

SUMMARY OF INVENTION

Technical Problem

In crop production in the fields of agriculture, horticulture and the like, the damage caused by insect pests etc. is still immense, and insect pests resistant to existing insecticides have emerged. The present invention has been made in view of such circumstances, and an object of the present invention is to develop and provide a novel agricultural or horticultural insecticide. Another object of the present invention is to provide an agent capable of eliminating ectoparasites or endoparasites of animals.

Solution to Problem

The present inventors conducted intensive research to achieve the above-mentioned object. As a result, the present inventors found that the condensed heterocyclic compound having a bridgehead nitrogen atom represented by the general formula (1) or a salt thereof not only is highly effective in controlling agricultural or horticultural pests, but also has the capability of eliminating ectoparasites or endoparasites of animals while it has little impact on non-target organisms and moderate degradability in the environment. Based on this finding, the present inventors completed the present invention.

That is, the present invention relates to the following.
[1] A condensed heterocyclic compound which has a bridgehead nitrogen atom and is bound to a pyridine ring containing an oxime group, the compound represented by the following formula:

[Chem. 1]

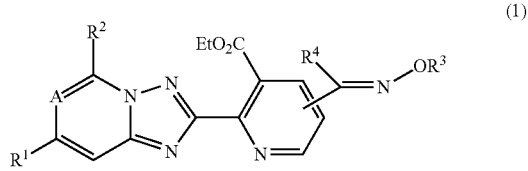

(1)

{wherein
$R^1$ represents
(a1) a hydrogen atom;
(a2) a ($C_1$-$C_6$) alkyl group;
(a3) a ($C_3$-$C_6$) cycloalkyl group; or
(a4) a halo ($C_1$-$C_6$) alkyl group,
$R^2$ represents
(b1) a hydrogen atom;
(b2) a ($C_1$-$C_6$) alkyl group;
(b3) a halo ($C_1$-$C_6$) alkyl group;
(b4) a ($C_3$-$C_6$) cycloalkyl group; or
(b5) a halo ($C_3$-$C_6$) cycloalkyl group,
$R^3$ represents
(c1) a hydrogen atom;
(c2) a ($C_1$-$C_6$) alkyl group;
(c3) a halo ($C_1$-$C_6$) alkyl group;
(c4) a ($C_3$-$C_6$) cycloalkyl group;
(c5) a ($C_3$-$C_6$) cycloalkyl ($C_1$-$C_6$) alkyl group;
(c6) a ($C_1$-$C_6$) alkylthio ($C_1$-$C_6$) alkyl group;
(c7) a ($C_1$-$C_6$) alkylsulfinyl ($C_1$-$C_6$) alkyl group; or
(c8) a ($C_1$-$C_6$) alkylsulfonyl ($C_1$-$C_6$) alkyl group,
$R^4$ represents
(d1) a hydrogen atom;
(d2) a halogen atom;
(d3) a cyano group;
(d4) a ($C_1$-$C_6$) alkyl group;
(d5) a ($C_2$-$C_6$) alkenyl group;
(d6) a ($C_3$-$C_6$) cycloalkyl group;
(d7) a ($C_3$-$C_6$) cycloalkyl ($C_2$-$C_6$) alkynyl group;
(d8) a ($C_1$-$C_6$) alkoxy group;
(d9) a ($C_1$-$C_6$) alkylthio group;
(d10) an $R^6(R^7)N$ group wherein $R^6$ and $R^7$ may be the same or different and each represent a hydrogen atom, a ($C_1$-$C_6$) alkyl group, a halo ($C_1$-$C_6$) alkyl group, a ($C_1$-$C_6$) alkoxycarbonyl group, a ($C_1$-$C_6$) alkylcarbonyl group, or a ($C_3$-$C_6$) cycloalkylcarbonyl group;
(d11) an $NR^6CON(R^6)R^7$ group wherein $R^6$ and $R^7$ are the same as above;
(d12) an aryl group;
(d13) an aryl group having, on the ring, 1 to 4 substituting groups which may be the same or different and are selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (l) a ($C_1$-$C_6$) alkylsulfonyl group, and (m) a halo ($C_1$-$C_6$) alkylsulfonyl group;
(d14) a heterocyclic group; or
(d15) a heterocyclic group having, on the ring, 1 to 3 substituting groups which may be the same or different and are selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (l) a ($C_1$-$C_6$) alkylsulfonyl group, and (m) a halo ($C_1$-$C_6$) alkylsulfonyl group, and
A represents a nitrogen atom or C—$R^5$ wherein $R^5$ represents (e1) a hydrogen atom, (e2) a ($C_1$-$C_6$) alkyl group, or (e3) a halo ($C_1$-$C_6$) alkyl group}.
[2] The condensed heterocyclic compound which has a bridgehead nitrogen atom and is bound to a pyridine ring containing an oxime group according to the above [1], wherein
$R^1$ represents
(a1) a hydrogen atom; or
(a4) a halo ($C_1$-$C_6$) alkyl group,
$R^2$ represents
(b1) a hydrogen atom; or
(b2) a ($C_1$-$C_6$) alkyl group,
$R^3$ represents
(c2) a ($C_1$-$C_6$) alkyl group;
(c3) a halo ($C_1$-$C_6$) alkyl group;
(c6) a ($C_1$-$C_6$) alkylthio ($C_1$-$C_6$) alkyl group;
(c7) a ($C_1$-$C_6$) alkylsulfinyl ($C_1$-$C_6$) alkyl group; or
(c8) a ($C_1$-$C_6$) alkylsulfonyl ($C_1$-$C_6$) alkyl group,
$R^4$ represents
(d1) a hydrogen atom;
(d2) a halogen atom;
(d3) a cyano group;
(d4) a ($C_1$-$C_6$) alkyl group;
(d5) a ($C_2$-$C_6$) alkenyl group;
(d6) a ($C_3$-$C_6$) cycloalkyl group;
(d7) a ($C_3$-$C_6$) cycloalkyl ($C_2$-$C_6$) alkynyl group;
(d8) a ($C_1$-$C_6$) alkoxy group;
(d9) a ($C_1$-$C_6$) alkylthio group;
(d10) an $R^6(R^7)N$ group wherein $R^6$ and $R^7$ are the same as above;
(d11) an $NR^6CON(R^6)R^7$ group wherein $R^6$ and $R^7$ are the same as above;
(d12) an aryl group;
(d13) an aryl group having, on the ring, 1 to 4 substituting groups which may be the same or different and are selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (l) a ($C_1$-$C_6$) alkylsulfonyl group, and (m) a halo ($C_1$-$C_6$) alkylsulfonyl group;
(d14) a heterocyclic group; or
(d15) a heterocyclic group having, on the ring, 1 to 3 substituting groups which may be the same or different and are selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (l) a ($C_1$-$C_6$) alkylsulfonyl group, and (m) a halo ($C_1$-$C_6$) alkylsulfonyl group, and
A represents a nitrogen atom or C—$R^5$ wherein $R^5$ represents (e1) a hydrogen atom, (e2) a ($C_1$-$C_6$) alkyl group, or (e3) a halo ($C_1$-$C_6$) alkyl group.
[3] The condensed heterocyclic compound which has a bridgehead nitrogen atom and is bound to a pyridine ring containing an oxime group or the salt thereof according to the above [1], wherein
$R^1$ represents
(a1) a hydrogen atom; or
(a4) a halo ($C_1$-$C_6$) alkyl group,
$R^2$ represents
(b1) a hydrogen atom; or
(b2) a ($C_1$-$C_6$) alkyl group,
$R^3$ represents
(c2) a ($C_1$-$C_6$) alkyl group;
(c3) a halo ($C_1$-$C_6$) alkyl group;
(c6) a ($C_1$-$C_6$) alkylthio ($C_1$-$C_6$) alkyl group; or
(c8) a ($C_1$-$C_6$) alkylsulfonyl ($C_1$-$C_6$) alkyl group,
$R^4$ represents
(d1) a hydrogen atom;
(d2) a halogen atom;
(d6) a ($C_3$-$C_6$) cycloalkyl group;
(d8) a ($C_1$-$C_6$) alkoxy group;
(d12) an aryl group; or
(d13) an aryl group having, on the ring, 1 to 4 substituting groups which may be the same or different and are selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (l) a ($C_1$-$C_6$) alkylsulfonyl group, and (m) a halo ($C_1$-$C_6$) alkylsulfonyl group, and
A represents a nitrogen atom or C—$R^5$ wherein $R^5$ represents (e1) a hydrogen atom or (e3) a halo ($C_1$-$C_6$) alkyl group.
[4] An agricultural or horticultural insecticide comprising, as an active ingredient, the condensed heterocyclic compound which has a bridgehead nitrogen atom and is bound to a pyridine ring containing an oxime group or the salt thereof according to any one of the above [1] to [3].
[5] A method for using an agricultural or horticultural insecticide, comprising treating plants or soil with an effective amount of the condensed heterocyclic compound which has a bridgehead nitrogen atom and is bound to a pyridine ring containing an oxime group or the salt thereof according to any one of the above [1] to [3].
[6] An animal ectoparasite or endoparasite control agent comprising, as an active ingredient, an effective amount of the condensed heterocyclic compound which has a bridgehead nitrogen atom and is bound to a pyridine ring containing an oxime group or the salt thereof according to any one of the above [1] to [3].

[7] A method for using an animal ectoparasite or endoparasite control agent, comprising transdermally applying or orally administering, to an animal, an effective amount of the condensed heterocyclic compound which has a bridgehead nitrogen atom and is bound to a pyridine ring containing an oxime group or the salt thereof according to any one of the above [1] to [3].

Advantageous Effects of Invention

The condensed heterocyclic compound having a bridgehead nitrogen atom of the present invention or a salt thereof is not only a highly effective agricultural or horticultural insecticide but also is effective against pests which live on pet animals such as dogs and cats and domestic animals such as cattle and sheep and other harmful pests such as termites.

DESCRIPTION OF EMBODIMENTS

In the definitions of the general formula (1) representing the condensed heterocyclic compound having a bridgehead nitrogen atom of the present invention or a salt thereof, "halo" refers to a "halogen atom" and represents a chlorine atom, a bromine atom, an iodine atom or a fluorine atom.

The "$(C_1-C_6)$ alkyl group" refers to a straight-chain or branched-chain alkyl group of 1 to 6 carbon atoms, for example, a methyl group, an ethyl group, a n-propyl group, an isopropyl group, a n-butyl group, an isobutyl group, a sec-butyl group, a tert-butyl group, a n-pentyl group, an isopentyl group, a tert-pentyl group, a neopentyl group, a 2,3-dimethylpropyl group, an 1-ethylpropyl group, a 1-methylbutyl group, a 2-methylbutyl group, a n-hexyl group, an isohexyl group, a 2-hexyl group, a 3-hexyl group, a 2-methylpentyl group, a 3-methylpentyl group, a 1,1,2-trimethyl propyl group, a 3,3-dimethylbutyl group or the like.

The "$(C_3-C_6)$ cycloalkyl group" refers to a cyclic alkyl group of 3 to 6 carbon atoms, for example, a cyclopropyl group, a cyclobutyl group, a cyclopentyl group, a cyclohexyl group or the like. The "$(C_1-C_6)$ alkoxy group" refers to a straight-chain or branched-chain alkoxy group of 1 to 6 carbon atoms, for example, a methoxy group, an ethoxy group, a n-propoxy group, an isopropoxy group, a n-butoxy group, a sec-butoxy group, a tert-butoxy group, a n-pentyloxy group, an isopentyloxy group, a tert-pentyloxy group, a neopentyloxy group, a 2,3-dimethylpropyloxy group, an 1-ethylpropyloxy group, a 1-methylbutyloxy group, a n-hexyloxy group, an isohexyloxy group, a 1,1,2-trimethylpropyloxy group or the like. The "$(C_2-C_6)$ alkenyloxy group" refers to a straight-chain or branched-chain alkenyloxy group of 2 to 6 carbon atoms, for example, a propenyloxy group, a butenyloxy group, a pentenyloxy group, a hexenyloxy group or the like. The "$(C_2-C_6)$ alkynyloxy group" refers to a straight-chain or branched-chain alkynyloxy group of 2 to 6 carbon atoms, for example, a propynyloxy group, a butynyloxy group, a pentynyloxy group, a hexynyloxy group or the like.

The "$(C_1-C_6)$ alkylthio group" refers to a straight-chain or branched-chain alkylthio group of 1 to 6 carbon atoms, for example, a methylthio group, an ethylthio group, a n-propylthio group, an isopropylthio group, a n-butylthio group, a sec-butylthio group, a tert-butylthio group, a n-pentylthio group, an isopentylthio group, a tert-pentylthio group, a neopentylthio group, a 2,3-dimethylpropylthio group, an 1-ethylpropylthio group, a 1-methylbutylthio group, a n-hexylthio group, an isohexylthio group, a 1,1,2-trimethylpropylthio group or the like. The "$(C_1-C_6)$ alkylsulfinyl group" refers to a straight-chain or branched-chain alkylsulfinyl group of 1 to 6 carbon atoms, for example, a methylsulfinyl group, an ethylsulfinyl group, a n-propylsulfinyl group, an isopropylsulfinyl group, a n-butylsulfinyl group, a sec-butylsulfinyl group, a tert-butylsulfinyl group, a n-pentylsulfinyl group, an isopentylsulfinyl group, a tert-pentylsulfinyl group, a neopentylsulfinyl group, a 2,3-dimethylpropylsulfinyl group, an 1-ethylpropylsulfinyl group, a 1-methylbutylsulfinyl group, a n-hexylsulfinyl group, an isohexylsulfinyl group, a 1,1,2-trimethylpropylsulfinyl group or the like. The "$(C_1-C_6)$ alkylsulfonyl group" refers to a straight-chain or branched-chain alkylsulfonyl group of 1 to 6 carbon atoms, for example, a methylsulfonyl group, an ethylsulfonyl group, a n-propylsulfonyl group, an isopropylsulfonyl group, a n-butylsulfonyl group, a sec-butylsulfonyl group, a tert-butylsulfonyl group, a n-pentylsulfonyl group, an isopentylsulfonyl group, a tert-pentylsulfonyl group, a neopentylsulfonyl group, a 2,3-dimethylpropylsulfonyl group, an 1-ethylpropylsulfonyl group, a 1-methylbutylsulfonyl group, a n-hexylsulfonyl group, an isohexylsulfonyl group, a 1,1,2-trimethylpropylsulfonyl group or the like.

The above-mentioned "$(C_1-C_6)$ alkyl group", "$(C_2-C_6)$ alkenyl group", "$(C_2-C_6)$ alkynyl group", "$(C_3-C_6)$ cycloalkyl group", "$(C_3-C_6)$ cycloalkyloxy group", "$(C_1-C_6)$ alkoxy group", "$(C_2-C_6)$ alkenyloxy group", "$(C_2-C_6)$ alkynyloxy group", "$(C_1-C_6)$ alkylthio group", "$(C_1-C_6)$ alkylsulfinyl group", "$(C_1-C_6)$ alkylsulfonyl group", "$(C_2-C_6)$ alkenylthio group", "$(C_2-C_6)$ alkynylthio group", "$(C_2-C_6)$ alkenylsulfinyl group", "$(C_2-C_6)$ alkynylsulfinyl group", "$(C_2-C_6)$ alkenylsulfonyl group", "$(C_2-C_6)$ alkynylsulfonyl group", "$(C_3-C_6)$ cycloalkyl group", "$(C_1-C_6)$ alkoxy group", "$(C_2-C_6)$ alkenyloxy group", "$(C_2-C_6)$ alkynyloxy group", "$(C_3-C_6)$ cycloalkylthio group", "$(C_3-C_6)$ cycloalkylsulfinyl group", and "$(C_3-C_6)$ cycloalkylsulfonyl group" may be substituted with one or more halogen atoms at a substitutable position(s), and in the case where any of the above-listed groups is substituted with two or more halogen atoms, the halogen atoms may be the same or different.

The above-mentioned "groups substituted with one or more halogen atoms" are expressed as a "halo $(C_1-C_6)$ alkyl group", a "halo $(C_2-C_6)$ alkenyl group", a "halo $(C_2-C_6)$ alkynyl group", a "halo $(C_3-C_6)$ cycloalkyl group", a "halo $(C_3-C_6)$ cycloalkyloxy group", a "halo $(C_1-C_6)$ alkoxy group", a "halo $(C_2-C_6)$ alkenyloxy group", a "halo $(C_2-C_6)$ alkynyloxy group", a "halo $(C_1-C_6)$ alkylthio group", a "halo $(C_1-C_6)$ alkylsulfinyl group", a "halo $(C_1-C_6)$ alkylsulfonyl group", a "halo $(C_2-C_6)$ alkenylthio group", a "halo $(C_2-C_6)$ alkynylthio group", a "halo $(C_2-C_6)$ alkenylsulfinyl group", a "halo $(C_2-C_6)$ alkynylsulfinyl group", a "halo $(C_2-C_6)$ alkenylsulfonyl group", a "halo $(C_2-C_6)$ alkynylsulfonyl group", a "halo $(C_3-C_6)$ cycloalkyl group", a "halo $(C_1-C_6)$ alkoxy group", a "halo $(C_2-C_6)$ alkenyloxy group", a "halo $(C_2-C_6)$ alkynyloxy group", a "halo $(C_3-C_6)$ cycloalkylthio group", a "halo $(C_3-C_6)$ cycloalkylsulfinyl group", and a "halo $(C_3-C_6)$ cycloalkylsulfonyl group". The above definitions and examples of each group in the present invention are all obvious to those skilled in the art.

The expressions "$(C_1-C_6)$", "$(C_2-C_6)$", "$(C_3-C_6)$", etc. each represent the range of the number of carbon atoms in each group. The same definition holds true for groups in which two or more of the above-mentioned groups are coupled together, and for example, the "$(C_1-C_6)$ alkoxy $(C_1-C_6)$ alkyl group" means that a straight-chain or branched-chain alkoxy group of 1 to 6 carbon atoms is bound to a straight-chain or branched-chain alkyl group of 1 to 6 carbon atoms.

The "aryl group" refers to an aromatic hydrocarbon group of 6 to 10 carbon atoms, for example, a phenyl group, a 1-naphthyl group, a 2-naphthyl group or the like.

Examples of the "heterocyclic group" include 5- to 6-membered monocyclic aromatic heterocyclic groups having 1 to 5 heteroatoms such as oxygen, nitrogen, and sulfur atoms, such as furyl, thienyl, pyridyl, pyrimidinyl, pyridazinyl, pyrazinyl, pyrrolyl, imidazolyl, pyrazolyl, triazolyl, isothiazolyl, oxazolyl, isoxazolyl, oxadiazolyl, thiadiazolyl, triazolyl, tetrazolyl and triazinyl; and 9- to 18-membered aromatic condensed heterocyclic groups having 1 to 5 heteroatoms such as oxygen, nitrogen, and sulfur atoms, such as quinolyl, isoquinolyl, quinazolyl, quinoxalyl, benzofuranyl, benzothienyl, benzoxazolyl, benzisoxazolyl, benzothiazolyl, benzimidazolyl, benzotriazolyl, indolyl, indazolyl, pyrrolopyrazinyl, imidazopyridinyl, imidazopyrazinyl, pyrazolopyridinyl, pyrazolothienyl and pyrazolotriazinyl.

Examples of the salt of the condensed heterocyclic compound having a bridgehead nitrogen atom represented by the general formula (1) of the present invention include inorganic acid salts, such as hydrochlorides, sulfates, nitrates and phosphates; organic acid salts, such as acetates, fumarates, maleates, oxalates, methanesulfonates, benzenesulfonates and p-toluenesulfonates; and salts with an inorganic or organic base such as a sodium ion, a potassium ion, a calcium ion and a trimethylammonium ion.

The condensed heterocyclic compound having a bridgehead nitrogen atom represented by the general formula (1) of the present invention and a salt thereof can have one or more chiral centers in the structural formula and can exist as two or more kinds of optical isomers or diastereomers. All the optical isomers and mixtures of the isomers at any ratio are also included in the present invention. Further, the compound represented by the general formula (1) of the present invention and a salt thereof can exist as two kinds of geometric isomers due to a carbon-carbon double bond in the structural formula. All the geometric isomers and mixtures of the isomers at any ratio are also included in the present invention. The compound of the present invention can exist as a syn isomer (Z isomer) and/or an anti isomer (E isomer) due to the presence of the oxime group. The compound of the present invention may be either of these isomers, or a mixture of the isomers at any ratio.

In the condensed heterocyclic compound having a bridgehead nitrogen atom represented by the general formula (1) of the present invention or a salt thereof,
$R^1$ is preferably
(a1) a hydrogen atom; or
(a4) a halo $(C_1-C_6)$ alkyl group,
$R^2$ is preferably
(b1) a hydrogen atom; or
(b2) a $(C_1-C_6)$ alkyl group,
$R^3$ is preferably
(c2) a $(C_1-C_6)$ alkyl group;
(c3) a halo $(C_1-C_6)$ alkyl group;
(c6) a $(C_1-C_6)$ alkylthio $(C_1-C_6)$ alkyl group;
(c7) a $(C_1-C_6)$ alkylsulfinyl $(C_1-C_6)$ alkyl group; or
(c8) a $(C_1-C_6)$ alkylsulfonyl $(C_1-C_6)$ alkyl group,
$R^4$ is preferably
(d1) a hydrogen atom;
(d2) a halogen atom;
(d3) a cyano group;
(d4) a $(C_1-C_6)$ alkyl group;
(d5) a $(C_2-C_6)$ alkenyl group;
(d6) a $(C_3-C_6)$ cycloalkyl group;
(d7) a $(C_3-C_6)$ cycloalkyl $(C_2-C_6)$ alkynyl group;
(d8) a $(C_1-C_6)$ alkoxy group;
(d9) a $(C_1-C_6)$ alkylthio group;
(d10) an $R^6(R^7)N$ group wherein $R^6$ and $R^7$ are the same as above;
(d11) an $NR^6CON(R^6)R^7$ group wherein $R^6$ and $R^7$ are the same as above;
(d12) an aryl group;
(d13) an aryl group having, on the ring, 1 to 4 substituting groups which may be the same or different and are selected from (a) a halogen atom, (b) a cyano group, (c) a nitro group, (d) a $(C_1-C_6)$ alkyl group, (e) a halo $(C_1-C_6)$ alkyl group, (f) a $(C_1-C_6)$ alkoxy group, (g) a halo $(C_1-C_6)$ alkoxy group, (h) a $(C_1-C_6)$ alkylthio group, (i) a halo $(C_1-C_6)$ alkylthio group, (j) a $(C_1-C_6)$ alkylsulfinyl group, (k) a halo $(C_1-C_6)$ alkylsulfinyl group, (l) a $(C_1-C_6)$ alkylsulfonyl group, and (m) a halo $(C_1-C_6)$ alkylsulfonyl group;
(d14) a heterocyclic group; or
(d15) a heterocyclic group having, on the ring, 1 to 3 substituting groups which may be the same or different and are selected from (a) a halogen atom, (b) a cyano group, (c) a nitro group, (d) a $(C_1-C_6)$ alkyl group, (e) a halo $(C_1-C_6)$ alkyl group, (f) a $(C_1-C_6)$ alkoxy group, (g) a halo $(C_1-C_6)$ alkoxy group, (h) a $(C_1-C_6)$ alkylthio group, (i) a halo $(C_1-C_6)$ alkylthio group, (j) a $(C_1-C_6)$ alkylsulfinyl group, (k) a halo $(C_1-C_6)$ alkylsulfinyl group, (l) a $(C_1-C_6)$ alkylsulfonyl group, and (m) a halo $(C_1-C_6)$ alkylsulfonyl group, and A is preferably a nitrogen atom or $C-R^5$ wherein $R^5$ represents (e1) a hydrogen atom, (e2) a $(C_1-C_6)$ alkyl group, or (e3) a halo $(C_1-C_6)$ alkyl group.

Furthermore,
$R^1$ is more preferably
(a1) a hydrogen atom; or
(a4) a halo $(C_1-C_6)$ alkyl group,
$R^2$ is more preferably
(b1) a hydrogen atom; or
(b2) a $(C_1-C_6)$ alkyl group,
$R^3$ is more preferably
(c2) a $(C_1-C_6)$ alkyl group;
(c3) a halo $(C_1-C_6)$ alkyl group;
(c6) a $(C_1-C_6)$ alkylthio $(C_1-C_6)$ alkyl group; or
(c8) a $(C_1-C_6)$ alkylsulfonyl $(C_1-C_6)$ alkyl group,
$R^4$ is more preferably
(d1) a hydrogen atom;
(d2) a halogen atom;
(d6) a $(C_3-C_6)$ cycloalkyl group;
(d8) a $(C_1-C_6)$ alkoxy group;
(d12) an aryl group; or
(d13) an aryl group having, on the ring, 1 to 4 substituting groups which may be the same or different and are selected from (a) a halogen atom, (b) a cyano group, (c) a nitro group, (d) a $(C_1-C_6)$ alkyl group, (e) a halo $(C_1-C_6)$ alkyl group, (f) a $(C_1-C_6)$ alkoxy group, (g) a halo $(C_1-C_6)$ alkoxy group, (h) a $(C_1-C_6)$ alkylthio group, (i) a halo $(C_1-C_6)$ alkylthio group, (j) a $(C_1-C_6)$ alkylsulfinyl group, (k) a halo $(C_1-C_6)$ alkylsulfinyl group, (l) a $(C_1-C_6)$ alkylsulfonyl group, and (m) a halo $(C_1-C_6)$ alkylsulfonyl group, and A is more preferably a nitrogen atom or $C-R^5$ wherein $R^5$ represents (e1) a hydrogen atom or (e3) a halo $(C_1-C_6)$ alkyl group.

The condensed heterocyclic compound having a bridgehead nitrogen atom or a salt thereof can be produced, for example, by the method described in WO 2017/065183 or WO 2018/124129, or by the production methods described below, but the present invention is not limited to these methods. The intermediate compounds used in the production methods of the present invention can be commercially

Production Method 1

[Chem. 2]

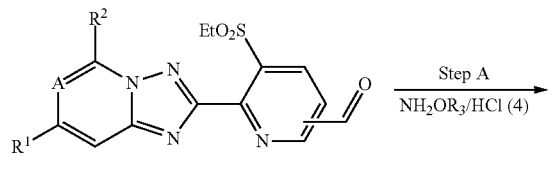

(In the formula, $R^1$, $R^2$, $R^3$, and A are the same as above.)

Production Method at Step [A]

The compound represented by the general formula (1a) can be produced by reacting the compound represented by the general formula (1-4) produced by the method described in Production Method 3 below with the compound ($NH_2OR^3$) represented by the general formula (4) in the presence of a base and an inert solvent.

Examples of the base that can be used in this reaction include inorganic bases such as sodium hydroxide, potassium hydroxide, sodium carbonate, potassium carbonate, sodium hydrogen carbonate and potassium hydrogen carbonate; acetates such as potassium acetate; tertiary amines such as triethylamine, diisopropylethylamine and 1,8-diazabicyclo[5.4.0]undec-7-ene; and nitrogen-containing aromatic compounds such as pyridine and 4-dimethylaminopyridine. The amount of the base used is usually in the range of a 1- to 10-fold molar amount relative to the compound represented by the general formula (4).

The inert solvent used in this reaction may be any solvent that does not markedly inhibit the progress of the reaction, and examples include nonpolar or polar solvents such as aromatic hydrocarbons such as benzene, toluene and xylene; halogenated aromatic hydrocarbons such as chlorobenzene and dichlorobenzene; chain or cyclic ethers such as diethyl ether, methyl tert-butyl ether, dioxane and tetrahydrofuran; esters such as ethyl acetate; alcohols such as methanol and ethanol; amides such as dimethylformamide and dimethylacetamide; and others such as dimethyl sulfoxide and 1,3-dimethyl-2-imidazolidinone; and other inert solvents such as water. One of these inert solvents may be used alone, and also two or more of them may be used as a mixture.

Since this reaction is an equimolar reaction of the compounds, they are basically used in equimolar amounts, but either of them may be used in an excess amount. The reaction temperature may be in the range of room temperature to the boiling point of the inert solvent used. The reaction time varies with the reaction scale and the reaction temperature, but is basically in the range of a few minutes to 48 hours. After the reaction is completed, the compound of interest is isolated from the post-reaction mixture by the usual method. As needed, recrystallization, column chromatography, etc. can be employed for the purification of the compound of interest.

Production Method 2

[Chem. 3]

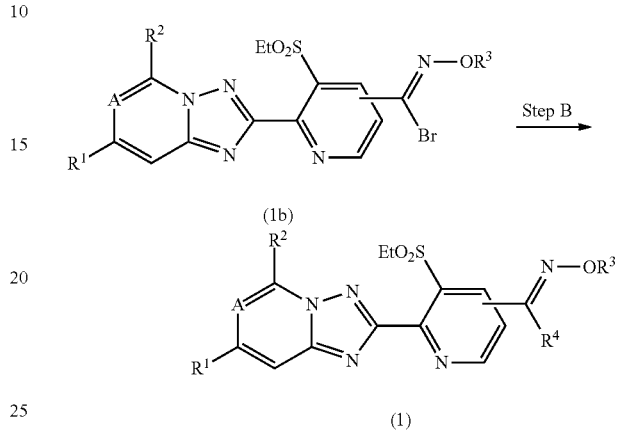

(In the formula, $R^1$, $R^2$, $R^3$, $R^4$, and A are the same as above.)

Production Method at Step [B]

The compound represented by the general formula (1) can be produced by reacting the compound represented by the general formula (1b) produced by the method described in Production Method 4 below with a nucleophile such as sodium methoxide, sodium ethoxide, a dimethylamino group, or 1,2,4-triazole.

The inert solvent used in this reaction may be any solvent that does not markedly inhibit the progress of the reaction, and examples include nonpolar or polar solvents such as aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; chain or cyclic ethers such as diethyl ether, methyl tert-butyl ether, dioxane and tetrahydrofuran; esters such as ethyl acetate; amides such as dimethylformamide and dimethylacetamide; ketones such as acetone and methyl ethyl ketone; and others such as dimethyl sulfoxide and 1,3-dimethyl-2-imidazolidinone. One of these inert solvents may be used alone, and also two or more of them may be used as a mixture.

Since this reaction is an equimolar reaction of the reactants, the compound represented by the general formula (1b) and the nucleophile are used basically in equimolar amounts, but the nucleophile may be used in an excess amount. The reaction temperature may be in the range of −10° C. to the boiling point of the inert solvent used. The reaction time varies with the reaction scale and the reaction temperature, but is basically in the range of a few minutes to 48 hours. After the reaction is completed, the compound of interest is isolated from the post-reaction mixture by the usual method. As needed, recrystallization, column chromatography, etc. can be employed for the purification of the compound of interest.

Alternatively, the compound represented by the general formula (1) can be produced by cross-coupling the compound represented by the general formula (1b) with a corresponding boronic acid ($R^4B(OH)_2$) in the presence of a metal catalyst and a base in an inert solvent.

Examples of the metal catalyst that can be used in this reaction include a palladium catalyst, a nickel catalyst, an iron catalyst, a ruthenium catalyst, a platinum catalyst, a rhodium catalyst and an iridium catalyst. Such a metal catalyst can be used in the form of a metal; a supported metal; a metal salt such as a metal chloride, a metal bromide, a metal iodide, a metal nitrate, a metal sulfate, a metal carbonate, a metal oxalate, a metal acetate and a metal oxide; or a complex compound such as an olefin complex, a phosphine complex, an amine complex, an ammine complex and an acetylacetonate complex. Preferred is a palladium catalyst.

Examples of the palladium catalyst include palladium metals such as palladium black and palladium sponge; and supported palladium metals such as palladium/alumina, palladium/carbon, palladium/silica and palladium/type Y zeolite. Also included are palladium metal salts such as palladium chloride, palladium bromide, palladium iodide and palladium acetate. Examples of the complex compound of palladium include π-allylpalladium chloride dimer, palladium acetylacetonate, dichlorobis(acetonitrile)palladium, dichlorobis(benzonitrile)palladium, bis(dibenzylideneacetone)palladium, tris(dibenzylideneacetone)dipalladium, tris(dibenzylideneacetone)dipalladium (chloroform adduct), dichlorodiamine palladium, dichlorobis(triphenylphosphine)palladium, dichlorobis(tricyclohexylphosphine)palladium, tetrakis(triphenylphosphine)palladium, dichloro[1,2-bis(diphenylphosphino)ethane]palladium, dichloro[1,3-bis(diphenylphosphino)propane]palladium, dichloro[1,4-bis(diphenylphosphino)butane]palladium, dichloro[1,1'-bis(diphenylphosphino)ferrocene]palladium and a [(diphenylphosphino)ferrocene]dichloropalladium-dichloromethane complex.

These palladium catalysts may be used alone or in combination with a tertiary phosphine. Examples of the tertiary phosphine that can be used in combination with the palladium catalyst include triphenylphosphine, trimethylphosphine, triethylphosphine, tributylphosphine, tri(tert-butyl)phosphine, tricyclohexylphosphine, tri-o-tolylphosphine, trioctylphosphine, 9,9-dimethyl-4,5-bis(diphenylphosphino)xanthene, 2-(di-tert-butylphosphino)biphenyl, 2-(dicyclohexylphosphino)biphenyl, 1,2-bis(diphenylphosphino)ethane, 1,3-bis(diphenylphosphino)propane, 1,4-bis(diphenylphosphino)butane, 1,1'-bis(diphenylphosphino)ferrocene, (R)-(+)-2,2'-bis(diphenylphosphino)-1,1'-binaphthyl, (S)-(−)-2,2'-bis(diphenylphosphino)-1,1'-binaphthyl and (±)-2,2'-bis(diphenylphosphino)-1,1'-binaphthyl.

Examples of the boronic acid compound that can be used in this reaction include phenylboronic acid, 3-carboxyphenylboronic acid, 4-chlorophenylboronic acid, 4-(4-propylcyclohexyl)phenylboronic acid, 4-fluorophenylboronic acid, 4-trifluoromethylphenylboronic acid, 4-trifluoromethoxyphenylboronic acid, (4-propylcyclohexyl)phenylboronic acid, and cyclopropylboronic acid. Commercially available products of these compounds can be used.

Examples of the base that can be used in this reaction include inorganic bases such as sodium hydroxide, potassium hydroxide, sodium carbonate, potassium carbonate, cesium carbonate, sodium hydrogen carbonate, and potassium hydrogen carbonate. The amount of the base used is usually in the range of an about 1- to 5-fold molar amount relative to the compound represented by the general formula (1b).

The inert solvent used in this reaction may be any solvent that does not markedly inhibit the reaction, and examples include nonpolar or polar solvents such as alcohols such as methanol, ethanol, propanol, butanol and 2-propanol; chain or cyclic ethers such as diethyl ether, tetrahydrofuran, dioxane and 1,2-dimethoxyethane (DME); aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; nitriles such as acetonitrile; esters such as ethyl acetate; and others such as N,N-dimethylformamide, N,N-dimethylacetamide, dimethyl sulfoxide and 1,3-dimethyl-2-imidazolidinone; and other inert solvents such as water. One of these inert solvents may be used alone, and also two or more of them may be used as a mixture.

The reaction temperature in this reaction is usually in the range of about 0° C. to the boiling point of the solvent used. The reaction time varies with the reaction scale, the reaction temperature and the like, but is basically selected as appropriate from the range of a few minutes to 48 hours. This reaction may be conducted under the atmosphere of an inert gas such as nitrogen gas and argon gas. After the reaction is completed, the compound of interest is isolated from the post-reaction mixture by the usual method. As needed, recrystallization, column chromatography, etc. can be employed for the purification of the compound of interest.

Production Method 3

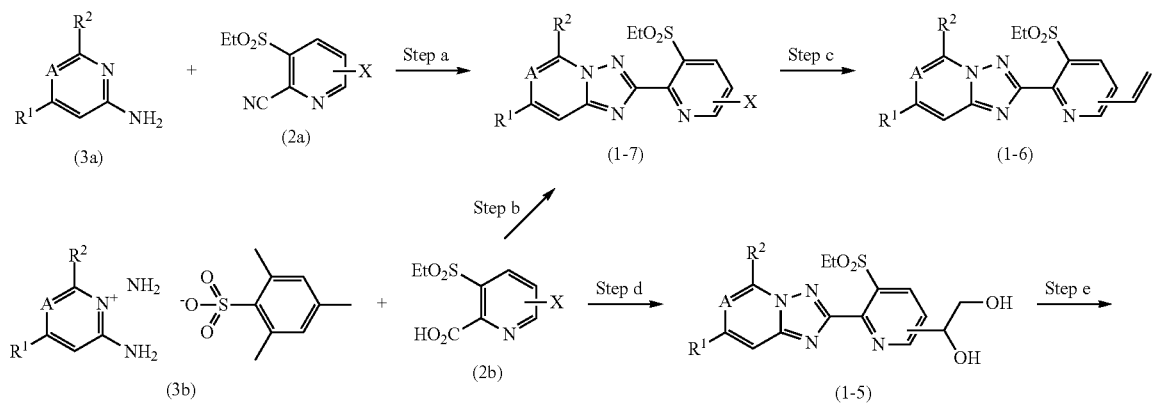

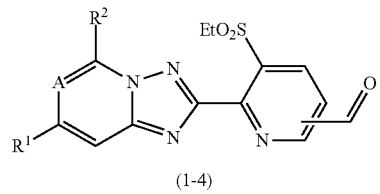

(1-4)

(In the formula, $R^1$, $R^2$, $R^3$, $R^4$, and A are the same as above, and X represents a halogen atom.)

Production Method at Step [a]

The compound represented by the general formula (1-7) can be produced from the compound represented by the general formula (3a) and the compound represented by the general formula (2a) according to the method described in J. Am. Chem. Soc. 2009, 131, 15080-15081 or WO 2013/041472. After the reaction is completed, the compound of interest is isolated from the post-reaction mixture by the usual method. As needed, recrystallization, column chromatography, etc. can be employed for the purification of the compound of interest.

Production Method at Step [b]

Alternatively, the compound represented by the general formula (1-7) can be produced from the compound represented by the general formula (3b), which is produced according to the method described in J. Heterocyclic. Chem., 1975, 12, 107-110 or WO 2015/000715, and the compound represented by the general formula (2b) according to the method described in the aforementioned literature. After the reaction is completed, the compound of interest is isolated from the post-reaction mixture by the usual method. As needed, recrystallization, column chromatography, etc. can be employed for the purification of the compound of interest.

Production Method at Step [c]

The compound represented by the general formula (1-6) can be produced by cross-coupling the compound represented by the general formula (1-7) with a vinylboronic acid compound in the presence of a metal catalyst and a base in an inert solvent.

Examples of the metal catalyst that can be used in this reaction include a palladium catalyst, a nickel catalyst, an iron catalyst, a ruthenium catalyst, a platinum catalyst, a rhodium catalyst and an iridium catalyst. Such a metal catalyst can be used in the form of a metal; a supported metal; a metal salt such as a metal chloride, a metal bromide, a metal iodide, a metal nitrate, a metal sulfate, a metal carbonate, a metal oxalate, a metal acetate and a metal oxide; or a complex compound such as an olefin complex, a phosphine complex, an amine complex, an ammine complex and an acetylacetonate complex.

Examples of the palladium catalyst include palladium metals such as palladium black and palladium sponge; and supported palladium metals such as palladium/alumina, palladium/carbon, palladium/silica and palladium/type Y zeolite. Also included are palladium metal salts such as palladium chloride, palladium bromide, palladium iodide and palladium acetate. Examples of the complex compound of palladium include π-allylpalladium chloride dimer, palladium acetylacetonate, dichlorobis(acetonitrile)palladium, dichlorobis(benzonitrile)palladium, bis(dibenzylideneacetone)palladium, tris(dibenzylideneacetone)dipalladium, tris(dibenzylideneacetone)dipalladium (chloroform adduct), dichlorodiamine palladium, dichlorobis(triphenylphosphine)palladium, dichlorobis(tricyclohexylphosphine)palladium, tetrakis(triphenylphosphine)palladium, dichloro[1,2-bis(diphenylphosphino)ethane]palladium, dichloro[1,3-bis(diphenylphosphino)propane]palladium, dichloro[1,4-bis(diphenylphosphino)butane]palladium, dichloro[1,1'-bis(diphenylphosphino)ferrocene]palladium and a [(diphenylphosphino)ferrocene]dichloropalladium-dichloromethane complex.

These palladium catalysts may be used alone or in combination with a tertiary phosphine. Examples of the tertiary phosphine that can be used in combination with the palladium catalyst include triphenylphosphine, trimethylphosphine, triethylphosphine, tributylphosphine, tri(tert-butyl) phosphine, tricyclohexylphosphine, tri-o-tolylphosphine, trioctylphosphine, 9,9-dimethyl-4,5-bis(diphenylphosphino) xanthene, 2-(di-tert-butylphosphino)biphenyl, 2-(dicyclohexylphosphino)biphenyl, 1,2-bis(diphenylphosphino)ethane, 1,3-bis(diphenylphosphino)propane, 1,4-bis(diphenylphosphino)butane, 1,1'-bis(diphenylphosphino) ferrocene, (R)-(+)-2,2'-bis(diphenylphosphino)-1,1'-binaphthyl, (S)-(−)-2,2'-bis(diphenylphosphino)-1,1'-binaphthyl and (±)-2,2'-bis(diphenylphosphino)-1,1'-binaphthyl.

Examples of the vinylboronic acid compound that can be used in this reaction include vinylmagnesium bromide, vinylmagnesium chloride, vinylzinc chloride, tributylvinyltin, potassium vinyltrifluoroborate, vinylboronic acid, vinylboronic anhydride, vinylboronic acid 2-methyl-2,4-pentanediol ester, vinylboronic acid pinacol ester and triethoxyvinylsilane.

Examples of the base that can be used in this reaction include inorganic bases such as sodium hydroxide, potassium hydroxide, sodium carbonate, potassium carbonate, cesium carbonate, sodium hydrogen carbonate, and potassium hydrogen carbonate. The amount of the base used is usually in the range of an about 1- to 5-fold molar amount relative to the compound represented by the general formula (1-6).

The inert solvent used in this reaction may be any solvent that does not markedly inhibit the reaction, and examples include nonpolar or polar solvents such as alcohols such as methanol, ethanol, propanol, butanol and 2-propanol; chain or cyclic ethers such as diethyl ether, tetrahydrofuran, dioxane and 1,2-dimethoxyethane (DME); aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; nitriles such as acetonitrile; esters such as ethyl acetate; and others such as N,N-dimethylformamide, N,N-dimethylacetamide, dimethyl sulfoxide and 1,3-dimethyl-2-imidazolidinone; and other inert solvents such as water. One of these inert solvents may be used alone, and also two or more of them may be used as a mixture.

The reaction temperature in this reaction is usually in the range of about 0° C. to the boiling point of the solvent used. The reaction time varies with the reaction scale, the reaction temperature and the like, but is basically selected as appropriate from the range of a few minutes to 48 hours. This reaction may be conducted under the atmosphere of an inert gas such as nitrogen gas and argon gas. After the reaction is completed, the compound of interest is isolated from the post-reaction mixture by the usual method. As needed, recrystallization, column chromatography, etc. can be employed for the purification of the compound of interest.

Production Method at Step [d]

The diol-containing condensed heterocyclic compound represented by the general formula (1-5) can be produced by reaction of the vinyl-containing condensed heterocyclic compound represented by the general formula (1-6) in the presence of osmium tetroxide and an oxidizing agent according to the method described in Lecture of Experimental Chemistry (Jikken Kagaku Kouza), 4th edition, vol. 23, Organic Chemistry V, Oxidation Reaction (published by Maruzen Co., Ltd.). After the reaction is completed, the compound of interest is isolated from the post-reaction mixture by the usual method. As needed, recrystallization, column chromatography, etc. can be employed for the purification of the compound of interest. Alternatively, the crude product may be subjected to the next step without purification.

Production Method at Step [e]

The compound represented by the general formula (1-4) can be produced by reacting the diol-containing compound represented by the general formula (1-5) with a periodic acid compound in the presence of an inert solvent according to the method described in New Lecture of Experimental Chemistry (Shin Jikken Kagaku Kouza), vol. 15, Oxidation and Reduction I-1 (published by Maruzen Co., Ltd). After the reaction is completed, the compound of interest is isolated from the post-reaction mixture by the usual method. As needed, recrystallization, column chromatography, etc. can be employed for the purification of the compound of interest.

Production Method 4

[Chem. 5]

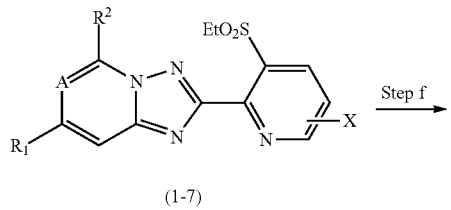

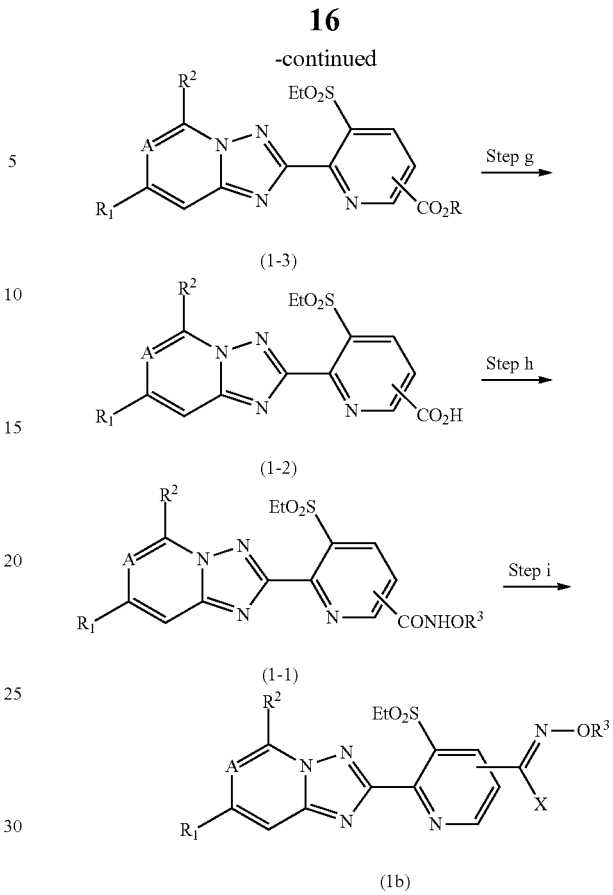

(In the formula, $R^1$, $R^2$, $R^3$, $R^4$, and A are the same as above, and X represents a halogen atom.)

Production Method at Step [f]

The compound represented by the general formula (1-3) can be produced from the compound represented by the general formula (1-7), which is produced by the method described in Production Method 3 above, according to the method described in JP 2005-272338, the so-called Heck reaction. After the reaction is completed, the compound of interest is isolated from the post-reaction mixture by the usual method. If desired, recrystallization, column chromatography, etc. can be employed for the purification of the compound of interest.

Production Method at Step [g]

The compound represented by the general formula (1-2) can be produced by hydrolyzing the compound represented by the general formula (1-3) in the presence of a base and/or an inert solvent.

Examples of the base used in this reaction include inorganic bases such as lithium hydroxide, sodium hydroxide, potassium hydroxide, sodium carbonate, potassium carbonate, cesium carbonate, sodium hydrogen carbonate, and potassium hydrogen carbonate.

The inert solvent used in this reaction may be any solvent that does not markedly inhibit the progress of the reaction, and examples include aromatic hydrocarbons such as benzene, toluene and xylene; halogenated aromatic hydrocarbons such as chlorobenzene and dichlorobenzene; chain or cyclic ethers such as diethyl ether, methyl tert-butyl ether, dioxane and tetrahydrofuran; and water. One of these inert solvents may be used alone, and also two or more of them may be used as a mixture.

The reaction temperature may be in the range of room temperature to the boiling point of the inert solvent used. The reaction time varies with the reaction scale and the reaction temperature, but is basically in the range of a few minutes to 48 hours.

After the reaction is completed, the compound of interest is isolated from the post-reaction mixture by the usual method. As needed, recrystallization etc. can be employed for the purification of the compound of interest.

Production Method at Step [h]

The compound represented by the general formula (1-1) can be produced by reacting the compound represented by the general formula (1-2) with the compound represented by $R^3O-NH_2$ (wherein $R^3$ is the same as above) in the presence of a condensing agent and a base in an inert solvent.

Examples of the condensing agent used in this reaction include 1-ethyl-3-(3-dimethylaminopropyl)carbodiimide hydrochloride (EDCl), diethyl phosphorocyanidate (DEPC), carbonyldiimidazole (CDI), 1,3-dicyclohexylcarbodiimide (DCC), chlorocarbonic esters and 2-chloro-1-methylpyridinium iodide. The amount of the condensing agent used is appropriately selected from the range of a 1- to 1.5-fold molar amount relative to the compound represented by the general formula (1-2).

Examples of the base used include inorganic bases such as sodium hydroxide, potassium hydroxide, sodium carbonate, potassium carbonate, sodium hydrogen carbonate and potassium hydrogen carbonate; acetates such as sodium acetate and potassium acetate; alkali metal alkoxides such as potassium t-butoxide, sodium methoxide and sodium ethoxide; tertiary amines such as triethylamine, diisopropylethylamine and 1,8-diazabicyclo[5.4.0]undec-7-ene; and nitrogen-containing aromatic compounds such as pyridine and dimethylaminopyridine. The amount of the base used is usually in the range of a 1- to 10-fold molar amount relative to the compound represented by the general formula (1-2).

The inert solvent used in this reaction may be any solvent that does not markedly inhibit the progress of the reaction, and examples include aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; chain or cyclic ethers such as diethyl ether, methyl tert-butyl ether, dioxane and tetrahydrofuran; esters such as ethyl acetate; amides such as dimethylformamide and dimethylacetamide; ketones such as acetone and methyl ethyl ketone; and other solvents such as dimethyl sulfoxide and 1,3-dimethyl-2-imidazolidinone. One of these inert solvents may be used alone, and also two or more of them may be used as a mixture.

Since this reaction is an equimolar reaction of the reactants, they are basically used in equimolar amounts, but either of them may be used in an excess amount. The reaction temperature may be in the range of room temperature to the boiling point of the inert solvent used. The reaction time varies with the reaction scale and the reaction temperature, but is basically in the range of a few minutes to 48 hours. After the reaction is completed, the compound of interest is isolated from the post-reaction mixture by the usual method. As needed, recrystallization, column chromatography, etc. can be employed for the purification of the compound of interest.

Production Method at Step [i]

The compound represented by the general formula (1b) can be produced by the so-called Appel reaction (Org. Synth. 54, 63-63), i.e., by reacting the compound represented by the general formula (1-1) with triphenylphosphine and carbon tetrachloride or carbon tetrabromide. After the reaction is completed, the compound of interest is isolated from the post-reaction mixture by the usual method. As needed, recrystallization, column chromatography, etc. can be employed for the purification of the compound of interest.

Specific examples of the compound of the present invention are shown below. In the following tables, Me stands for a methyl group, Et stands for an ethyl group, n-Pr stands for a n-propyl group, i-Pr stands for an isopropyl group, c-Pr stands for a cyclopropyl group, Vinyl stands for a vinyl group, Ph stands for a phenyl group, Py stands for a pyridyl group, and Ac represents an acetyl group. Shown in the column of "Physical property value" is a melting point (° C.) or "$^1$H-NMR". $^1$H-NMR data are shown in Table 10.

[Chem. 6]

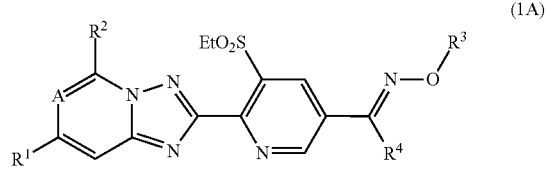

(1A)

TABLE 1

| Compound No. | $R^1$ | $R^3$ | $R^2$ | $R^4$ | A | Physical property value |
|---|---|---|---|---|---|---|
| 1-1 | $CF_3$ | H | H | H | CH | |
| 1-2 | $CF_3$ | Me | H | H | CH | |
| 1-3 | $CF_3$ | Et | H | H | CH | 188-189 |
| 1-4 | $CF_3$ | n-Pr | H | H | CH | |
| 1-5 | $CF_3$ | i-Pr | H | H | CH | 184-185 |
| 1-6 | $CF_3$ | $CH_2CF_3$ | H | H | CH | 191-192 |
| 1-7 | $CF_3$ | $CH_2CHF_2$ | H | H | CH | 189-190 |
| 1-8 | $CF_3$ | $CH_2C_2F_5$ | H | H | CH | 171-172 |
| 1-9 | $CF_3$ | $CH_2CF_2CHF_2$ | H | H | CH | 164-165 |
| 1-10 | $CF_3$ | H | Me | H | CH | |
| 1-11 | $CF_3$ | Me | Me | H | CH | |
| 1-12 | $CF_3$ | Et | Me | H | CH | |
| 1-13 | $CF_3$ | n-Pr | Me | H | CH | |
| 1-14 | $CF_3$ | i-Pr | Me | H | CH | |
| 1-15 | $CF_3$ | $CH_2CF_3$ | Me | H | CH | 210-211 |
| 1-16 | $CF_3$ | $CH_2CHF_2$ | Me | H | CH | 169-170 |
| 1-17 | $CF_3$ | $CH_2C_2F_5$ | Me | H | CH | |
| 1-18 | $CF_3$ | $CH_2CF_2CHF_2$ | Me | H | CH | |
| 1-19 | H | H | H | H | $CCF_3$ | |
| 1-20 | H | Me | H | H | $CCF_3$ | |
| 1-21 | H | Et | H | H | $CCF_3$ | |
| 1-22 | H | n-Pr | H | H | $CCF_3$ | |
| 1-23 | H | i-Pr | H | H | $CCF_3$ | |
| 1-24 | H | $CH_2CF_3$ | H | H | $CCF_3$ | 155-156 |
| 1-25 | H | $CH_2CHF_2$ | H | H | $CCF_3$ | 187-188 |
| 1-26 | H | $CH_2C_2F_5$ | H | H | $CCF_3$ | 145-146 |
| 1-27 | H | $CH_2CF_2CHF_2$ | H | H | $CCF_3$ | 159-160 |

TABLE 2

| Compound No. | R¹ | R³ | R² | R⁴ | A | Physical property value |
|---|---|---|---|---|---|---|
| 1-28 | $CF_3$ | H | H | H | N | |
| 1-29 | $CF_3$ | Me | H | H | N | |
| 1-30 | $CF_3$ | Et | H | H | N | |
| 1-31 | $CF_3$ | n-Pr | H | H | N | |
| 1-32 | $CF_3$ | i-Pr | H | H | N | |
| 1-33 | $CF_3$ | $CH_2CF_3$ | H | H | N | |
| 1-34 | $CF_3$ | $CH_2CHF_2$ | H | H | N | |
| 1-35 | $CF_3$ | $CH_2C_2F_5$ | H | H | N | |
| 1-36 | $CF_3$ | $CH_2CF_2CHF_2$ | H | H | N | |
| 1-37 | $CF_2CF_3$ | H | H | H | N | |
| 1-38 | $CF_2CF_3$ | Me | H | H | N | |
| 1-39 | $CF_2CF_3$ | Et | H | H | N | |
| 1-40 | $CF_2CF_3$ | n-Pr | H | H | N | |
| 1-41 | $CF_2CF_3$ | i-Pr | H | H | N | |
| 1-42 | $CF_2CF_3$ | $CH_2CF_3$ | H | H | N | |
| 1-43 | $CF_2CF_3$ | $CH_2CHF_2$ | H | H | N | |
| 1-44 | $CF_2CF_3$ | $CH_2C_2F_5$ | H | H | N | |
| 1-45 | $CF_2CF_3$ | $CH_2CF_2CHF_2$ | H | H | N | |
| 1-46 | H | $CH_2SCH_3$ | H | H | $CCF_3$ | 151-152 |
| 1-47 | $CF_3$ | $CH_2CH_2SCH_3$ | H | H | CH | 162-164 (TLC, top) *1 |
| 1-48 | $CF_3$ | $CH_2CH_2SCH_3$ | H | H | CH | 140-141 (TLC, bottom) *1 |
| 1-49 | $CF_3$ | $CH_2CH_2SO_2CH_3$ | H | H | CH | 243-245 |
| 1-50 | $CF_3$ | $CH_2CH_2SCH_2CH_3$ | H | H | CH | 148-149 (TLC, top) *2 |
| 1-51 | $CF_3$ | $CH_2CH_2SCH_2CH_3$ | H | H | CH | 82-83 (TLC, bottom) *2 |
| 1-52 | $CF_3$ | $CH_2CH_2SO_2CH_2CH_3$ | H | H | CH | 223-225 |

*1 The compounds 1-47 and 1-48 are isomers (Z and E isomers).
*2 The compounds 1-50 and 1-51 are isomers (Z and E isomers).

[Chem. 7]

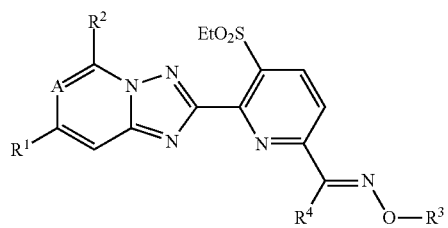

(1B)

TABLE 3

| Compound No. | R¹ | R³ | R² | R⁴ | A | Physical property value |
|---|---|---|---|---|---|---|
| 2-1 | $CF_3$ | H | H | H | CH | |
| 2-2 | $CF_3$ | Me | H | H | CH | |
| 2-3 | $CF_3$ | Et | H | H | CH | |
| 2-4 | $CF_3$ | n-Pr | H | H | CH | |
| 2-5 | $CF_3$ | i-Pr | H | H | CH | |
| 2-6 | $CF_3$ | $CH_2CF_3$ | H | H | CH | 135-136 |
| 2-7 | $CF_3$ | $CH_2CHF_2$ | H | H | CH | 172-173 |
| 2-8 | $CF_3$ | $CH_2C_2F_5$ | H | H | CH | 53-54 |
| 2-9 | $CF_3$ | $CH_2CF_2CHF_2$ | H | H | CH | |
| 2-10 | $CF_3$ | H | Me | H | CH | |
| 2-11 | $CF_3$ | Me | Me | H | CH | |
| 2-12 | $CF_3$ | Et | Me | H | CH | |
| 2-13 | $CF_3$ | n-Pr | Me | H | CH | |
| 2-14 | $CF_3$ | i-Pr | Me | H | CH | |
| 2-15 | $CF_3$ | $CH_2CF_3$ | Me | H | CH | 174-175 |
| 2-16 | $CF_3$ | $CH_2CHF_2$ | Me | H | CH | 167-168 |
| 2-17 | $CF_3$ | $CH_2C_2F_5$ | Me | H | CH | 141-142 |
| 2-18 | $CF_3$ | $CH_2CF_2CHF_2$ | Me | H | CH | |
| 2-19 | H | H | H | H | $CCF_3$ | |
| 2-20 | H | Me | H | H | $CCF_3$ | NMR |
| 2-21 | H | Et | H | H | $CCF_3$ | |
| 2-22 | H | n-Pr | H | H | $CCF_3$ | |
| 2-23 | H | i-Pr | H | H | $CCF_3$ | |
| 2-24 | H | $CH_2CF_3$ | H | H | $CCF_3$ | NMR |
| 2-25 | H | $CH_2CHF_2$ | H | H | $CCF_3$ | 168-170 |
| 2-26 | H | $CH_2C_2F_5$ | H | H | $CCF_3$ | |
| 2-27 | H | $CH_2CF_2CHF_2$ | H | H | $CCF_3$ | |

TABLE 4

| Compound No. | R¹ | R³ | R² | R⁴ | A | Physical property value |
|---|---|---|---|---|---|---|
| 2-28 | $CF_3$ | H | H | H | N | |
| 2-29 | $CF_3$ | Me | H | H | N | |
| 2-30 | $CF_3$ | Et | H | H | N | |
| 2-31 | $CF_3$ | n-Pr | H | H | N | |
| 2-32 | $CF_3$ | i-Pr | H | H | N | |
| 2-33 | $CF_3$ | $CH_2CF_3$ | H | H | N | |
| 2-34 | $CF_3$ | $CH_2CHF_2$ | H | H | N | |
| 2-35 | $CF_3$ | $CH_2C_2F_5$ | H | H | N | |
| 2-36 | $CF_3$ | $CH_2CF_2CHF_2$ | H | H | N | |
| 2-37 | $CF_2CF_3$ | H | H | H | N | |
| 2-38 | $CF_2CF_3$ | Me | H | H | N | |
| 2-39 | $CF_2CF_3$ | Et | H | H | N | |
| 2-40 | $CF_2CF_3$ | n-Pr | H | H | N | |
| 2-41 | $CF_2CF_3$ | i-Pr | H | H | N | |
| 2-42 | $CF_2CF_3$ | $CH_2CF_3$ | H | H | N | 141-142 |
| 2-43 | $CF_2CF_3$ | $CH_2CHF_2$ | H | H | N | 171-172 |
| 2-44 | $CF_2CF_3$ | $CH_2C_2F_5$ | H | H | N | |
| 2-45 | $CF_2CF_3$ | $CH_2CF_2CHF_2$ | H | H | N | |
| 2-46 | $CF_3$ | H | Me | H | N | |
| 2-47 | $CF_3$ | Me | Me | H | N | |
| 2-48 | $CF_3$ | Et | Me | H | N | 190-191 |
| 2-49 | $CF_3$ | n-Pr | Me | H | N | |
| 2-50 | $CF_3$ | i-Pr | Me | H | N | |
| 2-51 | $CF_3$ | $CH_2CF_3$ | Me | H | N | 198-199 |
| 2-52 | $CF_3$ | $CH_2CHF_2$ | Me | H | N | 186-187 |
| 2-53 | $CF_3$ | $CH_2C_2F_5$ | Me | H | N | |
| 2-54 | $CF_3$ | $CH_2CF_2CHF_2$ | Me | H | N | |

[Chem. 8]

(1A)

TABLE 5

| Compound No. | R¹ | R³ | R⁴ | R² | A | Physical property value |
|---|---|---|---|---|---|---|
| 3-1 | $CF_3$ | $CH_2CH_2SCH_3$ | OMe | H | CH | 165-166 |
| 3-2 | $CF_3$ | $CH_2CH_2SOCH_3$ | OMe | H | CH | |
| 3-3 | $CF_3$ | $CH_2CH_2SO_2CH_3$ | OMe | H | CH | |

TABLE 5-continued

| Compound No. | R¹ | R³ | R⁴ | R² | A | Physical property value |
|---|---|---|---|---|---|---|
| 3-4 | $CF_3$ | $CH_2CH_2SCH_3$ | $NH_2$ | H | CH | |
| 3-5 | $CF_3$ | $CH_2CH_2SOCH_3$ | $NH_2$ | H | CH | |
| 3-6 | $CF_3$ | $CH_2CH_2SO_2CH_3$ | $NH_2$ | H | CH | |
| 3-7 | $CF_3$ | $CH_2CH_2SCH_3$ | NHMe | H | CH | |
| 3-8 | $CF_3$ | $CH_2CH_2SOCH_3$ | NHMe | H | CH | |
| 3-9 | $CF_3$ | $CH_2CH_2SO_2CH_3$ | NHMe | H | CH | |
| 3-10 | $CF_3$ | $CH_2CH_2SCH_3$ | $NMe_2$ | H | CH | |
| 3-11 | $CF_3$ | $CH_2CH_2SOCH_3$ | $NMe_2$ | H | CH | |
| 3-12 | $CF_3$ | $CH_2CH_2SO_2CH_3$ | $NMe_2$ | H | CH | |
| 3-13 | $CF_3$ | $CH_2CH_2SCH_3$ | NHAc | H | CH | |
| 3-14 | $CF_3$ | $CH_2CH_2SOCH_3$ | NHAc | H | CH | |
| 3-15 | $CF_3$ | $CH_2CH_2SO_2CH_3$ | NHAc | H | CH | |
| 3-16 | $CF_3$ | $CH_2CH_2SCH_3$ | N(Me)Ac | H | CH | |
| 3-17 | $CF_3$ | $CH_2CH_2SOCH_3$ | N(Me)Ac | H | CH | |
| 3-18 | $CF_3$ | $CH_2CH_2SO_2CH_3$ | N(Me)Ac | H | CH | |
| 3-19 | $CF_3$ | $CH_2CH_2SCH_3$ | Br | H | CH | 188-189 |
| 3-20 | $CF_3$ | $CH_2CH_2SOCH_3$ | Br | H | CH | |
| 3-21 | $CF_3$ | $CH_2CH_2SO_2CH_3$ | Br | H | CH | |
| 3-22 | $CF_3$ | $CH_2CH_2SCH_3$ | SMe | H | CH | |
| 3-23 | $CF_3$ | $CH_2CH_2SOCH_3$ | SMe | H | CH | |
| 3-24 | $CF_3$ | $CH_2CH_2SO_2CH_3$ | SMe | H | CH | |
| 3-25 | $CF_3$ | $CH_2CH_2SCH_3$ | 1,2,4-Triazol-1-yl | H | CH | |
| 3-26 | $CF_3$ | $CH_2CH_2SOCH_3$ | 1,2,4-Triazol-1-yl | H | CH | |
| 3-27 | $CF_3$ | $CH_2CH_2SO_2CH_3$ | 1,2,4-Triazol-1-yl | H | CH | |

TABLE 6

| Compound No. | R¹ | R³ | R⁴ | R² | A | Physical property value |
|---|---|---|---|---|---|---|
| 3-28 | $CF_3$ | $CH_2CH_2SCH_3$ | c-Pr | H | CH | 167-168 |
| 3-29 | $CF_3$ | $CH_2CH_2SOCH_3$ | c-Pr | H | CH | |
| 3-30 | $CF_3$ | $CH_2CH_2SO_2CH_3$ | c-Pr | H | CH | |
| 3-31 | $CF_3$ | $CH_2CH_2SCH_3$ | Vinyl | H | CH | |
| 3-32 | $CF_3$ | $CH_2CH_2SOCH_3$ | Vinyl | H | CH | |
| 3-33 | $CF_3$ | $CH_2CH_2SO_2CH_3$ | Vinyl | H | CH | |
| 3-34 | $CF_3$ | $CH_2CH_2SCH_3$ | Me | H | CH | |
| 3-35 | $CF_3$ | $CH_2CH_2SOCH_3$ | Me | H | CH | |
| 3-36 | $CF_3$ | $CH_2CH_2SO_2CH_3$ | Me | H | CH | |
| 3-37 | $CF_3$ | $CH_2CH_2SCH_3$ | CC-c-Pr | H | CH | |
| 3-38 | $CF_3$ | $CH_2CH_2SOCH_3$ | CC-c-Pr | H | CH | |
| 3-39 | $CF_3$ | $CH_2CH_2SO_2CH_3$ | CC-c-Pr | H | CH | |
| 3-40 | $CF_3$ | $CH_2CH_2SCH_3$ | $NHCO_2Me$ | H | CH | |
| 3-41 | $CF_3$ | $CH_2CH_2SOCH_3$ | $NHCO_2Me$ | H | CH | |
| 3-42 | $CF_3$ | $CH_2CH_2SO_2CH_3$ | $NHCO_2Me$ | H | CH | |
| 3-43 | $CF_3$ | $CH_2CH_2SCH_3$ | NHCONHMe | H | CH | |
| 3-44 | $CF_3$ | $CH_2CH_2SOCH_3$ | NHCONHMe | H | CH | |
| 3-45 | $CF_3$ | $CH_2CH_2SO_2CH_3$ | NHCONHMe | H | CH | |
| 3-46 | $CF_3$ | $CH_2CH_2SCH_3$ | Ph | H | CH | 157-158 |
| 3-47 | $CF_3$ | $CH_2CH_2SOCH_3$ | Ph | H | CH | |
| 3-48 | $CF_3$ | $CH_2CH_2SO_2CH_3$ | Ph | H | CH | |
| 3-49 | $CF_3$ | $CH_2CH_2SCH_3$ | CN | H | CH | |
| 3-50 | $CF_3$ | $CH_2CH_2SOCH_3$ | CN | H | CH | |
| 3-51 | $CF_3$ | $CH_2CH_2SO_2CH_3$ | CN | H | CH | |
| 3-52 | $CF_3$ | $CH_2CH_2SCH_3$ | 3-$OCF_3$Ph | H | CH | 125-127 |
| 3-53 | $CF_3$ | $CH_2CH_2SOCH_3$ | 3-$OCF_3$Ph | H | CH | |
| 3-54 | $CF_3$ | $CH_2CH_2SO_2CH_3$ | 3-$OCF_3$Ph | H | CH | |

TABLE 7

| Compound No. | R¹ | R³ | R⁴ | R² | A | Physical property value |
|---|---|---|---|---|---|---|
| 3-55 | $CF_3$ | $CH_2CH_2SCH_3$ | 3-Thienyl | H | CH | |
| 3-56 | $CF_3$ | $CH_2CH_2SOCH_3$ | 3-Thienyl | H | CH | |
| 3-57 | $CF_3$ | $CH_2CH_2SO_2CH_3$ | 3-Thienyl | H | CH | |
| 3-58 | $CF_3$ | $CH_2CH_2SCH_3$ | 1-Methypyrazol-4-yl | H | CH | |
| 3-59 | $CF_3$ | $CH_2CH_2SOCH_3$ | 1-Methypyrazol-4-yl | H | CH | |
| 3-60 | $CF_3$ | $CH_2CH_2SO_2CH_3$ | 1-Methylpyrazol-4-yl | H | CH | |
| 3-61 | $CF_3$ | $CH_2CH_2SCH_3$ | 1-Methypyrazol-5-yl | H | CH | |
| 3-62 | $CF_3$ | $CH_2CH_2SOCH_3$ | 1-Methypyrazol-5-yl | H | CH | |
| 3-63 | $CF_3$ | $CH_2CH_2SO_2CH_3$ | 1-Methylpyrazol-5-yl | H | CH | |
| 3-64 | H | $CH_2CH_2SCH_3$ | OMe | H | $CCF_3$ | |
| 3-65 | H | $CH_2CH_2SOCH_3$ | OMe | H | $CCF_3$ | |
| 3-66 | H | $CH_2CH_2SO_2CH_3$ | OMe | H | $CCF_3$ | |
| 3-67 | H | $CH_2CH_2SCH_3$ | $NH_2$ | H | $CCF_3$ | |
| 3-68 | H | $CH_2CH_2SOCH_3$ | $NH_2$ | H | $CCF_3$ | |
| 3-69 | H | $CH_2CH_2SO_2CH_3$ | $NH_2$ | H | $CCF_3$ | |
| 3-70 | H | $CH_2CH_2SCH_3$ | NHMe | H | $CCF_3$ | |
| 3-71 | H | $CH_2CH_2SOCH_3$ | NHMe | H | $CCF_3$ | |
| 3-72 | H | $CH_2CH_2SO_2CH_3$ | NHMe | H | $CCF_3$ | |
| 3-73 | H | $CH_2CH_2SCH_3$ | $NMe_2$ | H | $CCF_3$ | |
| 3-74 | H | $CH_2CH_2SOCH_3$ | $NMe_2$ | H | $CCF_3$ | |
| 3-75 | H | $CH_2CH_2SO_2CH_3$ | $NMe_2$ | H | $CCF_3$ | |
| 3-76 | H | $CH_2CH_2SCH_3$ | NHAc | H | $CCF_3$ | |
| 3-77 | H | $CH_2CH_2SOCH_3$ | NHAc | H | $CCF_3$ | |
| 3-78 | H | $CH_2CH_2SO_2CH_3$ | NHAc | H | $CCF_3$ | |
| 3-79 | H | $CH_2CH_2SCH_3$ | N(Me)Ac | H | $CCF_3$ | |
| 3-80 | H | $CH_2CH_2SOCH_3$ | N(Me)Ac | H | $CCF_3$ | |
| 3-81 | H | $CH_2CH_2SO_2CH_3$ | N(Me)Ac | H | $CCF_3$ | |

TABLE 8

| Compound No. | R¹ | R³ | R⁴ | R² | A | Physical property value |
|---|---|---|---|---|---|---|
| 3-82 | H | $CH_2CH_2SCH_3$ | Br | H | $CCF_3$ | 151-152 |
| 3-83 | H | $CH_2CH_2SOCH_3$ | Br | H | $CCF_3$ | |
| 3-84 | H | $CH_2CH_2SO_2CH_3$ | Br | H | $CCF_3$ | |

TABLE 8-continued

| Compound No. | R¹ | R³ | R⁴ | R² | A | Physical property value |
|---|---|---|---|---|---|---|
| 3-85 | H | CH₂CH₂SCH₃ | SMe | H | CCF₃ | |
| 3-86 | H | CH₂CH₂SOCH₃ | SMe | H | CCF₃ | |
| 3-87 | H | CH₂CH₂SO₂CH₃ | SMe | H | CCF₃ | |
| 3-88 | H | CH₂CH₂SCH₃ | 1,2,4-Triazol-1-yl | H | CCF₃ | |
| 3-89 | H | CH₂CH₂SOCH₃ | 1,2,4-Triazol-1-yl | H | CCF₃ | |
| 3-90 | H | CH₂CH₂SO₂CH₃ | 1,2,4-Triazol-1-yl | H | CCF₃ | |
| 3-91 | H | CH₂CH₂SCH₃ | c-Pr | H | CCF₃ | |
| 3-92 | H | CH₂CH₂SOCH₃ | c-Pr | H | CCF₃ | |
| 3-93 | H | CH₂CH₂SO₂CH₃ | c-Pr | H | CCF₃ | |
| 3-94 | H | CH₂CH₂SCH₃ | Vinyl | H | CCF₃ | |
| 3-95 | H | CH₂CH₂SOCH₃ | Vinyl | H | CCF₃ | |
| 3-96 | H | CH₂CH₂SO₂CH₃ | Vinyl | H | CCF₃ | |
| 3-97 | H | CH₂CH₂SCH₃ | Me | H | CCF₃ | |
| 3-98 | H | CH₂CH₂SOCH₃ | Me | H | CCF₃ | |
| 3-99 | H | CH₂CH₂SO₂CH₃ | Me | H | CCF₃ | |
| 3-100 | H | CH₂CH₂SCH₃ | CC-c-Pr | H | CCF₃ | |
| 3-101 | H | CH₂CH₂SOCH₃ | CC-c-Pr | H | CCF₃ | |
| 3-102 | H | CH₂CH₂SO₂CH₃ | CC-c-Pr | H | CCF₃ | |
| 3-103 | H | CH₂CH₂SCH₃ | NHCO₂Me | H | CCF₃ | |
| 3-104 | H | CH₂CH₂SOCH₃ | NHCO₂Me | H | CCF₃ | |
| 3-105 | H | CH₂CH₂SO₂CH₃ | NHCO₂Me | H | CCF₃ | |
| 3-106 | H | CH₂CH₂SCH₃ | NHCONHMe | H | CCF₃ | |
| 3-107 | H | CH₂CH₂SOCH₃ | NHCONHMe | H | CCF₃ | |
| 3-108 | H | CH₂CH₂SO₂CH₃ | NHCONHMe | H | CCF₃ | |

TABLE 9

| Compound No. | R¹ | R³ | R⁴ | R² | A | Physical property value |
|---|---|---|---|---|---|---|
| 3-109 | H | CH₂CH₂SCH₃ | Ph | H | CCF₃ | |
| 3-110 | H | CH₂CH₂SOCH₃ | Ph | H | CCF₃ | |
| 3-111 | H | CH₂CH₂SO₂CH₃ | Ph | H | CCF₃ | |
| 3-112 | H | CH₂CH₂SCH₃ | CN | H | CCF₃ | |
| 3-113 | H | CH₂CH₂SOCH₃ | CN | H | CCF₃ | |
| 3-114 | H | CH₂CH₂SO₂CH₃ | CN | H | CCF₃ | |
| 3-115 | H | CH₂CH₂SCH₃ | 3-Py | H | CCF₃ | |
| 3-116 | H | CH₂CH₂SOCH₃ | 3-Py | H | CCF₃ | |
| 3-117 | H | CH₂CH₂SO₂CH₃ | 3-Py | H | CCF₃ | |
| 3-118 | H | CH₂CH₂SCH₃ | 3-Thienyl | H | CCF₃ | |
| 3-119 | H | CH₂CH₂SOCH₃ | 3-Thienyl | H | CCF₃ | |
| 3-120 | H | CH₂CH₂SO₂CH₃ | 3-Thienyl | H | CCF₃ | |
| 3-121 | H | CH₂CH₂SCH₃ | 1-Methypyrazol-4-yl | H | CCF₃ | |
| 3-122 | H | CH₂CH₂SOCH₃ | 1-Methypyrazol-4-yl | H | CCF₃ | |
| 3-123 | H | CH₂CH₂SO₂CH₃ | 1-Methylpyrazol-4-yl | H | CCF₃ | |
| 3-124 | H | CH₂CH₂SCH₃ | 1-Methylpyrazol-5-yl | H | CCF₃ | |
| 3-125 | H | CH₂CH₂SOCH₃ | 1-Methylpyrazol-5-yl | H | CCF₃ | |
| 3-126 | H | CH₂CH₂SO₂CH₃ | 1-Methylpyrazol-5-yl | H | CCF₃ | |

TABLE 10

H-NMR Data

| Compound No. | ¹H-NMR Data(CDCl₃) |
|---|---|
| 2-20 | 9.00(s, 1H), 8.58(d, 1H), 8.30(s, 1H), 8.20(d, 1H), 7.94(d, 1H), 7.77(dd, 1H), 4.08(s, 3H), 3.91 (q, 2H), 1.40(t, 3H) |
| 2-24 | 9.01(s, 1H), 8.53(d, 1H), 8.43(s, 1H), 8.20(d, 1H), 7.95(d, 1H), 7.77(dd, 1H), 4.62(q, 2H), 3.92(q, 2H), 1.40(t, 3H) |

The agricultural or horticultural insecticide comprising the condensed heterocyclic compound having a bridgehead nitrogen atom represented by the general formula (1) of the present invention or a salt thereof as an active ingredient is suitable for controlling a variety of pests which may damage paddy rice, fruit trees, vegetables, other crops and ornamental flowering plants. The target pests are, for example, agricultural and forest pests, horticultural pests, stored grain pests, sanitary pests, nematodes, termites, etc.

Specific examples of the pests, nematodes, etc. include the following:

the species of the order Lepidoptera such as *Parasa consocia, Anomis mesogona, Papilio xuthus, Matsumuraeses azukivora, Ostrinia scapulalis, Spodoptera exempta, Hyphantria cunea, Ostrinia furnacalis, Pseudaletia separata, Tinea translucens, Bactra furfurana, Parnara guttata, Marasmia exigua, Parnara guttata, Sesamia inferens, Brachmia triannulella, Monema flavescens, Trichoplusia ni, Pleuroptya ruralis, Cystidia couaggaria, Lampides boeticus, Cephonodes hylas, Helicoverpa armigera, Phalerodonta manleyi, Eumeta japonica, Pieris brassicae, Malacosoma neustria testacea, Stathmopoda masinissa, Cuphodes diospyrosella, Archips xylosteanus, Agrotis segetum, Tetramoera schistaceana, Papilio machaon hippocrates, Endoclyta sinensis, Lyonetia prunifoliella, Phyllonorycter ringoneella, Cydia kurokoi, Eucoenogenes aestuosa, Lobesia botrana, Latoia sinica, Euzophera batangensis, Phalonidia mesotypa, Spilosoma imparilis, Glyphodes pyloalis, Olethreutes mori, Tineola bissellella, Endoclyta excrescens, Nemapogon granellus, Synanthedon hector, Cydia pomonella, Plutella xylostella, Cnaphalocrocis medinalis, Sesamia calamistis, Scirpophaga incertulas, Pediasia teterrellus, Phthorimaea operculella, Stauropus fagi persimilis, Etiella zinckenella, Spodoptera exigua, Palpifer sexnotata, Spodoptera mauritia, Scirpophaga innotata, Xestia c-nigrum, Spodoptera depravata, Ephestia kuehniella, Angerona prunaria, Clostera anastomosis, Pseudoplusia includens, Matsumuraeses falcana, Helicoverpa assulta, Autographa nigrisigna, Agrotis Euproctis pseudoconspersa, Adoxophyes orana, Caloptilia theivora, Homona magnanima, Ephestia elutella, Eumeta minuscula, Clostera anachoreta, Heliothis maritima, Sparganothis pilleriana, Busseola fusca, Euproctis subflava, Biston robustum, Heliothis zea, Aedia leucomelas, Narosoideus flavidorsalis, Viminia rumicis, Bucculatrix pyrivorella, Grapholita molesta, Spulerina astaurota, Ectomyelois pyrivorella, Chilo suppressalis, Acrolepiopsis sapporensis, Plodia interpunctella, Hellula undalis, Sitotroga cerealella, Spodoptera litura, a* species *of the family Tortricidae (Eucosma aporema), Acleris comariana, Scopelodes contractus, Orgyia thyellina, Spodoptera frugiperda, Ostrinia zaguliaevi, Naranga aenescens, And-* raca bipunctata, Paranthrene regalis, Acosmeryx castanea, Phyllocnistis toparcha, Endopiza viteana, Eupoecillia ambiguella, Anticarsia gemmatalis, Cnephasia cinereipalpana, Lymantria dispar, Dendrolimus spectabilis, Leguminivora glycinivorella, Maruca testulalis, Matsumuraeses phaseoli, Caloptilia soyella, Phyllocnistis citrella, Omiodes indicata, Archips fuscocupreanus, Acanthoplusia agnata, Bambalina sp., Carposina niponensis, Conogethes punctiferalis, Synanthedon sp., Lyonetia clerkella, Papilio helenus, Colias erate poliographus, Phalera flavescens, the species of the family Pieridae such as Pieris rapae crucivora and Pieris rapae, Euproctis similis, Acrolepiopsis suzukiella, Ostrinia nubilalis, Mamestra brassicae, Ascotis selenaria, Phtheochroides clandestina, Hoshinoa adumbratana, Odonestis pruni japonensis, Triaena intermedia, Adoxophyes orana fasciata, Grapholita inopinata, Spilonota ocellana, Spilonota lechriaspis, Illiberis pruni, Argyresthia conjugella, Caloptilia zachrysa, Archips breviplicanus, Anomis flava, Pectinophora gossypiella, Notarcha derogata, Diaphania indica, Heliothis virescens and Earias cupreoviridis;

the species of the order Hemiptera such as Nezara antennata, Stenotus rubrovittatus, Graphosoma rubrolineatum, Trigonotylus coelestialium, Aeschynteles maculatus, Creontiades pallidifer, Dysdercus cingulatus, Chrysomphalus ficus, Aonidiella aurantii, Graptopsaltria nigrofuscata, Blissus leucopterus, Icerya purchasi, Piezodorus hybneri, Lagynotomus elongatus, Thaia subrufa, Scotinophara lurida, Sitobion ibarae, Stariodes iwasakii, Aspidiotus destructor, Taylorilygus pallidulus, Myzus mumecola, Pseudaulacaspis prunicola, Acyrthosiphon pisum, Anacanthocoris striicornis, Ectometopterus micantulus, Eysarcoris lewisi, Molipteryx fuliginosa, Cicadella viridis, Rhopalosophum rufiabdominalis, Saissetia oleae, Trialeurodes vaporariorum, Aguriahana quercus, Lygus spp., Euceraphis punctipennis, Andaspis kashicola, Coccus pseudomagnoliarum, Cavelerius saccharivorus, Galeatus spinifrons, Macrosiphoniella sanborni, Aonidiella citrina, Halyomorpha mista, Stephanitis fasciicarina, Trioza camphorae, Leptocorisa chinensis, Trioza quercicola, Uhlerites latius, Erythroneura comes, Paromius exiguus, Duplaspidiotus claviger, Nephotettix nigropictus, Halticiellus insularis, Perkinsiella saccharicida, Psylla malivorella, Anomomeura mori, Pseudococcus longispinis, Pseudaulacaspis pentagona, Pulvinaria kuwacola, Apolygus lucorum, Togo hemipterus, Toxoptera aurantii, Saccharicoccus sacchari, Geoica lucifuga, Numata muiri, Comstockaspis perniciosa, Unaspis citri, Aulacorthum solani, Eysarcoris ventralis, Bemisia argentifolii, Cicadella spectra, Aspidiotus hederae, Liorhyssus hyalinus, Calophya nigridorsalis, Sogatella furcifera, Megoura crassicauda, Brevicoryne brassicae, Aphis glycines, Leptocorisa oratorius, Nephotettix virescens, Uroeucon formosanum, Cyrtopeltis tennuis, Bemisia tabaci, Lecanium persicae, Parlatoria theae, Pseudaonidia paeoniae, Empoasca onukii, Plautia stali, Dysaphis tulipae, Macrosiphum euphorbiae, Stephanitis pyrioides, Ceroplastes ceriferus, Parlatoria camelliae, Apolygus spinolai, Nephotettix cincticeps, Glaucias subpunctatus, Orthotylus flavosparsus, Rhopalosiphum maidis, Peregrinus maidis, Eysarcoris parvus, Cimex lectularius, Psylla abieti, Nilaparvata lugens, Psylla tobirae, Eurydema rugosum, Schizaphis piricola, Psylla pyricola, Parlatoreopsis pyri, Stephanitis nashi, Dysmicoccus wistariae, Lepholeucaspis japonica, Sappaphis piri, Lipaphis erysimi, Neotoxoptera formosana, Rhopalosophum nymphaeae, Edwardsiana rosae, Pinnaspis aspidistrae, Psylla alni, Speusotettix subfusculus, Alnetoidia alneti, Sogatella panicicola, Adelphocoris lineolatus, Dysdercus poecilus, Parlatoria ziziphi, Uhlerites debile, Laodelphax striatellus, Eurydema pulchrum, Cletus trigonus, Clovia punctata, Empoasca spp., Coccus hesperidum, Pachybrachius luridus, Planococcus kraunhiae, Stenotus binotatus, Arboridia apicalis, Macrosteles fascifrons, Dolycoris baccarum, Adelphocoris triannulatus, Viteus vitifolii, Acanthocoris sordidus, Leptocorisa acuta, Macropes obnubilus, Cletus punctiger, Riptortus clavatus, Paratrioza cockerelli, Aphrophora costalis, Lygus disponsi, Lygus saundersi, Crisicoccus pini, Empoasca abietis, Crisicoccus matsumotoi, Aphis craccivora, Megacopta punctatissimum, Eysarcoris guttiger, Lepidosaphes beckii, Diaphorina citri, Toxoptera citricidus, Planococcus citri, Dialeurodes citri, Aleurocanthus spiniferus, Pseudococcus citriculus, Zyginella citri, Pulvinaria citricola, Coccus discrepans, Pseudaonidia duplex, Pulvinaria aurantii, Lecanium corni, Nezara viridula, Stenodema calcaratum, Rhopalosiphum padi, Sitobion akebiae, Schizaphis graminum, Sorhoanus tritici, Brachycaudus helichrysi, Carpocoris purpureipennis, Myzus persicae, Hyalopterus pruni, Aphis farinose yanagicola, Metasalis populi, Unaspis yanonensis, Mesohomotoma camphorae, Aphis spiraecola, Aphis pomi, Lepidosaphes ulmi, Psylla mali, Heterocordylus flavipes, Myzus malisuctus, Aphidonuguis mali, Orientus ishidai, Ovatus malicolens, Eriosoma lanigerum, Ceroplastes rubens and Aphis gossypii; the species of the order Coleoptera such as Xystrocera globosa, Paederus fuscipes, Eucetonia roelofsi, Callosobruchus chinensis, Cylas formicarius, Hypera postica, Echinocnemus squameus, Oulema oryzae, Donacia provosti, Lissorhoptrus oryzophilus, Colasposoma dauricum, Euscepes postfasciatus, Epilachna varivestis, Acanthoscelides obtectus, Diabrotica virgifera virgifera, Involvulus cupreus, Aulacophora femoralis, Bruchus pisorum, Epilachna vigintioctomaculata, Carpophilus dimidiatus, Cassida nebulosa, Luperomorpha tunebrosa, Phyllotreta striolata, Psacothea hilaris, Aeolesthes chrysothrix, Curculio sikkimensis, Carpophilus hemipterus, Oxycetonia jucunda, Diabrotica spp., Mimela splendens, Sitophilus zeamais, Tribolium castaneum, Sitophilus oryzae, Palorus subdepressus, Melolontha japonica, Anoplophora malasiaca, Neatus picipes, Leptinotarsa decemlineata, Diabrotica undecimpunctata howardi, Sphenophorus venatus, Crioceris quatuordecimpunctata, Conotrachelus nenuphar, Ceuthorhynchidius albosuturalis, Phaedon brassicae, Lasioderma serricorne, Sitona japonicus, Adoretus tenuimaculatus, Tenebrio molitor, Basilepta balyi, Hypera nigrirostris, Chaetocnema concinna, Anomala cuprea, Heptophylla picea, Epilachna vigintioctopunctata, Diabrotica longicornis, Eucetonia pilifera, Agriotes spp., Attagenus unicolor japonicus, Pagria signata, Anomala rufocuprea, Palorus ratzeburgii, Alphitobius laevigatus, Anthrenus verbasci, Lyctus brunneus, Tribolium confusum, Medythia nigrobilineata, Xylotrechus pyrrhoderus, Epitrix cucumeris, Tomicus piniperda, Monochamus alternatus, Popillia japonica, Epicauta gorhami, Sitophilus zeamais, Rhynchites heros, Listroderes costirostris, Callosobruchus maculatus, Phyllobius armatus, Anthonomus pomorum, Linaeidea aenea and Anthonomus grandis;

the species of the order Diptera such as Culex pipiens pallens, Pegomya hyoscyami, Liriomyza huidobrensis, Musca domestica, Chlorops oryzae, Hydrellia sasakii, Agromyza oryzae, Hydrellia griseola, Hydrellia griseola, Ophiomyia phaseoli, Dacus cucurbitae, Drosophila suzukii, Rhacochlaena japonica, Muscina stabulans, the species of the family Phoridae such as Megaselia spiracularis, Clogmia albipunctata, Tipula aino, Phormia regina, Culex tritaeniorhynchus, Anopheles sinensis, Hylemya brassicae, Asphondylia sp., *Delia platura*, *Delia antiqua*, *Rhagoletis cerasi*, *Culex pipiens molestus Forskal*, *Ceratitis capitata*, *Bradysia agrestis*, *Pegomya cunicularia*, *Liriomyza sativae*, *Liriomyza bryoniae*, *Chromatomyia horticola*, *Liriomyza chinensis*, *Culex quinquefasciatus*, *Aedes aegypti*, *Aedes albopictus*, *Liriomyza trifolii*, *Liriomyza sativae*, *Dacus dorsalis*, *Dacus tsuneonis*, *Sitodiplosis mosellana*, *Meromuza nigriventris*, *Anastrepha ludens* and *Rhagoletis pomonella*;

the species of the order Hymenoptera such as *Pristomyrmex pungens*, Bethylid wasps, *Monomorium pharaonis*, *Pheidole noda*, *Athalia rosae*, *Dryocosmus kuriphilus*, *Formica fusca japonica*, Vespid wasps, *Athalia infumata infumata*, *Arge pagana*, *Athalia japonica*, *Acromyrmex* spp., *Solenopsis* spp., *Arge mali* and *Ochetellus glaber*;

the species of the order Orthoptera such as *Homorocoryphus lineosus*, *Gryllotalpa* sp., *Oxya hyla intricata*, *Oxya yezoensis*, *Locusta migratoria*, *Oxya japonica*, *Homorocoryphus jezoensis* and *Teleogryllus emma*;

the species of the order Thysanoptera such as *Selenothrips rubrocinctus*, *Stenchaetothrips biformis*, *Haplothrips aculeatus*, *Ponticulothrips diospyrosi*, *Thrips flavus*, *Anaphothrips obscurus*, *Liothrips floridensis*, *Thrips simplex*, *Thrips nigropilosus*, *Heliothrips haemorrhoidalis*, *Pseudodendrothrips mori*, *Microcephalothrips abdominalis*, *Leeuwenia pasanii*, *Litotetothrips pasaniae*, *Scirtothrips citri*, *Haplothrips chinensis*, *Mycterothrips glycines*, *Thrips setosus*, *Scirtothrips dorsalis*, *Dendrothrips minowai*, *Haplothrips niger*, *Thrips tabaci*, *Thrips alliorum*, *Thrips hawaiiensis*, *Haplothrips kurdjumovi*, *Chirothrips manicatus*, *Frankliniella intonsa*, *Thrips coloratus*, *Frankliniella occidentalis*, *Thrips palmi*, *Frankliniella lilivora* and *Liothrips vaneeckei*;

the species of the order Acari such as *Leptotrombidium akamushi*, *Tetranychus ludeni*, *Dermacentor variabilis*, *Tetranychus truncatus*, *Ornithonyssus bacoti*, *Demodex canis*, *Tetranychus viennensis*, *Tetranychus kanzawai*, the species of the family Ixodidae such as *Rhipicephalus sanguineus*, *Cheyletus malaccensis*, *Tyrophagus putrescentiae*, *Dermatophagoides farinae*, *Latrodectus hasseltii*, *Dermacentor taiwanensis*, *Acaphylla theavagrans*, *Polyphagotarsonemus latus*, *Aculops lycopersici*, *Ornithonyssus sylvairum*, *Tetranychus urticae*, *Eriophyes chibaensis*, *Sarcoptes scabiei*, *Haemaphysalis longicornis*, *Ixodes scapularis*, *Tyrophagus similis*, *Cheyletus eruditus*, *Panonychus citri*, *Cheyletus moorei*, *Brevipalpus phoenicis*, *Octodectes cynotis*, *Dermatophagoides ptrenyssnus*, *Haemaphysalis flava*, *Ixodes ovatus*, *Phyllocoptruta citri*, *Aculus schlechtendali*, *Panonychus ulmi*, *Amblyomma americanum*, *Dermanyssus gallinae*, *Rhyzoglyphus robini* and *Sancassania* sp.;

the species of the order Isoptera such as *Reticulitermes miyatakei*, *Incisitermes minor*, *Coptotermes formosanus*, *Hodotermopsis japonica*, *Reticulitermes* sp., *Reticulitermes flaviceps amamianus*, *Glyptotermes kushimensis*, *Coptotermes guangzhoensis*, *Neotermes koshunensis*, *Glyptotermes kodamai*, *Glyptotermes satsumensis*, *Cryptotermes domesticus*, *Odontotermes formosanus*, *Glyptotermes nakajimai*, *Pericapritermes nitobei* and *Reticulitermes speratus*;

the species of the order Blattodea such as *Periplaneta fuliginosa*, *Blattella germanica*, *Blatta orientalis*, *Periplaneta brunnea*, *Blattella lituricollis*, *Periplaneta japonica* and *Periplaneta americana*;

the species of the order Siphonaptera such as *Pulex irritans*, *Ctenocephalides felis* and *Ceratophyllus gallinae*;

the species of the phylum Nematoda such as *Nothotylenchus acris*, *Aphelenchoides besseyi*, *Pratylenchus penetrans*, *Meloidogyne hapla*, *Meloidogyne incognita*, *Globodera rostochiensis*, *Meloidogyne javanica*, *Heterodera glycines*, *Pratylenchus coffeae*, *Pratylenchus neglectus* and *Tylenchus semipenetrans*; and the species of the phylum Mollusca such as *Pomacea canaliculata*, *Achatina fulica*, *Meghimatium bilineatum*, *Lehmannina valentiana*, *Limax flavus* and *Acusta despecta sieboldiana*.

In addition, the agricultural or horticultural insecticide of the present invention has a strong insecticidal effect on *Tuta absoluta* as well.

Further, animal-parasitic mites and ticks are also included in the target pests, and the examples include the species of the family Ixodidae such as *Boophilus microplus*, *Rhipicephalus sanguineus*, *Haemaphysalis longicornis*, *Haemaphysalis flava*, *Haemaphysalis campanulata*, *Haemaphysalis concinna*, *Haemaphysalis japonica*, *Haemaphysalis kitaokai*, *Haemaphysalis ias*, *Ixodes ovatus*, *Ixodes nipponensis*, *Ixodes persulcatus*, *Amblyomma testudinarium*, *Haemaphysalis megaspinosa*, *Dermacentor reticulatus* and *Dermacentor taiwanensis*; *Dermanyssus gallinae*; the species of the genus *Ornithonyssus* such as *Ornithonyssus sylviarum* and *Ornithonyssus bursa*; the species of the family Trombiculidae such as *Eutrombicula wichmanni*, *Leptotrombidium akamushi*, *Leptotrombidium pallidum*, *Leptotrombidium fuji*, *Leptotrombidium tosa*, *Neotrombicula autumnalis*, *Eutrombicula alfreddugesi* and *Helenicula miyagawai*; the species of the family Cheyletidae such as *Cheyletiella yasguri*, *Cheyletiella parasitivorax* and *Cheyletiella blakei*; the species of the superfamily Sarcoptoidea such as *Psoroptes cuniculi*, *Chorioptes bovis*, *Otodectes cynotis*, *Sarcoptes scabiei* and *Notoedres cati*; and the species of the family Demodicidae such as *Demodex canis*.

Other target pests include fleas including ectoparasitic wingless insects belonging to the order Siphonaptera, more specifically, the species belonging to the families Pulicidae and Ceratophyllidae. Examples of the species belonging to the family Pulicidae include *Ctenocephalides canis*, *Ctenocephalides felis*, *Pulex irritans*, *Echidnophaga gallinacea*, *Xenopsylla cheopis*, *Leptopsylla segnis*, *Nosopsyllus fasciatus* and *Monopsyllus anisus*.

Other target pests include ectoparasites, for example, the species of the suborder Anoplura such as *Haematopinus eurysternus*, *Haematopinus asini*, *Dalmalinia ovis*, *Linognathus vituli*, *Haematopinus suis*, *Phthirus pubis* and *Pediculus capitis*; the species of the suborder Mallophaga such as *Trichodectes canis*; and hematophagous Dipteran insect pests such as *Tabanus trigonus*, *Culicoides schultzei* and *Simulium ornatum*.

Other target pests include endoparasites, for example, the following endoparasites:

from the order Enoplida, for example, *Trichuris* spp. (whipworms), *Capillaria* spp. (hairworms), *Trichomosoides* spp., *Trichinella* spp. (roundworms), etc.;

from the order Rhabditida, for example, *Micronema* spp., *Strongyloides* spp., etc.;

from the order Strongylida, for example, *Strongylus* spp. (strongyles), *Triodontophorus* spp., *Oesophagodontus* spp., *Trichonema* spp., *Gyalocephalus* spp., *Cylindropharynx* spp., *Poteriostomum* spp., *Cyclococercus* spp., *Cylicostephanus* spp., *Oesophagostomum* spp. (nodule worms), *Chabertia* spp., *Stephanurus* spp. (*Stephanurus dentatus*), *Ancylostoma* spp. (*Ancylostoma duodenale*), *Uncinaria* spp., *Bunostomum* spp., *Globocephalus* spp., *Syngamus* spp., *Cyathostoma* spp., *Metastrongylus* spp. (lungworms), *Dictyocaulus* spp., *Muellerius* spp., *Protostrongylus* spp., *Neostrongylus* spp., *Cystocaulus* spp., *Pneumostrongylus* spp., *Spicocaulus* spp., *Elaphostrongylus* spp., *Parela*-

*phostrongylus* spp., *Crenosoma* spp., *Paracrenosoma* spp., *Angiostrongylus* spp. (*Angiostrongylus cantonensis*), *Aelurostrongylus* spp., *Filaroides* spp., *Parafilaroides* spp., *Trichostrongylus* spp. (*trichostrongyles*), *Haemonchus* spp. (*Haemonchus contortus*), *Ostertagia* spp., *Marshallagia* spp., *Cooperia* spp., *Nematodirus* spp. (*nematodes*), *Hyostrongylus* spp., *Obeliscoides* spp., *Amidostomum* spp., *Ollulanus* spp., etc.;

from the order Oxyurida, for example, *Oxyuris* spp. (*Oxyuris equi*), *Enterobius* spp. (pinworms), *Passalurus* spp., *Syphacia* spp., *Aspiculuris* spp., *Heterakis* spp., etc.;

from the order *Ascaridia*, for example, *Ascaris* spp. (ascarids), *Toxascaris* spp., *Toxocara* spp. (*Toxocara canis*), *Parascaris* spp. (*Parascaris equorum*), *Anisakis* spp., *Ascaridia* spp., etc.;

from the order Spirurida, for example, *Gnathostoma* spp., *Physaloptera* spp., *Thelazia* spp., *Gongylonema* spp., *Habronema* spp., *Parabronema* spp., *Draschia* spp., *Dracunculus* spp. (*Dracunculus medinensis*), etc.;

from the order Filariida, for example, *Stephanofilaria* spp., *Parafilaria* spp., *Setaria* spp., *Loa* spp., *Dirofilaria* spp. (*Dirofilaria immitis*), *Litomosoides* spp., *Brugia* spp., *Wuchereria* spp., *Onchocerca* spp., etc.; and from the order Gigantorhynchida, for example, *Filicollis* spp., *Moniliformis* spp., *Macracanthorhynchus* spp., *Prosthenorchis* spp., etc.

The endoparasite control agent comprising the condensed heterocyclic compound having a bridgehead nitrogen atom represented by the general formula (1) of the present invention or a salt thereof as an active ingredient is effective against not only parasites that live in the body of an intermediate or final host, but also parasites that live in the body of a reservoir host. The compound represented by the general formula (1) of the present invention is effective at every developmental stage of parasites. For example, in the case of protozoa, the compound is effective against their cysts, precystic forms and trophozoites; schizonts and amoeboid forms at the asexual stage; gametocytes, gametes and zygotes at the sexual stage; sporozoites; etc. In the case of nematodes, the compound is effective against their eggs, larvae and adults. The compound of the present invention is capable of not only combating parasites in the living body, but also even preventing parasitic infection by application to the environment as a route of infection. For example, soil-borne infection, i.e., infection from soil of crop fields and parks; percutaneous infection from water in rivers, lakes, marshes, paddy fields, etc.; oral infection from feces of animals such as dogs and cats; oral infection from saltwater fish, freshwater fish, crustaceans, shellfish, raw meat of domestic animals, etc.; infection from mosquitoes, gadflies, flies, cockroaches, mites and ticks, fleas, lice, assassin bugs, trombiculid mites, etc.; and the like can be prevented from occurring.

For the control of ectoparasites or endoparasite in domestic mammals and birds using the compound of the present invention, an effective amount of the compound of the present invention with pharmaceutical excipients can be delivered by oral administration; parenteral administration such as injection (intramuscular, subcutaneous, intravenous, intraperitoneal); transdermal administration such as dipping, spraying, bathing, washing, pouring-on, spotting-on, or dusting; or transnasal administration. For the administration of the compound of the present invention, molded products containing the compound, such as strips, plates, bands, collars, earmarks, limb bands, and label devices, can also be used. The compound of the present invention can be formulated into any dosage form suitable for the administration route selected in administration.

Examples of the dosage form include solid preparations, such as powders, granules, wettable powders, pellets, tablets, bolus, capsules, and molded products containing the active compound; injectable solutions, oral solutions, and solutions for use on the skin or in body cavities; solution preparations, such as pour-on solutions, spot-on solutions, flowables, and emulsions; and semi-solid preparations such as ointments and gels. The solid preparations can be used mainly for oral administration or for transdermal administration after dilution with water, or for environmental treatment.

The solid preparations can be produced by mixing the active compound, and if necessary an adjuvant, with an appropriate filler and then shaping the mixture into a desired form. Examples of the appropriate filler include inorganic substances such as carbonate salts, hydrogen carbonate salts, phosphate salts, aluminum oxide, silica, and clay; and organic substances such as sugar, cellulose, ground cereals, and starch.

The injectable solutions can be administered intravenously, intramuscularly, or subcutaneously. The injectable solutions can be produced by dissolving the active compound in an appropriate solvent, and if necessary, adding excipients such as solubilizing agents, acids, bases, buffer salts, antioxidants, and protecting agents to the solution. Examples of the appropriate solvent include water, ethanol, butanol, benzyl alcohol, glycerin, propylene glycol, polyethylene glycol, N-methyl pyrrolidone, and a mixture thereof, physiologically acceptable vegetable oils, and synthetic oils suitable for injection. Examples of the solubilizing agent include polyvinyl pyrrolidone, polyoxyethylated castor oil, and polyoxyethylated sorbitan ester. Examples of the protecting agent include benzyl alcohol, trichlorobutanol, p-hydroxybenzoic acid ester, and n-butanol.

The oral solutions can be administered directly or after dilution. The oral solutions can be prepared as described above for the injectable solutions.

The flowables, emulsions, and the like can be used, directly or after diluted, for transdermal administration or for environmental treatment.

The solutions for use on the skin can be administered by pouring on, spreading, rubbing in, spraying, dispersing or dipping (dipping, bathing, or washing) or otherwise applying. These solutions can be prepared as described above for the injectable solutions.

The pour-on solutions and spot-on solutions are dripped or sprayed onto a defined area of the skin, and thereby the active compound is allowed to permeate through the skin and act systemically. The pour-on solutions and spot-on solutions can be prepared by dissolving, suspending, or emulsifying the active ingredient in an appropriate solvent or mixed solvent suitable for use on the skin. If necessary, an adjuvant such as a surfactant, a colorant, an absorption enhancer, an antioxidant, a light stabilizer, and/or an adhesive may be contained. Examples of the solvent include water, alkanol, glycol, polyethylene glycol, polypropylene glycol, glycerin, benzyl alcohol, phenylethanol, phenoxyethanol, ethyl acetate, butyl acetate, benzyl benzoate, dipropylene glycol monomethyl ether, diethylene glycol monobutyl ether, acetone, methyl ethyl ketone, aromatic and/or aliphatic hydrocarbons, vegetable or synthetic oils, DMF, liquid paraffin, light liquid paraffin, silicone, dimethylacetamide, N-methyl pyrrolidone, and 2,2-dimethyl-4-oxymethylene-1,3-dioxolane. Examples of the absorption enhancer include dimethyl sulfoxide (DMSO), isopropyl myristate, dipropylene glycol pelargonate, silicone oil, aliphatic ester, triglyceride, and fatty alcohol. Examples of the antioxidant include sulfite salts, metabisulfite salts, ascorbic acid, butylated hydroxytoluene, butylated hydroxyanisole, and tocopherol.

The emulsions can be delivered by oral administration, transdermal administration, or injection. The emulsions can be prepared by dissolving the active ingredient in a hydrophobic or hydrophilic phase and homogenizing the solution with the other phase solvent with the addition of an appropriate emulsifier and if necessary an adjuvant such as a colorant, an absorption enhancer, a protecting agent, an antioxidant, a light-shielding agent, and/or a thickener.

Examples of the hydrophobic phase (oil) include paraffin oil, silicone oil, sesame oil, almond oil, castor oil; synthetic triglycerides; esters such as ethyl stearate, di-n-butyryl adipate, hexyl laurate, dipropylene glycol pelargonate, esters of branched short-chain fatty acids and saturated $C_{16}$-$C_{18}$ fatty acids, isopropyl myristate, isopropyl palmitate, caprylic or capric acid esters of saturated $C_{12}$-$C_{18}$ aliphatic alcohols, isopropyl stearate, oleyl oleate, decyl oleate, ethyl oleate, ethyl lactate, waxy fatty acid ester, dibutyl phthalate, and diisopropyl adipate; and alcohols such as isotridecyl alcohol, 2-octyldodecanol, cetyl stearyl alcohol, and oleyl alcohol.

Examples of the hydrophilic phase include water, propylene glycol, glycerin, and sorbitol.

Examples of the emulsifier include nonionic surfactants such as polyoxyethylated castor oil, polyoxyethylated sorbitan monoolefinate, sorbitan monostearate, glyceryl monostearate, polyoxyethyl stearate, and alkylphenol polyglycol ether; amphoteric surfactants such as disodium N-lauryl β-iminodipropionate and lecithin; anionic surfactants such as sodium lauryl sulfate, fatty alcohol ether sulfate, and monoethanolamine salts of mono-/di-alkyl polyglycol orthophosphoric acid ester; and cationic surfactants such as cetyltrimethylammonium chloride.

Other adjuvants include carboxymethyl cellulose, methyl cellulose, polyacrylate, alginate, gelatin, gum arabic, polyvinyl pyrrolidone, polyvinyl alcohol, methyl vinyl ether, maleic anhydride copolymers, polyethylene glycol, waxes, and colloidal silica.

The semi-solid preparations can be administered by applying or spreading them on the skin or introducing them into body cavities. The gels can be prepared by preparing a solution as described above for the injectable solutions and adding, to the solution, a thickener in an amount sufficient to give a clear, ointment-like, viscous substance.

In the case where the endoparasite control agent of the present invention is used as a pharmaceutical for animals of non-human mammalian or avian species, the optimum amount (effective amount) of the active ingredient varies with the purpose (treatment or prevention), the kind of infectious parasite, the type and severity of infection, the dosage form, etc., but in general, the oral daily dose is in the range of about 0.0001 to 10000 mg/kg body weight and the parenteral daily dose is in the range of about 0.0001 to 10000 mg/kg body weight. Such a dose may be given as a single dose or in divided doses.

The concentration of the active ingredient in the endoparasite control agent of the present invention is generally about 0.001 to 100% by mass, preferably about 0.001 to 99% by mass, and more preferably about 0.005 to 20% by mass. The endoparasite control agent of the present invention may be a composition that can be directly administered, or a highly concentrated composition that needs to be diluted to a suitable concentration before use.

The endoparasite control agent of the present invention can be used in combination with any existing endoparasite control agent for the purpose of reinforcing or complementing its effect. In such a combined use, two or more active ingredients may be mixed and formulated into a single preparation before administration, or two or more different preparations may be administered separately.

The agricultural or horticultural insecticide comprising the condensed heterocyclic compound having a bridgehead nitrogen atom represented by the general formula (1) of the present invention or a salt thereof as an active ingredient has a remarkable control effect on the above-described pests which damage lowland crops, field crops, fruit trees, vegetables, other crops, ornamental flowering plants, etc. The desired effect can be obtained when the agricultural or horticultural insecticide is applied to nursery facilities for seedlings, paddy fields, fields, fruit trees, vegetables, other crops, ornamental flowering plants, etc. and their seeds, paddy water, foliage, cultivation media such as soil, or the like around the expected time of pest infestation, i.e., before the infestation or upon the confirmation of the infestation. In particularly preferable embodiments, the application of the agricultural or horticultural insecticide utilizes so-called penetration and translocation. That is, nursery soil, soil in transplanting holes, plant foot, irrigation water, cultivation water in hydroponics, or the like is treated with the agricultural or horticultural insecticide to allow crops, ornamental flowering plants, etc. to absorb the compound of the present invention through the roots via soil or otherwise.

Examples of useful plants to which the agricultural or horticultural insecticide of the present invention can be applied include, but are not particularly limited to, cereals (e.g., rice, barley, wheat, rye, oats, corn, etc.), legumes (e.g., soybeans, azuki beans, broad beans, green peas, kidney beans, peanuts, etc.), fruit trees and fruits (e.g., apples, citrus fruits, pears, grapes, peaches, plums, cherries, walnuts, chestnuts, almonds, bananas, etc.), leaf and fruit vegetables (e.g., cabbages, tomatoes, spinach, broccoli, lettuce, onions, green onions (chives, Welsh onions, etc.), green peppers, eggplants, strawberries, pepper crops, okra, Chinese chives, etc.), root vegetables (e.g., carrots, potatoes, sweet potatoes, taros, Japanese radishes, turnips, lotus roots, burdock roots, garlic, Chinese scallions, etc.), crops for processing (e.g., cotton, hemp, beet, hops, sugarcane, sugar beet, olives, rubber, coffee, tobacco, tea, etc.), gourds (e.g., Japanese pumpkins, cucumbers, watermelons, oriental sweet melons, melons, etc.), pasture grass (e.g., orchardgrass, sorghum, timothy, clover, alfalfa, etc.), lawn grass (e.g., Korean lawn grass, bent grass, etc.), spice and aromatic crops and ornamental crops (e.g., lavender, rosemary, thyme, parsley, pepper, ginger, etc.), ornamental flowering plants (e.g., chrysanthemum, rose, carnation, orchid, tulip, lily, etc.), garden trees (e.g., ginkgo trees, cherry trees, Japanese aucuba, etc.) and forest trees (e.g., *Abies sachalinensis, Picea jezoensis*, pine, yellow cedar, Japanese cedar, hinoki cypress, eucalyptus, etc.).

The above-mentioned "plants" also include plants provided with herbicide tolerance by a classical breeding technique or a gene recombination technique. Examples of such herbicide tolerance include tolerance to HPPD inhibitors, such as isoxaflutole; ALS inhibitors, such as imazethapyr and thifensulfuron-methyl; EPSP synthase inhibitors, such as glyphosate; glutamine synthetase inhibitors, such as glufosinate; acetyl-CoA carboxylase inhibitors, such as sethoxydim; or other herbicides, such as bromoxynil, dicamba and 2,4-D.

Examples of the plants provided with herbicide tolerance by a classical breeding technique include varieties of rapeseed, wheat, sunflower and rice tolerant to the imidazolinone family of ALS-inhibiting herbicides such as imazethapyr, and such plants are sold under the trade name of Clearfield (registered trademark). Also included is a variety of soybean provided with tolerance to the sulfonyl urea family of ALS-inhibiting herbicides such as thifensulfuron-methyl by a classical breeding technique, and this is sold under the trade name of STS soybean. Also included are plants provided with tolerance to acetyl-CoA carboxylase inhibitors such as trione oxime herbicides and aryloxy phenoxy propionic acid herbicides by a classical breeding technique, for example, SR corn and the like.

Plants provided with tolerance to acetyl-CoA carboxylase inhibitors are described in Proc. Natl. Acad. Sci. USA, 87, 7175-7179 (1990), and the like. Further, acetyl-CoA carboxylase mutants resistant to acetyl-CoA carboxylase inhibitors are reported in Weed Science, 53, 728-746 (2005), and the like, and by introducing the gene of such an acetyl-CoA carboxylase mutant into plants by a gene recombination technique, or introducing a resistance-conferring mutation into acetyl-CoA carboxylase of plants, plants tolerant to acetyl-CoA carboxylase inhibitors can be engineered. Alternatively, by introducing a nucleic acid causing base substitution mutation into plant cells (a typical example of this technique is chimeraplasty technique (Gura T. 1999. Repairing the Genome's Spelling Mistakes. Science 285: 316-318.)) to allow site-specific substitution mutation in the amino acids encoded by an acetyl-CoA carboxylase gene, an ALS gene or the like of plants, plants tolerant to acetyl-CoA carboxylase inhibitors, ALS inhibitors or the like can be engineered. The agricultural or horticultural insecticide of the present invention can be applied to these plants as well.

Further, exemplary toxins expressed in genetically modified plants include insecticidal proteins of *Bacillus cereus* or *Bacillus popilliae; Bacillus thuringiensis* δ-endotoxins, such as Cry1Ab, Cry1Ac, Cry1F, Cry1Fa2, Cry2Ab, Cry3A, Cry3Bb1 and Cry9C, and other insecticidal proteins, such as VIP1, VIP2, VIP3 and VIP3A; nematode insecticidal proteins; toxins produced by animals, such as scorpion toxins, spider toxins, bee toxins and insect-specific neurotoxins; toxins of filamentous fungi; plant lectins; agglutinin; protease inhibitors, such as trypsin inhibitors, serine protease inhibitors, patatin, cystatin and papain inhibitors; ribosome inactivating proteins (RIP), such as ricin, maize RIP, abrin, luffin, saporin and bryodin; steroid metabolizing enzymes, such as 3-hydroxy steroid oxidase, ecdysteroid-UDP-glucosyltransferase and cholesterol oxidase; ecdysone inhibitors; HMG-CoA reductase; ion channel inhibitors, such as sodium channel inhibitors and calcium channel inhibitors; juvenile hormone esterase; diuretic hormone receptors; stilbene synthase; bibenzyl synthase; chitinase; and glucanase.

Also included are hybrid toxins, partially deficient toxins and modified toxins derived from the following: δ-endotoxin proteins such as Cry1Ab, Cry1Ac, Cry1F, Cry1Fa2, Cry2Ab, Cry3A, Cry3Bb1, Cry9C, Cry34Ab and Cry35Ab, and other insecticidal proteins such as VIP1, VIP2, VIP3 and VIP3A. The hybrid toxin can be produced by combining some domains of these proteins differently from the original combination in nature with the use of a recombination technique. As the partially deficient toxin, a Cry1Ab toxin in which a part of the amino acid sequence is deleted is known. In the modified toxin, one or more amino acids of a naturally occurring toxin are substituted.

Examples of the foregoing toxins and genetically modified plants capable of synthesizing these toxins are described in EP0374753A, WO93/07278, WO95/34656, EP0427529A, EP451878A, WO03/052073, etc.

Due to the toxins contained in such genetically modified plants, the plants exhibit resistance to pests, in particular, Coleopteran insect pests, Hemipteran insect pests, Dipteran insect pests, Lepidopteran insect pests and nematodes. The above-described technologies and the agricultural or horticultural insecticide of the present invention can be used in combination or used systematically.

In order to control target pests, the agricultural or horticultural insecticide of the present invention, with or without appropriate dilution or suspension in water etc., is applied to plants potentially infested with the target insect pests or nematodes in an amount effective for the control of the insect pests or nematodes. For example, in order to control insect pests and nematodes that may damage crop plants such as fruit trees, cereals and vegetables, foliar application and seed treatment such as dipping, dust coating and calcium peroxide coating can be performed. Further, treatment of soil or the like may also be performed to allow plants to absorb agrochemicals through their roots. Examples of such treatment include whole soil incorporation, planting row treatment, bed soil incorporation, plug seedling treatment, planting hole treatment, plant foot treatment, top-dressing, treatment of nursery boxes for paddy rice, and submerged application. In addition, application to culture media in hydroponics, smoking treatment, trunk injection and the like can also be performed.

Further, the agricultural or horticultural insecticide of the present invention, with or without appropriate dilution or suspension in water etc., can be applied to sites potentially infested with pests in an amount effective for the control of the pests. For example, it can be directly applied to stored grain pests, house pests, sanitary pests, forest pests, etc., and also be used for coating of residential building materials, for smoking treatment, or as a bait formulation.

Exemplary methods of seed treatment include dipping of seeds in a diluted or undiluted fluid of a liquid or solid formulation for the permeation of agrochemicals into the seeds; mixing or dust coating of seeds with a solid or liquid formulation for the adherence of the formulation onto the surfaces of the seeds; coating of seeds with a mixture of an agrochemical and an adhesive carrier such as resins and polymers; and application of a solid or liquid formulation to the vicinity of seeds at the same time as seeding.

The term "seed" in the above-mentioned seed treatment refers to a plant body which is in the early stages of cultivation and used for plant propagation. The examples include, in addition to a so-called seed, a plant body for vegetative propagation, such as a bulb, a tuber, a seed potato, a bulbil, a propagule, a discoid stem and a stem used for cuttage.

The term "soil" or "cultivation medium" in the method of the present invention for using an agricultural or horticultural insecticide refers to a support medium for crop cultivation, in particular a support medium which allows crop plants to spread their roots therein, and the materials are not particularly limited as long as they allow plants to grow. Examples of the support medium include what is called soils, seedling mats and water, and specific examples of the materials include sand, pumice, vermiculite, diatomite, agar, gelatinous substances, high-molecular-weight substances, rock wool, glass wool, wood chip and bark.

Exemplary methods of the application to crop foliage or to stored grain pests, house pests, sanitary pests, forest pests, etc. include application of a liquid formulation, such as an emulsifiable concentrate and a flowable, or a solid formulation, such as a wettable powder and a water-dispersible granule, after appropriate dilution in water; dust application; and smoking.

Exemplary methods of soil application include application of a water-diluted or undiluted liquid formulation to the foot of plants, nursery beds for seedlings, or the like; application of a granule to the foot of plants, nursery beds for seedlings, or the like; application of a dust, a wettable powder, a water-dispersible granule, a granule or the like onto soil and subsequent incorporation of the formulation into the whole soil before seeding or transplanting; and application of a dust, a wettable powder, a water-dispersible granule, a granule or the like to planting holes, planting rows or the like before seeding or planting.

To nursery boxes for paddy rice, for example, a dust, a water-dispersible granule, a granule or the like can be applied, although the suitable formulation may vary depending on the application timing, in other words, depending on the cultivation stage such as seeding time, greening period and planting time. A formulation such as a dust, a water-dispersible granule and a granule may be mixed with nursery soil. For example, such a formulation is incorporated into bed soil, covering soil or the whole soil. Simply, nursery soil and such a formulation may be alternately layered.

In the application to paddy fields, a solid formulation, such as a jumbo, a pack, a granule and a water-dispersible granule, or a liquid formulation, such as a flowable and an emulsifiable concentrate, is applied usually to flooded paddy fields. In a rice planting period, a suitable formulation, as it is or after mixed with a fertilizer, may be applied onto soil or injected into soil. In addition, an emulsifiable concentrate, a flowable or the like may be applied to the source of water supply for paddy fields, such as a water inlet and an irrigation device. In this case, treatment can be accomplished with the supply of water and thus achieved in a labor-saving manner.

In the case of field crops, their seeds, cultivation media in the vicinity of their plants, or the like may be treated with the agricultural or horticultural insecticide of the present invention in the period of seeding to seedling culture. In the case of plants of which the seeds are directly sown in the field, in addition to direct seed treatment, plant foot treatment during cultivation is preferable. Specifically, the treatment can be performed by, for example, applying a granule onto soil, or drenching soil with a formulation in a water-diluted or undiluted liquid form. Another preferable treatment is incorporation of a granule into cultivation media before seeding.

In the case of culture plants to be transplanted, preferable examples of the treatment in the period of seeding to seedling culture include, in addition to direct seed treatment, drench treatment of nursery beds for seedlings with a formulation in a liquid form; and granule application to nursery beds for seedlings. Also included are treatment of planting holes with a granule; and incorporation of a granule into cultivation media in the vicinity of planting points at the time of fix planting.

The agricultural or horticultural insecticide of the present invention is commonly used as a formulation convenient for application, which is prepared by the usual method for preparing agrochemical formulations.

That is, the condensed heterocyclic compound having a bridgehead nitrogen atom represented by the general formula (1) of the present invention or a salt thereof and an appropriate inactive carrier, and if needed an adjuvant, are blended at an appropriate ratio, and through the step of dissolution, separation, suspension, mixing, impregnation, adsorption and/or adhesion, are formulated into an appropriate form for application, such as a suspension concentrate, an emulsifiable concentrate, a soluble concentrate, a wettable powder, a water-dispersible granule, a granule, a dust, a tablet and a pack.

The composition (agricultural or horticultural insecticide or animal ectoparasite or endoparasite control agent) of the present invention can optionally contain an additive usually used for agrochemical formulations or animal parasite control agents in addition to the active ingredient. Examples of the additive include carriers such as solid or liquid carriers, surfactants, dispersants, wetting agents, binders, tackifiers, thickeners, colorants, spreaders, sticking/spreading agents, antifreezing agents, anti-caking agents, disintegrants and stabilizing agents. If needed, preservatives, plant fragments, etc. may also be used as the additive. One of these additives may be used alone, and also two or more of them may be used in combination.

Examples of the solid carriers include natural minerals, such as quartz, clay, kaolinite, pyrophyllite, sericite, talc, bentonite, acid clay, attapulgite, zeolite and diatomite; inorganic salts, such as calcium carbonate, ammonium sulfate, sodium sulfate and potassium chloride; organic solid carriers, such as synthetic silicic acid, synthetic silicates, starch, cellulose and plant powders (for example, sawdust, coconut shell, corn cob, tobacco stalk, etc.); plastics carriers, such as polyethylene, polypropylene and polyvinylidene chloride; urea; hollow inorganic materials; hollow plastic materials; and fumed silica (white carbon). One of these solid carriers may be used alone, and also two or more of them may be used in combination.

Examples of the liquid carriers include alcohols including monohydric alcohols, such as methanol, ethanol, propanol, isopropanol and butanol, and polyhydric alcohols, such as ethylene glycol, diethylene glycol, propylene glycol, hexylene glycol, polyethylene glycol, polypropylene glycol and glycerin; polyol compounds, such as propylene glycol ether; ketones, such as acetone, methyl ethyl ketone, methyl isobutyl ketone, diisobutyl ketone and cyclohexanone; ethers, such as ethyl ether, dioxane, ethylene glycol monoethyl ether, dipropyl ether and tetrahydrofuran; aliphatic hydrocarbons, such as normal paraffin, naphthene, isoparaffin, kerosene and mineral oil; aromatic hydrocarbons, such as benzene, toluene, xylene, solvent naphtha and alkyl naphthalene; halogenated hydrocarbons, such as dichloromethane, chloroform and carbon tetrachloride; esters, such as ethyl acetate, diisopropyl phthalate, dibutyl phthalate, dioctyl phthalate and dimethyl adipate; lactones, such as γ-butyrolactone; amides, such as dimethylformamide, diethylformamide, dimethylacetamide and N-alkyl pyrrolidinone; nitriles, such as acetonitrile; sulfur compounds, such as dimethyl sulfoxide; vegetable oils, such as soybean oil, rapeseed oil, cotton seed oil and castor oil; and water. One of these liquid carriers may be used alone, and also two or more of them may be used in combination.

Exemplary surfactants used as the dispersant or the wetting/spreading agent include nonionic surfactants, such as sorbitan fatty acid ester, polyoxyethylene sorbitan fatty acid ester, sucrose fatty acid ester, polyoxyethylene fatty acid ester, polyoxyethylene resin acid ester, polyoxyethylene fatty acid diester, polyoxyethylene alkyl ether, polyoxyethylene alkyl aryl ether, polyoxyethylene alkyl phenyl ether, polyoxyethylene dialkyl phenyl ether, polyoxyethylene alkyl phenyl ether-formaldehyde condensates, polyoxyethylene-polyoxypropylene block copolymers, polystyrene-polyoxyethylene block polymers, alkyl polyoxyethylene-polypropylene block copolymer ether, polyoxyethylene alkylamine, polyoxyethylene fatty acid amide, polyoxyethylene fatty acid bis(phenyl ether), polyalkylene benzyl phenyl ether, polyoxyalkylene styryl phenyl ether, acetylene diol, polyoxyalkylene-added acetylene diol, polyoxyethylene ether-type silicone, ester-type silicone, fluorosurfactants, polyoxyethylene castor oil and polyoxyethylene hydrogenated castor oil; anionic surfactants, such as alkyl sulfates, polyoxyethylene alkyl ether sulfates, polyoxyethylene alkyl phenyl ether sulfates, polyoxyethylene styryl phenyl ether sulfates, alkylbenzene sulfonates, alkylaryl sulfonates, lignosulfonates, alkyl sulfosuccinates, naphthalene sulfonates, alkylnaphthalene sulfonates, salts of naphthalenesulfonic acid-formaldehyde condensates, salts of alkylnaphthalenesulfonic acid-formaldehyde condensates, fatty acid salts, polycarboxylic acid salts, polyacrylates, N-methyl-fatty acid sarcosinates, resinates, polyoxyethylene alkyl ether phosphates and polyoxyethylene alkyl phenyl ether phosphates; cationic surfactants including alkyl amine salts, such as lauryl amine hydrochloride, stearyl amine hydrochloride, oleyl amine hydrochloride, stearyl amine acetate, stearyl aminopropyl amine acetate, alkyl trimethyl ammonium chloride and alkyl dimethyl benzalkonium chloride; and amphoteric surfactants, such as amino acid-type or betaine-type amphoteric surfactants. One of these surfactants may be used alone, and also two or more of them may be used in combination.

Examples of the binders or the tackifiers include carboxymethyl cellulose or salts thereof, dextrin, soluble starch, xanthan gum, guar gum, sucrose, polyvinyl pyrrolidone, gum arabic, polyvinyl alcohol, polyvinyl acetate, sodium polyacrylate, polyethylene glycols with an average molecular weight of 6,000 to 20,000, polyethylene oxides with an average molecular weight of 100,000 to 5,000,000, phospholipids (for example, cephalin, lecithin, etc.), cellulose powder, dextrin, modified starch, polyaminocarboxylic acid chelating compounds, cross-linked polyvinyl pyrrolidone, maleic acid-styrene copolymers, (meth)acrylic acid copolymers, half esters of polyhydric alcohol polymer and dicarboxylic anhydride, water soluble polystyrene sulfonates, paraffin, terpene, polyamide resins, polyacrylates, polyoxyethylene, waxes, polyvinyl alkyl ether, alkylphenol-formaldehyde condensates and synthetic resin emulsions.

Examples of the thickeners include water soluble polymers, such as xanthan gum, guar gum, diutan gum, carboxymethyl cellulose, polyvinyl pyrrolidone, carboxyvinyl polymers, acrylic polymers, starch compounds and polysaccharides; and inorganic fine powders, such as high grade bentonite and fumed silica (white carbon).

Examples of the colorants include inorganic pigments, such as iron oxide, titanium oxide and Prussian blue; and organic dyes, such as alizarin dyes, azo dyes and metal phthalocyanine dyes.

Examples of the antifreezing agents include polyhydric alcohols, such as ethylene glycol, diethylene glycol, propylene glycol and glycerin.

Examples of the adjuvants serving to prevent caking or facilitate disintegration include polysaccharides (starch, alginic acid, mannose, galactose, etc.), polyvinyl pyrrolidone, fumed silica (white carbon), ester gum, petroleum resin, sodium tripolyphosphate, sodium hexametaphosphate, metal stearates, cellulose powder, dextrin, methacrylate copolymers, polyvinyl pyrrolidone, polyaminocarboxylic acid chelating compounds, sulfonated styrene-isobutylene-maleic anhydride copolymers and starch-polyacrylonitrile graft copolymers.

Examples of the stabilizing agents include desiccants, such as zeolite, quicklime and magnesium oxide; antioxidants, such as phenolic compounds, amine compounds, sulfur compounds and phosphoric acid compounds; and ultraviolet absorbers, such as salicylic acid compounds and benzophenone compounds.

Examples of the preservatives include potassium sorbate and 1,2-benzothiazolin-3-one.

Further, other adjuvants including functional spreading agents, activity enhancers such as metabolic inhibitors (piperonyl butoxide etc.), antifreezing agents (propylene glycol etc.), antioxidants (BHT etc.) and ultraviolet absorbers can also be used if needed.

The amount of the active ingredient compound in the agricultural or horticultural insecticide of the present invention can be adjusted as needed, and basically, the amount of the active ingredient compound is appropriately selected from the range of 0.01 to 90 parts by weight in 100 parts by weight of the agricultural or horticultural insecticide. For example, in the case where the agricultural or horticultural insecticide is a dust, a granule, an emulsifiable concentrate or a wettable powder, it is suitable that the amount of the active ingredient compound is 0.01 to 50 parts by weight (0.01 to 50% by weight relative to the total weight of the agricultural or horticultural insecticide).

The application rate of the agricultural or horticultural insecticide of the present invention may vary with various factors, for example, the purpose, the target pest, the growing conditions of crops, the tendency of pest infestation, the weather, the environmental conditions, the dosage form, the application method, the application site, the application timing, etc., but basically, the application rate of the active ingredient compound is appropriately selected from the range of 0.001 g to 10 kg, and preferably 0.01 g to 1 kg per 10 ares depending on the purpose.

Furthermore, for the expansion of the range of target pests and the appropriate time for pest control, or for dose reduction, the agricultural or horticultural insecticide of the present invention can be used after mixed with other agricultural or horticultural insecticides, acaricides, nematicides, microbicides, biopesticides and/or the like. Further, the agricultural or horticultural insecticide can be used after mixed with herbicides, plant growth regulators, fertilizers and/or the like depending on the situation.

Examples of such additional agricultural or horticultural insecticides, acaricides and nematicides used for the above-mentioned purposes include 3,5-xylyl methylcarbamate (XMC), crystalline protein toxins produced by *Bacillus thuringiensis* such as *Bacillus thuringiensis aizawai*, *Bacillus thuringiensis israelensis*, *Bacillus thuringiensis japonensis*, *Bacillus thuringiensis kurstaki* and *Bacillus thuringiensis* tenebrionis, BPMC, Bt toxin-derived insecticidal compounds, CPCBS (chlorfenson), DCIP (dichlorodiisopropyl ether), D-D (1,3-dichloropropene), DDT, NAC, O-4-dimethylsulfamoylphenyl O,O-diethyl phosphorothioate (DSP), O-ethyl O-4-nitrophenyl phenylphosphonothioate (EPN), tripropylisocyanurate (TPIC), acrinathrin, azadirachtin, azinphos-methyl, acequinocyl, acetamiprid, acetoprole, acephate, abamectin, avermectin-B, amidoflumet, amitraz, alanycarb, aldicarb, aldoxycarb, aldrin, alpha-endosulfan, alpha-cypermethrin, albendazole, allethrin, isazofos, isamidofos, isoamidofos isoxathion, isofenphos, isoprocarb (MIPC), ivermectin, imicyafos, imidacloprid, imiprothrin, indoxacarb, esfenvalerate, ethiofencarb, ethion, ethiprole, etoxazole, ethofenprox, ethoprophos, etrimfos, emamectin, emamectin-benzoate, endosulfan, empenthrin, oxamyl, oxydemeton-methyl, oxydeprofos (ESP), oxibendazole, oxfendazole, potassium oleate, sodium oleate, cadusafos, cartap, carbaryl, carbosulfan, carbofuran, gamma-cyhalothrin, xylylcarb, quinalphos, kinoprene, chinomethionat, cloethocarb, clothianidin, clofentezine, chromafenozide, chlorantraniliprole, chlorethoxyfos, chlordimeform, chlordane, chlorpyrifos, chlorpyrifos-methyl, chlorphenapyr, chlorfenson, chlorfenvinphos, chlorfluazuron, chlorobenzilate, chlorobenzoate, kelthane (dicofol), salithion, cyanophos (CYAP), diafenthiuron, diamidafos, cyantraniliprole, theta-cypermethrin, dienochlor, cyenopyrafen, dioxabenzofos, diofenolan, sigma-cypermethrin, dichlofenthion (ECP), cycloprothrin, dichlorvos (DDVP), disulfoton, dinotefuran, cyhalothrin, cyphenothrin, cyfluthrin, diflubenzuron, cyflumetofen, diflovidazin, cyhexatin, cypermethrin, dimethylvinphos, dimethoate, dimefluthrin, silafluofen, cyromazine, spinetoram, spinosad, spirodiclofen, spirotetramat, spiromesifen, sulfluramid, sulprofos, sulfoxaflor, zeta-cypermethrin, diazinon, tau-fluvalinate, dazomet, thiacloprid, thiamethoxam, thiodicarb, thiocyclam, thiosultap, thiosultap-sodium, thionazin, thiometon, deet, dieldrin, tetrachlorvinphos, tetradifon, tetramethylfluthrin, tetramethrin, tebupirimfos, tebufenozide, tebufenpyrad, tefluthrin, teflubenzuron, demeton-S-methyl, temephos, deltamethrin, terbufos, tralopyril, tralomethrin, transfluthrin, triazamate, triazuron, trichlamide, trichlorphon (DEP), triflumuron, tolfenpyrad, naled (BRP), nithiazine, nitenpyram, novaluron, noviflumuron, hydroprene, vaniliprole, vamidothion, parathion, parathion-methyl, halfenprox, halofenozide, bistrifluron, bisultap, hydramethylnon, hydroxy propyl starch, binapacryl, bifenazate, bifenthrin, pymetrozine, pyraclofos, pyrafluprole, pyridafenthion, pyridaben, pyridalyl, pyrifluquinazon, pyriprole, pyriproxyfen, pirimicarb, pyrimidifen, pirimiphos-methyl, pyrethrins, fipronil, fenazaquin, fenamiphos, bromopropylate, fenitrothion (MEP), fenoxycarb, fenothiocarb, phenothrin, fenobucarb, fensulfothion, fenthion (MPP), phenthoate (PAP), fenvalerate, fenpyroximate, fenpropathrin, fenbendazole, fosthiazate, butathiofos, buprofezin, furathiocarb, prallethrin, fluacrypyrim, fluazinam, fluazuron, fluensulfone, flucycloxuron, flucythrinate, fluvalinate, flupyrazofos, flufenerim, flufenoxuron, flufenzine, flufenprox, fluproxyfen, flubrocythrinate, flubendiamide, flumethrin, flurimfen, prothiofos, protrifenbute, flonicamid, propaphos, propargite (BPPS), profenofos, profluthrin, propoxur (PHC), bromopropylate, beta-cyfluthrin, hexaflumuron, hexythiazox, heptenophos, permethrin, benclothiaz, bendiocarb, bensultap, benzoximate, benfuracarb, phoxim, phosalone, fosthiazate, fosthietan, phosphamidon, phosphocarb, phosmet (PMP), polynactins, formetanate, formothion, phorate, machine oil, malathion, milbemycin, milbemycin-A, milbemectin, mecarbam, mesulfenfos, methomyl, metaldehyde, metaflumizone, methamidophos, metam-ammonium, metam-sodium, methiocarb, methidathion (DMTP), methylisothiocyanate, methylneodecanamide, methylparathion, metoxadiazone, methoxychlor, methoxyfenozide, metofluthrin, methoprene, metolcarb, meperfluthrin, mevinphos, monocrotophos, monosultap, lambda-cyhalothrin, ryanodine, lufenuron, resmethrin, lepimectin, rotenone, levamisole hydrochloride, fenbutatin oxide, morantel tartarate, methyl bromide, tricyclohexyltin hydroxide (cyhexatin), calcium cyanamide, calcium polysulfide, sulfur and nicotine-sulfate.

Exemplary agricultural or horticultural microbicides used for the same purposes as above include aureofungin, azaconazole, azithiram, acypetacs, acibenzolar, acibenzolar-S-methyl, azoxystrobin, anilazine, amisulbrom, ampropylfos, ametoctradin, allyl alcohol, aldimorph, amobam, isotianil, isovaledione, isopyrazam, isoprothiolane, ipconazole, iprodione, iprovalicarb, iprobenfos, imazalil, iminoctadine, iminoctadine-albesilate, iminoctadine-triacetate, imibenconazole, uniconazole, uniconazole-P, echlomezole, edifenphos, etaconazole, ethaboxam, ethirimol, etem, ethoxyquin, etridiazole, enestroburin, epoxiconazole, oxadixyl, oxycarboxin, copper-8-quinolinolate, oxytetracycline, copper-oxinate, oxpoconazole, oxpoconazole-fumarate, oxolinic acid, octhilinone, ofurace, orysastrobin, metam-sodium, kasugamycin, carbamorph, carpropamid, carbendazim, carboxin, carvone, quinazamid, quinacetol, quinoxyfen, quinomethionate, captafol, captan, kiralaxyl, quinconazole, quintozene, guazatine, cufraneb, cuprobam, glyodin, griseofulvin, climbazole, cresol, kresoxim-methyl, chlozolinate, clotrimazole, chlobenthiazone, chloraniformethan, chloranil, chlorquinox, chloropicrin, chlorfenazole, chlorodinitronaphthalene, chlorothalonil, chloroneb, zarilamid, salicylanilide, cyazofamid, diethyl pyrocarbonate, diethofencarb, cyclafuramid, diclocymet, dichlozoline, diclobutrazol, dichlofluanid, cycloheximide, diclomezine, dicloran, dichlorophen, dichlone, disulfiram, ditalimfos, dithianon, diniconazole, diniconazole-M, zineb, dinocap, dinocton, dinosulfon, dinoterbon, dinobuton, dinopenton, dipyrithione, diphenylamine, difenoconazole, cyflufenamid, diflumetorim, cyproconazole, cyprodinil, cyprofuram, cypendazole, simeconazole, dimethirimol, dimethomorph, cymoxanil, dimoxystrobin, methyl bromide, ziram, silthiofam, streptomycin, spiroxamine, sultropen, sedaxane, zoxamide, dazomet, thiadiazin, tiadinil, thiadifluor, thiabendazole, tioxymid, thiochlorfenphim, thiophanate, thiophanate-methyl, thicyofen, thioquinox, chinomethionat, thifluzamide, thiram, decafentin, tecnazene, tecloftalam, tecoram, tetraconazole, debacarb, dehydroacetic acid, tebuconazole, tebufloquin, dodicin, dodine, dodecyl benzensulfonate bis-ethylene diamine copper(II) (DBEDC), dodemorph, drazoxolon, triadimenol, triadimefon, triazbutil, triazoxide, triamiphos, triarimol, trichlamide, tricyclazole, triticonazole, tridemorph, tributyltin oxide, triflumizole, trifloxystrobin, triforine, tolylfluanid, tolclofos-methyl, natamycin, nabam, nitrothal-isopropyl, nitrostyrene, nuarimol, copper nonylphenol sulfonate, halacrinate, validamycin, valifenalate, harpin protein, bixafen, picoxystrobin, picobenzamide, bithionol, bitertanol, hydroxyisoxazole, hydroxyisoxazole-potassium, binapacryl, biphenyl, piperalin, hymexazol, pyraoxystrobin, pyracarbolid, pyraclostrobin, pyrazophos, pyrametostrobin, pyriofenone, pyridinitril, pyrifenox, pyribencarb, pyrimethanil, pyroxychlor, pyroxyfur, pyroquilon, vinclozolin, famoxadone, fenapanil, fenamidone, fenaminosulf, fenarimol, fenitropan, fenoxanil, ferimzone, ferbam, fentin, fenpiclonil, fenpyrazamine, fenbuconazole, fenfuram, fenpropidin, fenpropimorph, fenhexamid, phthalide, buthiobate, butylamine, bupirimate, fuberidazole, blasticidin-S, furametpyr, furalaxyl, fluacrypyrim, fluazinam, fluoxastrobin, fluotrimazole, fluopicolide, fluopyram, fluoroimide, furcarbanil, fluxapyroxad, fluquinconazole, furconazole, furconazole-cis, fludioxonil, flusilazole, flusulfamide, flutianil, flutolanil, flutriafol, furfural, furmecyclox, flumetover, flumorph, proquinazid, prochloraz, procymidone, prothiocarb, prothioconazole, propamocarb, propiconazole, propineb, furophanate, probenazole, bromuconazole, hexachlorobutadiene, hexaconazole, hexylthiofos, bethoxazin, benalaxyl, benalaxyl-M, benodanil, benomyl, pefurazoate, benquinox, penconazole, benzamorf, pencycuron, benzohydroxamic acid, bentaluron, benthiazole, benthiavalicarb-isopropyl, penthiopyrad, penflufen, boscalid, phosdiphen, fosetyl, fosetyl-Al, polyoxins, polyoxorim, polycarbamate, folpet, formaldehyde, machine oil, maneb, mancozeb, mandipropamid, myclozolin, myclobutanil, mildiomycin, milneb, mecarbinzid, methasulfocarb, metazoxolon, metam, metam-sodium, metalaxyl, metalaxyl-M, metiram, methyl isothiocyanate, meptyldinocap, metconazole, metsulfovax, methfuroxam, metominostrobin, metrafenone, mepanipyrim, mefenoxam, meptyldinocap, mepronil, mebenil, iodomethane, rabenzazole, benzalkonium chloride, basic copper chloride, basic copper sulfate, inorganic microbicides such as silver, sodium hypochlorite, cupric hydroxide, wettable sulfur, calcium polysulfide, potassium hydrogen carbonate, sodium hydrogen carbonate, sulfur, copper sulfate anhydride, nickel dimethyldithiocarbamate, copper compounds such as copper-8-quinolinolate (oxine copper), zinc sulfate and copper sulfate pentahydrate.

Exemplary herbicides used for the same purposes as above include 1-naphthylacetamide, 2,4-PA, 2,3,6-TBA, 2,4,5-T, 2,4,5-TB, 2,4-D, 2,4-DB, 2,4-DEB, 2,4-DEP, 3,4-DA, 3,4-DB, 3,4-DP, 4-CPA, 4-CPB, 4-CPP, MCP, MCPA, MCPA-thioethyl, MCPB, ioxynil, aclonifen, azafenidin, acifluorfen, aziprotryne, azimsulfuron, asulam, acetochlor, atrazine, atraton, anisuron, anilofos, aviglycine, abscisic acid, amicarbazone, amidosulfuron, amitrole, aminocyclopyrachlor, aminopyralid, amibuzin, amiprophos-methyl, ametridione, ametryn, alachlor, allidochlor, alloxydim, alorac, isouron, isocarbamid, isoxachlortole, isoxapyrifop, isoxaflutole, isoxaben, isocil, isonoruron, isoproturon, isopropalin, isopolinate, isomethiozin, inabenfide, ipazine, ipfencarbazone, iprymidam, imazaquin, imazapic, imazapyr, imazamethapyr, imazamethabenz, imazamethabenz-methyl, imazamox, imazethapyr, imazosulfuron, indaziflam, indanofan, indolebutyric acid, uniconazole-P, eglinazine, esprocarb, ethametsulfuron, ethametsulfuron-methyl, ethalfluralin, ethiolate, ethychlozate-ethyl, ethidimuron, etinofen, ethephon, ethoxysulfuron, ethoxyfen, etnipromid, ethofumesate, etobenzanid, epronaz, erbon, endothal, oxadiazon, oxadiargyl, oxaziclomefone, oxasulfuron, oxapyrazon, oxyfluorfen, oryzalin, orthosulfamuron, orbencarb, cafenstrole, cambendichlor, carbasulam, carfentrazone, carfentrazone-ethyl, karbutilate, carbetamide, carboxazole, quizalofop, quizalofop-P, quizalofop-ethyl, xylachlor, quinoclamine, quinonamid, quinclorac, quinmerac, cumyluron, cliodinate, glyphosate, glufosinate, glufosinate-P, credazine, clethodim, cloxyfonac, clodinafop, clodinafop-propargyl, chlorotoluron, clopyralid, cloproxydim, cloprop, chlorbromuron, clofop, clomazone, chlomethoxynil, chlomethoxyfen, clomeprop, chlorazifop, chlorazine, cloransulam, chloranocryl, chloramben, cloransulam-methyl, chloridazon, chlorimuron, chlorimuron-ethyl, chlorsulfuron, chlorthal, chlorthiamid, chlortoluron, chlornitrofen, chlorfenac, chlorfenprop, chlorbufam, chlorflurazole, chlorflurenol, chlorprocarb, chlorpropham, chlormequat, chloreturon, chloroxynil, chloroxuron, chloropon, saflufenacil, cyanazine, cyanatryn, di-allate, diuron, diethamquat, dicamba, cycluron, cycloate, cycloxydim, diclosulam, cyclosulfamuron, dichlorprop, dichlorprop-P, dichlobenil, diclofop, diclofop-methyl, dichlormate, dichloralurea, diquat, cisanilide, disul, siduron, dithiopyr, dinitramine, cinidon-ethyl, dinosam, cinosulfuron, dinoseb, dinoterb, dinofenate, dinoprop, cyhalofop-butyl, diphenamid, difenoxuron, difenopenten, difenzoquat, cybutryne, cyprazine, cyprazole, diflufenican, diflufenzopyr, dipropetryn, cypromid, cyperquat, gibberellin, simazine, dimexano, dimethachlor, dimidazon, dimethametryn, dimethenamid, simetryn, simeton, dimepiperate, dimefuron, cinmethylin, swep, sulglycapin, sulcotrione, sulfallate, sulfentrazone, sulfosulfuron, sulfometuron, sulfometuron-methyl, secbumeton, sethoxydim, sebuthylazine, terbacil, daimuron, dazomet, dalapon, thiazafluron, thiazopyr, thiencarbazone, thiencarbazone-methyl, tiocarbazil, tioclorim, thiobencarb, thidiazimin, thidiazuron, thifensulfuron, thifensulfuron-methyl, desmedipham, desmetryn, tetrafluron, thenylchlor, tebutam, tebuthiuron, terbumeton, tepraloxydim, tefuryltrione, tembotrione, delachlor, terbacil, terbucarb, terbuchlor, terbuthylazine, terbutryn, topramezone, tralkoxydim, triaziflam, triasulfuron, tri-allate, trietazine, tricamba, triclopyr, tridiphane, tritac, tritosulfuron, triflusulfuron, triflusulfuron-methyl, trifluralin, trifloxysulfuron, tripropindan, tribenuron-methyl, tribenuron, trifop, trifopsime, trimeturon, naptalam, naproanilide, napropamide, nicosulfuron, nitralin, nitrofen, nitrofluorfen, nipyraclofen, neburon, norflurazon, noruron, barban, paclobutrazol, paraquat, parafluron, haloxydine, haloxyfop, haloxyfop-P, haloxyfop-methyl, halosafen, halosulfuron, halosulfuron-methyl, picloram, picolinafen, bicyclopyrone, bispyribac, bispyribac-sodium, pydanon, pinoxaden, bifenox, piperophos, hymexazol, pyraclonil, pyrasulfotole, pyrazoxyfen, pyrazosulfuron, pyrazosulfuron-ethyl, pyrazolate, bilanafos, pyraflufen-ethyl, pyriclor, pyridafol, pyrithiobac, pyrithiobac-sodium, pyridate, pyriftalid, pyributicarb, pyribenzoxim, pyrimisulfan, primisulfuron, pyriminobac-methyl, pyroxasulfone, pyroxsulam, fenasulam, phenisopham, fenuron, fenoxasulfone, fenoxaprop, fenoxaprop-P, fenoxaprop-ethyl, phenothiol, fenoprop, phenobenzuron, fenthiaprop, fenteracol, fentrazamide, phenmedipham, phenmedipham-ethyl, butachlor, butafenacil, butamifos, buthiuron, buthidazole, butylate, buturon, butenachlor, butroxydim, butralin, flazasulfuron, flamprop, furyloxyfen, prynachlor, primisulfuron-methyl, fluazifop, fluazifop-P, fluazifop-butyl, fluazolate, fluroxypyr, fluothiuron, fluometuron, fluoroglycofen, flurochloridone, fluorodifen, fluoronitrofen, fluoromidine, flucarbazone, flucarbazone-sodium, fluchloralin, flucetosulfuron, fluthiacet, fluthiacet-methyl, flupyrsulfuron, flufenacet, flufenican, flufenpyr, flupropacil, flupropanate, flupoxam, flumioxazin, flumiclorac, flumiclorac-pentyl, flumipropyn, flumezin, fluometuron, flumetsulam, fluridone, flurtamone, fluroxypyr, pretilachlor, proxan, proglinazine, procyazine, prodiamine, prosulfalin, prosulfuron, prosulfocarb, propaquizafop, propachlor, propazine, propanil, propyzamide, propisochlor, prohydrojasmon, propyrisulfuron, propham, profluazol, profluralin, prohexadione-calcium, propoxycarbazone, propoxycarbazone-sodium, profoxydim, bromacil, brompyrazon, prometryn, prometon, bromoxynil, bromofenoxim, bromobutide, bromobonil, florasulam, hexachloroacetone, hexazinone, pethoxamid, benazolin, penoxsulam, pebulate, beflubutamid, vernolate, perfluidone, bencarbazone, benzadox, benzipram, benzylaminopurine, benzthiazuron, benzfendizone, bensulide, bensulfuron-methyl, benzoylprop, benzobicyclon, benzofenap, benzofluor, bentazone, pentanochlor, benthiocarb, pendimethalin, pentoxazone, benfluralin, benfuresate, fosamine, fomesafen, foramsulfuron, forchlorfenuron, maleic hydrazide, mecoprop, mecoprop-P, medinoterb, mesosulfuron, mesosulfuron-methyl, mesotrione, mesoprazine, methoprotryne, metazachlor, methazole, metazosulfuron, methabenzthiazuron, metamitron, metamifop, metam, methalpropalin, methiuron, methiozolin, methiobencarb, methyldymron, metoxuron, metosulam, metsulfuron, metsulfuron-methyl, metflurazon, metobromuron, metobenzuron, methometon, metolachlor, metribuzin, mepiquat-chloride, mefenacet, mefluidide, monalide, monisouron, monuron, monochloroacetic acid, monolinuron, molinate, morfamquat, iodosulfuron, iodosulfuron-methyl-sodium, iodobonil, iodomethane, lactofen, linuron, rimsulfuron, lenacil, rhodethanil, calcium peroxide and methyl bromide.

Exemplary biopesticides used for the same purposes as above include viral formulations such as nuclear polyhedrosis viruses (NPV), granulosis viruses (GV), cytoplasmic

43 polyhedrosis viruses (CPV) and entomopox viruses (EPV); microbial pesticides used as an insecticide or a nematicide, such as *Monacrosporium phymatophagum, Steinernema carpocapsae, Steinernema kushidai* and *Pasteuria penetrans*; microbial pesticides used as a microbicide, such as *Trichoderma lignorum, Agrobacterium radiobactor*, avirulent *Erwinia carotovora* and *Bacillus subtilis*; and biopesticides used as a herbicide, such as *Xanthomonas campestris*. Such a combined use of the agricultural or horticultural insecticide of the present invention with the foregoing biopesticide as a mixture can be expected to provide the same effect as above.

Other examples of the biopesticides include natural predators such as *Encarsia formosa, Aphidius colemani, Aphidoletes aphidimyza, Diglyphus isaea, Dacnusa sibirica, Phytoseiulus persimilis, Amblyseius cucumeris* and *Orius sauteri*; microbial pesticides such as *Beauveria brongniartii*; and pheromones such as (Z)-10-tetradecenyl acetate, (E,Z)-4,10-tetradecadienyl acetate, (Z)-8-dodecenyl acetate, (Z)-11-tetradecenyl acetate, (Z)-13-icosen-10-one and 14-methyl-1-octadecene.

Hereinafter, the production examples of representative compounds of the present invention and their intermediates will be described in more detail, but the present invention is not limited only to these examples.

EXAMPLES

Reference Example 1

Production Method of 4-trifluoromethylpyrimidin-1-ium-1,6-diamine, 2,4,6-trimethylbenzenesulfonate (Salt)

[Chem. 9]

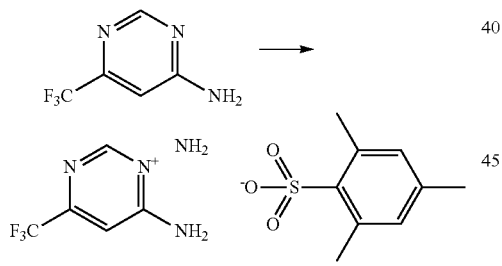

To a microwave tube equipped with a magnetic stirrer bar, 2,2,2-trifluoroacetic acid (4.4 g, 2.54 mmol, 2.9 mL) was added, and subsequently (t-butoxycarbonylamino)2,4,6-trimethylbenzenesulfonate (1 g, 2.54 mmol) was added at 0° C. The reaction mixture was stirred at 0° C. for 2 hours, iced water was added, and the precipitate was collected by filtration. The wet cake was washed with water and dissolved in dichloromethane (5 mL). The resulting solution was dried over sodium sulfate and added dropwise to a stirred solution of 6-trifluoromethylpyrimidin-4-amine (0.373 g, prepared according to the description in WO 2007/113558) in dichloromethane (5 mL) at 0° C. The reaction mixture was allowed to stand at that temperature for 1 hour and then at room temperature overnight. The reaction mixture obtained as a white suspension was diluted with diethyl ether (8 mL), and the precipitate was collected by filtration to give the desired product (0.79 g, 82%).

44

Reference Example 2

Production Method of 2-(3-ethylsulfonyl-5-bromo-2-pyridyl)-7-trifluoromethyl-[1,2,4]triazolo[1,5-c]pyrimidine

[Chem. 10]

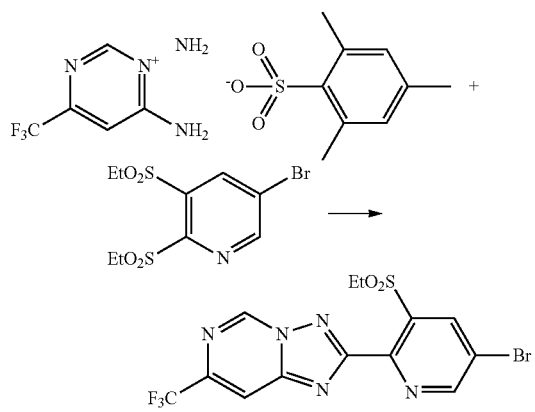

4-Trifluoromethylpyrimidin-1-ium-1,6-diamine, 2,4,6-trimethylbenzenesulfonate (salt) (0.3 g, 0.791 mmol), 3-ethylsulfonyl-5-bromopyridine-2-carboxylic acid (0.284 g, 1.18 mmol), and 3-(ethyliminomethylenamino)-N,N-dimethyl-propan-1-amine hydrochloride (0.18 g, 0.94 mmol) were dissolved in pyridine (2 mL), and the mixture was heated at 120° C. for 3 hours. The reaction mixture was poured into water, and the aqueous layer was extracted with EtOAc (ethyl acetate) three times. The combined organic layers were washed successively with water and brine, dried over anhydrous $Na_2SO_4$ (sodium sulfate), and filtered. The filtrate was concentrated in vacuo. The crude product was washed with diethyl ether and filtered to give the desired product as a white powder (90 mg, 33%).

Reference Example 3

Production Method of 2-(3-ethylsulfonyl-5-vinyl-2-pyridyl)-7-trifluoromethyl-[1,2,4]triazolo[1,5-a]pyridine

[Chem. 11]

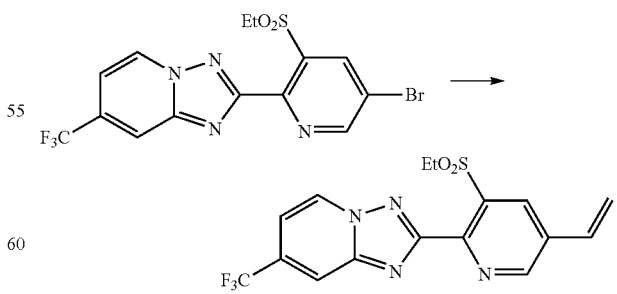

To a DME (dimethyl ether) solution (4.0 mL) of 2-(3-ethylsulfonyl-5-bromo-2-pyridyl)-7-trifluoromethyl-[1,2,4]triazolo[1,5-a]pyridine (0.28 g) produced as in Reference Examples 1 and 2, potassium vinyl trifluoroborate (0.013 g), Reference Example 4

Production Method of 5-ethylsulfonyl-2-(7-trifluoromethyl-[1,2,4]triazolo[1,5-a]pyridin-2-yl)nicotinaldehyde

[Chem. 12]

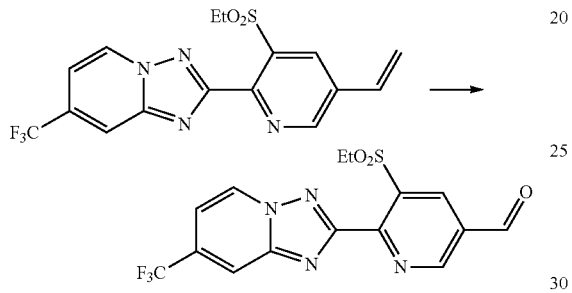

To a THF (tetrahydrofuran): aqueous pH 7 buffer (2:1) solution (30 mL) of 2-(3-ethylsulfonyl-5-vinyl-2-pyridyl)-7-trifluoromethyl-[1,2,4]triazolo[1,5-a]pyridine, a 50% aqueous NMO (N-methylmorpholine N-oxide) solution (0.44 g) and a 0.1 M OsO$_4$ solution in a 50% t-BuOH (t-butanol) (0.3 mL) were added, and the mixture was stirred at room temperature overnight. NaIO$_4$ (0.20 g) was added, and the mixture was stirred at room temperature for 2 hours. After the completion of the reaction, a saturated Na$_2$S$_2$O$_3$ solution was added, and ethyl acetate extraction was performed. The organic layer was washed with a saturated aqueous sodium chloride solution. The organic layer was dried over anhydrous magnesium sulfate and then dried in vacuo. The residue was purified by silica gel chromatography to give the desired compound (0.20 g, 83%).

Production Example 1

Production Method of 5-ethylsulfonyl-6-(7-pentafluoroethyl-[1,2,4]triazolo[1,5-c]pyridin-2-yl)picolinaldehyde O-(2,2,2-trifluoroethyl)oxime (Compound No. 2-42)

[Chem. 13]

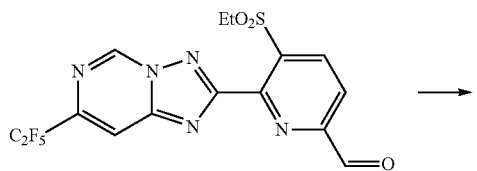

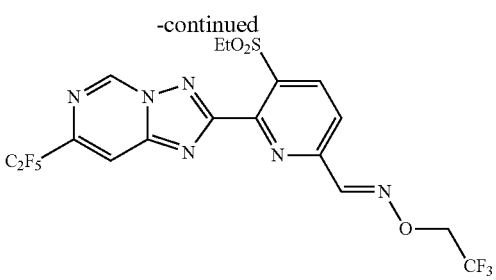

To a chloroform solution (1 mL) of 5-ethylsulfonyl-6-(7-pentafluoroethyl-[1,2,4]triazolo[1,5-c]pyridin-2-yl)picolinaldehyde (0.006 g, 0.013 mmol) produced as in Reference Examples 1 to 4, O-(2,2,2-trifluoroethyl)hydroxylamine hydrochloride (0.003 g, 0.021 mmol) and pyridine (0.002 mL, 0.021 mmol) were added at room temperature, and the mixture was stirred for 1 hour. After the completion of the reaction, a 1 N aqueous hydrochloric acid solution was added, and ethyl acetate extraction was performed. The organic layer was dried over anhydrous magnesium sulfate and then dried in vacuo. The residue was purified by silica gel chromatography to give the desired compound (0.006 g, 0.011 mmol, 85%).

Production Example 2

Production Method of 5-ethylsulfonyl-2-(7-trifluoromethyl-[1,2,4]triazolo[1,5-a]pyridin-2-yl)nicotinaldehyde O-(2,2-difluoroethyl)oxime (Compound No. 1-7)

[Chem. 14]

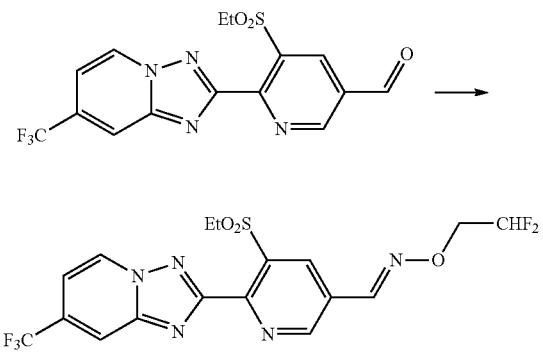

To a chloroform solution (2 mL) of 5-ethylsulfonyl-2-(7-trifluoromethyl-[1,2,4]triazolo[1,5-a]pyridin-2-yl)nicotinaldehyde (0.050 g, 0.13 mmol) produced as in Reference Examples 1 to 4, O-(2,2-difluoroethyl)hydroxylamine hydrochloride (0.026 g, 0.20 mmol) and pyridine (0.015 mL, 0.20 mmol) were added at room temperature, and the mixture was stirred for 1 hour. After the completion of the reaction, a 1 N aqueous HCl solution was added, and ethyl acetate extraction was performed. The organic layer was dried over anhydrous magnesium sulfate and then dried in vacuo. The residue was purified by silica gel chromatography to give the desired compound (0.044 g, 0.095 mmol, 73%).

Reference Example 5

Production Method of 5-ethylsulfonyl-6-(7-trifluoromethyl-[1,2,4]triazolo[1,5-a]pyridin-2-yl)nicotinic Acid Methyl Ester

[Chem. 15]

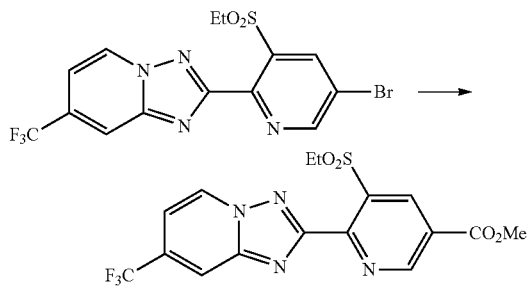

2-(5-Bromo-3-ethylsulfonyl-2-pyridyl)-7-trifluoromethyl-[1,2,4]triazolo[1,5-a]pyridine (5.21 g) produced as in Reference Examples 1 and 2, diphenylphosphinobutane (102 mg), bistriphenylphosphine dichloropalladium (84 mg), methanol (60 ml), and triethylamine (1.68 ml) were added to a 200-ml stainless steel autoclave. The reaction system was purged with carbon monoxide, and the mixture was stirred under a pressure of 3 MPa at 110° C. for 2 hours. After cooling to room temperature, the reaction mixture was degassed, and a saturated aqueous sodium bicarbonate solution was added. The reaction mixture was extracted with ethyl acetate, and the organic layer was dried over anhydrous magnesium sulfate and concentrated. The residue was subjected to column chromatography to give the desired compound (2.34 mg, yield: 47%).

$^1$H-NMR: 9.54 (d, 1H), 9.10 (d, 1H), 8.81 (d, 1H), 8.15 (t, 1H), 7.33 (d, 1H), 4.18-4.09 (m, 5H), 1.44 (t, 3H)

Reference Example 6

Production method of 5-ethylsulfonyl-6-(7-trifluoromethyl-[1,2,4]triazolo[1,5-a]pyridin-2-yl)nicotinic Acid

[Chem. 16]

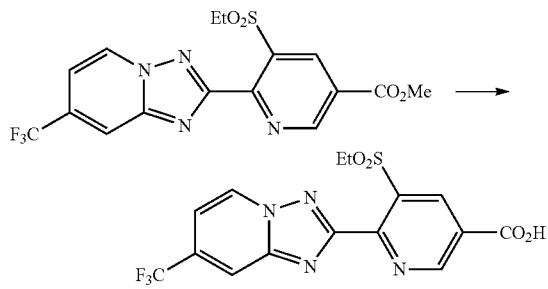

To a mixture of 5-ethylsulfonyl-6-(7-trifluoromethyl-[1,2,4]triazolo[1,5-a]pyridin-2-yl)nicotinic acid methyl ester (2.34 g), methanol (40 mL), and tetrahydrofuran (40 mL), an aqueous lithium hydroxide solution (4.0 M, 2.11 mL) was added. The mixture was stirred at room temperature for 2 hours, and 2 N hydrochloric acid was added until the pH of the reaction mixture became 4 or less. The resulting solid was collected to give the desired product (1.97 g, yield: 87%).

$^1$H-NMR: 9.58 (d, 1H), 9.14 (d, 1H), 8.82 (d, 1H), 8.16 (s, 1H), 7.35 (d, 1H), 4.07 (d, 2H), 1.45 (t, 3H)

Production Example 3

Production Method of 5-ethylsulfonyl-N-(2-methylthioethoxy)-6-(7-trifluoromethyl-[1,2,4]triazolo[1,5-a]pyridin-2-yl)nicotinimidoyl bromide (Compound No. 3-19)

[Chem. 17]

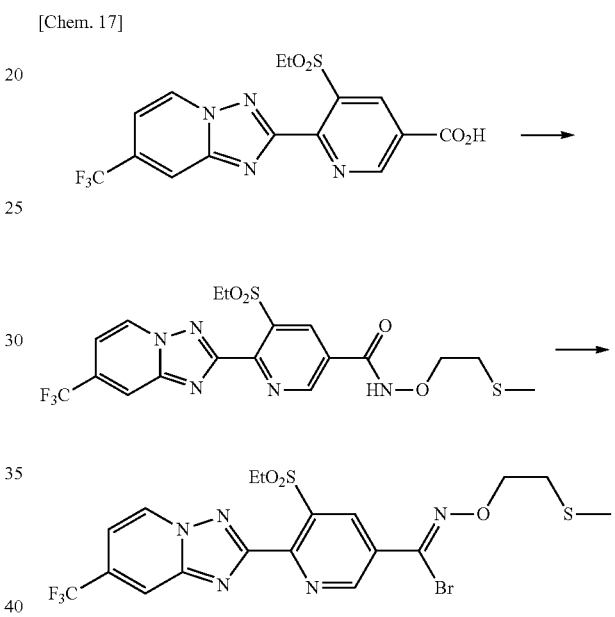

To a mixture of 5-ethylsulfonyl-6-(7-trifluoromethyl-[1,2,4]triazolo[1,5-a]pyridin-2-yl)nicotinic acid (1 g), methylthioethoxyamine hydrochloride (0.3 M chloroform solution, 12.5 mL), dimethylaminopyridine (916 mg), and pyridine (592 µL), 1-(3-dimethylaminopropyl)-3-ethylcarbodiimide hydrochloride (718 mg) was added. The mixture was stirred at room temperature for 2 hours, 2 N HCl was added, and ethyl acetate extraction was performed. The organic layer was concentrated to give the desired 5-ethylsulfonyl-N-(2-methylthioethoxy)-6-(7-trifluoromethyl-[1,2,4]triazolo[1,5-a]pyridin-2-yl)nicotinamide (1.76 g).

To the resulting mixture, tetrahydrofuran (50 ml), triphenylphosphine (1.96 g), and carbon tetrabromide (2.5 g) were added, and the mixture was stirred at room temperature for 1 hour. The insoluble matter was filtered off, and the filtrate was concentrated. An aqueous sodium bicarbonate solution was added to the residue, and ethyl acetate extraction was performed. The organic layer was concentrated, and the residue was subjected to column chromatography to give the desired 5-ethylsulfonyl-N-(2-methylthioethoxy)-6-(7-trifluoromethyl-[1,2,4]triazolo[1,5-a]pyridin-2-yl)nicotinimidoyl bromide (594 mg, yield: 43%). Melting point: 188° C. to 189° C.

Production Example 4

Production Method of cyclopropyl(5-ethylsulfonyl)-6-(7-trifluoromethyl-[1,2,4]triazolo[1,5-a]pyridin-2-yl)pyridin-3-yl)methanone O-(2-methylthioethyl)oxime (Compound No. 3-28)

[Chem. 18]

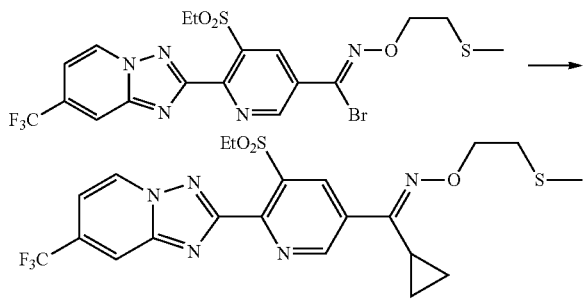

A mixture of the 5-ethylsulfonyl-N-(2-methylthioethoxy)-6-(7-trifluoromethyl-[1,2,4]triazolo[1,5-a]pyridin-2-yl)nicotinimidoyl bromide (91 mg) produced in Production Example 3, cyclopropylboronic acid (71 mg), tetrakis(triphenylphosphine)palladium (36 mg), toluene (2 mL), and a 2 M aqueous sodium carbonate solution (0.8 mL) was heated at 100° C. with stirring under an argon atmosphere for 1 hour. The reaction mixture was allowed to cool down to room temperature and then concentrated. The residue was subjected to column chromatography to give the desired compound (49 mg, yield: 59%).
Melting point: 167° C. to 168° C.

Production Example 5

Production Method of (5-ethylsulfonyl-6-(7-trifluoromethyl-[1,2,4]triazolo[1,5-a]pyridin-2-yl)pyridin-3-yl)phenylmethanone O-(2-methylthioethyl)oxime (Compound No. 3-46)

[Chem. 19]

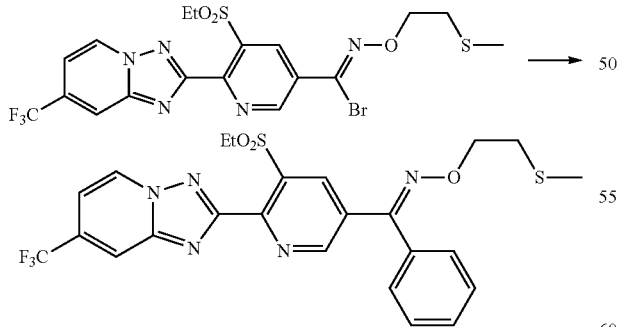

A mixture of 5-ethylsulfonyl-N-(2-methylthioethoxy)-6-(7-trifluoromethyl-[1,2,4]triazolo[1,5-a]pyridin-2-yl)nicotinimidoyl bromide (77 mg), phenylboronic acid (51 mg), tetrakis(triphenylphosphine)palladium (36 mg), toluene (2 mL), and a 2 M aqueous sodium carbonate solution (0.4 mL) was heated at 100° C. with stirring under an argon atmosphere for 1 hour. The reaction mixture was allowed to cool down to room temperature and then concentrated. The residue was subjected to column chromatography to give the desired compound (64 mg, yield: 84%).
Melting point: 157° C. to 158° C.

Production Example 6

Production Method of methyl 5-ethylsulfonyl-N-(2-methylthioethoxy)-6-(7-(trifluoromethyl)-[1,2,4]triazolo[1,5-a]pyridin-2-yl)nicotinimidate (Compound No. 3-1)

[Chem. 20]

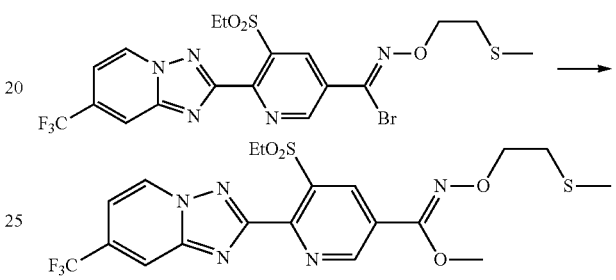

A mixture of 5-ethylsulfonyl-N-(2-methylthioethoxy)-6-(7-trifluoromethyl-[1,2,4]triazolo[1,5-a]pyridin-2-yl)nicotinimidoyl bromide (107 mg), cesium carbonate (189 mg), Pd Rockphos G3 (5 mg, Sigma-Aldrich), toluene (1 mL), and methanol (1 mL) was heated at 60° C. with stirring under an argon atmosphere for 1 hour. The reaction mixture was allowed to cool down to room temperature and then concentrated. The residue was subjected to column chromatography to give the desired compound (36 mg, yield: 38%).
Melting point: 165° C. to 166° C.

Reference Example 7

Production method of N-methylthioethoxyphthalimide

[Chem. 21]

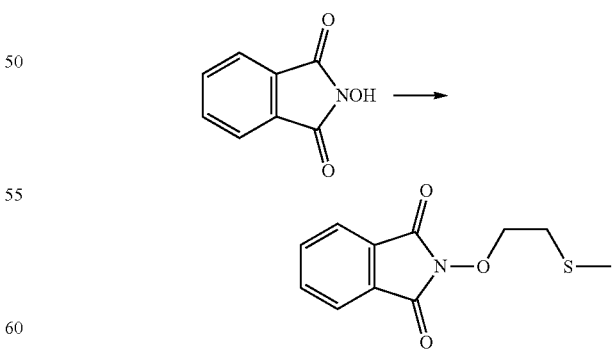

To a mixture of N-hydroxyphthalimide (10 g), triphenylphosphine (19.3 g), methylthioethanol (6.4 mL), and tetrahydrofuran (120 mL), diethyl azodicarboxylate (2.2 M toluene solution, 33.4 mL) was added. The mixture was stirred at room temperature for 1 hour and then concentrated.

The residue was subjected to column chromatography to give the desired N-methylthioethoxyphthalimide (15 g, yield: 100%).

Reference Example 8

Production Method of Methylthioethoxyamine

[Chem. 22]

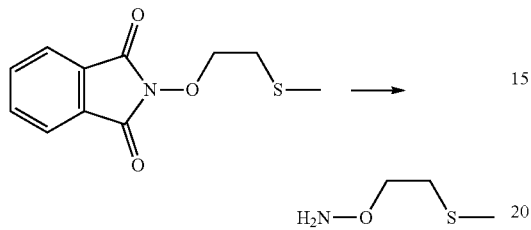

To a mixture of N-ethylthioethoxyphthalimide (15 g) and chloroform (60 mL), hydrazine monohydrate (3 mL) was added. The mixture was stirred at room temperature for 4 hours, and the insoluble matter was removed by Celite filtration. The filtrate was dried over anhydrous magnesium sulfate and then filtered again. The resulting filtrate was used as a 0.3 M solution of methylthioethoxyamine for the reaction.

Formulation examples are shown below, but the present invention is not limited thereto. In the formulation examples, "part" means part by weight.

Formulation Example 1

| | |
|---|---|
| Compound of the present invention | 10 parts |
| Xylene | 70 parts |
| N-methylpyrrolidone | 10 parts |
| Mixture of polyoxyethylene nonylphenyl ether and calcium alkylbenzene sulfonate (weight ratio of 1:1) | 10 parts |

The above ingredients are uniformly mixed for dissolution to give an emulsifiable concentrate formulation.

Formulation Example 2

| | |
|---|---|
| Compound of the present invention | 3 parts |
| Clay powder | 82 parts |
| Diatomite powder | 15 parts |

The above ingredients are uniformly mixed and then pulverized to give a dust formulation.

Formulation Example 3

| | |
|---|---|
| Compound of the present invention | 5 parts |
| Mixture of bentonite powder and clay powder | 90 parts |
| Calcium lignosulfonate | 5 parts |

The above ingredients are uniformly mixed. After addition of an appropriate volume of water, the mixture is kneaded, granulated and dried to give a granular formulation.

Formulation Example 4

| | |
|---|---|
| Compound of the present invention | 20 parts |
| Kaolin and synthetic high-dispersion silicic acid | 75 parts |
| Mixture of polyoxyethylene nonylphenyl ether and calcium alkylbenzene sulfonate (weight ratio of 1:1) | 5 parts |

The above ingredients are uniformly mixed and then pulverized to give a wettable powder formulation.

Formulation Example 5

| | |
|---|---|
| Compound of the present invention | 20 parts |
| Polyoxyethylene lauryl ether | 3 parts |
| Sodium dioctyl sulfosuccinate | 3.5 parts |
| Dimethyl sulfoxide | 37 parts |
| 2-Propanol | 36.5 parts |

The above ingredients are uniformly mixed for dissolution to give a water-soluble concentrate preparation.

Formulation Example 6

| | |
|---|---|
| Compound of the present invention | 2 parts |
| Dimethyl sulfoxide | 10 parts |
| 2-Propanol | 35 parts |
| Acetone | 53 parts |

The above ingredients are uniformly mixed for dissolution to give a solution for spraying.

Formulation Example 7

| | |
|---|---|
| Compound of the present invention | 5 parts |
| Hexylene glycol | 50 parts |
| Isopropanol | 45 parts |

The above ingredients are uniformly mixed for dissolution to give a solution for transdermal administration.

Formulation Example 8

| | |
|---|---|
| Compound of the present invention | 5 parts |
| Propylene glycol monomethyl ether | 50 parts |
| Dipropylene glycol | 45 parts |

The above ingredients are uniformly mixed for dissolution to give a solution for transdermal administration.

Formulation Example 9

| | |
|---|---|
| Compound of the present invention | 2 parts |
| Light liquid paraffin | 98 parts |

The above ingredients are uniformly mixed for dissolution to give a solution for transdermal (pour-on) administration.

Formulation Example 10

| | |
|---|---|
| Compound of the present invention | 2 parts |
| Light liquid paraffin | 58 parts |
| Olive oil | 30 parts |
| ODO-H | 9 parts |
| Shin-etsu silicone (manufactured by Shin-Etsu Chemical Co., Ltd.) | 1 part |

The above ingredients are uniformly mixed for dissolution to give a solution for transdermal (pour-on) administration.

Hereinafter, test examples in connection with the present invention are shown, but the present invention is not limited thereto.

Test Example 1

Test for Control Efficacy on *Myzus persicae*

Chinese cabbage plants were planted in plastic pots (diameter: 8 cm, height: 8 cm), Green peach aphids (*M. persicae*) were propagated on the plants, and the number of surviving Green peach aphids in each pot was counted. The condensed heterocyclic compounds having a bridgehead nitrogen atom represented by the general formula (1) of the present invention or salts thereof were separately dispersed in water and diluted to 500 ppm. The agrochemical dispersions were applied to the foliage of the potted Chinese cabbage plants. After the plants were air-dried, the pots were kept in a greenhouse. At 6 days after the foliar application, the number of surviving Green peach aphids on the Chinese cabbage plant in each pot was counted, the control rate was calculated according to the formula shown below, and the control efficacy was evaluated according to the criteria shown below.

$$\text{Control rate} = 100 - \{(T \times Ca)/(Ta \times C)\} \times 100 \quad [\text{Math. 1}]$$

Ta: the number of survivors before the foliar application in a treatment plot
T: the number of survivors after the foliar application in a treatment plot
Ca: the number of survivors before the foliar application in a non-treatment plot
C: the number of survivors after the foliar application in a non-treatment plot
Criteria
A: the control rate is 100%.
B: the control rate is 90 to 99%.
C: the control rate is 80 to 89%.
D: the control rate is 50 to 79%.

As a result, the compounds 1-3, 1-5, 1-6, 1-7, 1-8, 1-9, 1-15, 1-16, 1-24, 1-25, 1-26, 1-27, 1-46, 1-47, 1-48, 1-49, 1-50, 1-51, 1-52, 2-6, 2-7, 2-8, 2-15, 2-16, 2-17, 2-20, 2-24, 2-25, 2-42, 2-43, 2-48, 2-51, 2-52, 3-1, 3-19, 3-28, 3-46, 3-52, and 3-82 of the present invention showed the activity level evaluated as A.

Test Example 2

Insecticidal Test on *Laodelphax striatellus*

The condensed heterocyclic compounds having a bridgehead nitrogen atom represented by the general formula (1) of the present invention or salts thereof were separately dispersed in water and diluted to 500 ppm. Rice plant seedlings (variety: Nihonbare) were dipped in the agrochemical dispersions for 30 seconds. After air-dried, each seedling was put into a separate glass test tube and inoculated with ten 3rd-instar larvae of *L. striatellus*, and then the glass test tubes were capped with cotton plugs. At 8 days after the inoculation, the numbers of surviving larvae and dead larvae of *L. striatellus* were counted, the corrected mortality rate was calculated according to the formula shown below, and the insecticidal efficacy was evaluated according to the criteria of Test Example 1.

$$\text{Corrected mortality rate (\%)} = \quad [\text{Math. 2}]$$
$$100 \times (\text{Survival rate in a non-treatment plot} -$$
$$\text{Survival rate in a treatment plot})/$$
$$\text{Survival rate in a non-treatment plot}$$

As a result, the compounds 1-3, 1-5, 1-6, 1-7, 1-8, 1-9, 1-15, 1-16, 1-24, 1-25, 1-26, 1-27, 1-46, 1-47, 1-48, 1-49, 1-50, 1-51, 1-52, 2-6, 2-7, 2-8, 2-15, 2-16, 2-17, 2-20, 2-24, 2-25, 2-42, 2-43, 2-48, 2-51, 2-52, 3-1, 3-19, 3-28, 3-46, 3-52, and 3-82 showed the activity level evaluated as A.

Test Example 3

Insecticidal Test on *Plutella xylostella*

Adults of *P. xylostella* were released onto Chinese cabbage seedlings and allowed to lay eggs thereon. At 2 days after the release of the adults, the Chinese cabbage seedlings with laid eggs were dipped for about 30 seconds in agrochemical formulations diluted to 500 ppm, each of which contained a different kind of condensed heterocyclic compound having a bridgehead nitrogen atom represented by the general formula (1) of the present invention as an active ingredient. After air-dried, the seedlings were kept in a thermostatic chamber at 25° C. At 6 days after the dip treatment, the number of hatched larvae per plot was counted, the mortality rate of *P. xylostella* was calculated according to the formula shown below, and the insecticidal efficacy was evaluated according to the criteria of Test Example 1. This test was conducted in triplicate using 10 adults of *P. xylostella* per plot.

Corrected mortality rate (%) = [Math. 3]

$100 \times$ (Number of hatched larvae in a non-treatment plot −

Number of hatched larvae in a treatment plot)/

Number of hatched larvae in a non-treatment plot

As a result, the compounds 1-3, 1-5, 1-6, 1-7, 1-8, 1-9, 1-15, 1-16, 1-24, 1-25, 1-26, 1-27, 1-46, 1-47, 1-48, 1-49, 1-50, 1-51, 1-52, 2-6, 2-7, 2-8, 2-15, 2-16, 2-17, 2-20, 2-24, 2-25, 2-42, 2-43, 2-48, 2-51, 2-52, 3-1, 3-19, 3-28, 3-46, 3-52, and 3-82 showed the activity level evaluated as A.

Test Example 4

Larval Motility Assay on *Haemonchus contortus*

Dimethyl sulfoxide (DMSO) diluted solutions of various compounds of the present invention were added at the final concentration of 50 ppm to the wells of a 96-well plate containing a predetermined conditioned medium. Twenty L1 stage larvae of *H. contortus* were introduced into each well of the 96-well plate. The plate was allowed to stand for 4 days, and then larval motility was examined. The percent motility inhibition in the wells of each treatment was calculated relative to the wells of treatment with DMSO only.

As a result, the compounds 1-7 and 1-50 of the present invention showed a percent motility inhibition of 50% or more.

Test Example 5

Larval Motility Assay on *Dirofilaria immitis*

Five hundred L1 stage larvae of *D. immitis* were diluted in a predetermined conditioned medium and introduced into each well of a 96-well plate. DMSO diluted solutions of various compounds of the present invention were added at the final concentration of 50 ppm to the wells of the 96-well plate. The plate was allowed to stand for 3 days, and then larval motility was examined. The percent motility inhibition in the wells of each treatment was calculated relative to the wells of treatment with DMSO only.

As a result, the compounds 1-7, 1-49, and 1-50 of the present invention showed inhibitory efficacy against larvae of *D. immitis* with a percent motility inhibition of 50% or more.

Test Example 6

Assay for Oral Parasiticidal Activity Against Adults of *Ctenocephalides felis*

Newly-emerged adults of *C. felis* were placed into test cages (10 adults per test cage). DMSO diluted solutions of various compounds of the present invention were added to aliquots of bovine blood at the final concentration of 50 ppm and orally administered to the adults of *C. felis* using a feeder. The mortality rate was examined on the following day. Aberrant adults were regarded as the dead.

As a result, the compounds 1-7, 1-8, 1-15, 1-26, 1-47, 1-49, and 1-50 of the present invention showed parasiticidal activity against adults of *C. felis* with a mortality rate of 50% or more.

Test Example 7

Assay for Transdermal Parasiticidal Activity Against Nymphs of *Rhipicephalus sanguineus*

DMSO diluted solutions of various compounds of the present invention were individually diluted to the final concentration of 100 ppm with an acetone/triton solution and applied to the inside of vented sample bottles. After overnight drying, ten nymphs of *R. sanguineus* were introduced into each bottle, and the mortality rate was examined two days later. Aberrant adults were regarded as the dead.

As a result, the compounds 1-47 and 1-50 of the present invention showed parasiticidal activity against nymphs of *R. sanguineus* with a mortality rate of 50% or more.

INDUSTRIAL APPLICABILITY

The compound of the present invention is highly effective in controlling a wide range of agricultural or horticultural pests and animal endoparasites and ectoparasites and thus is useful.

The invention claimed is:

1. A condensed heterocyclic compound which has a bridgehead nitrogen atom and is bound to a pyridine ring containing an oxime group, the compound represented by the following formula:

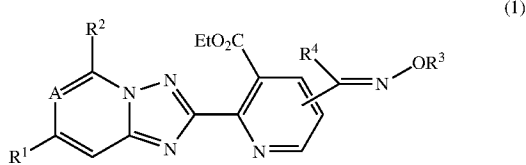

(1)

wherein
$R^1$ represents
(a1) a hydrogen atom;
(a2) a $(C_1\text{-}C_6)$ alkyl group;
(a3) a $(C_3\text{-}C_6)$ cycloalkyl group; or
(a4) a halo $(C_1\text{-}C_6)$ alkyl group,
$R^2$ represents
(b1) a hydrogen atom;
(b2) a $(C_1\text{-}C_6)$ alkyl group;
(b3) a halo $(C_1\text{-}C_6)$ alkyl group;
(b4) a $(C_3\text{-}C_6)$ cycloalkyl group; or
(b5) a halo $(C_3\text{-}C_6)$ cycloalkyl group,
$R^3$ represents
(c1) a hydrogen atom;
(c2) a $(C_1\text{-}C_6)$ alkyl group;
(c3) a halo $(C_1\text{-}C_6)$ alkyl group;
(c4) a $(C_3\text{-}C_6)$ cycloalkyl group;
(c5) a $(C_3\text{-}C_6)$ cycloalkyl $(C_1\text{-}C_6)$ alkyl group;
(c6) a $(C_1\text{-}C_6)$ alkylthio $(C_1\text{-}C_6)$ alkyl group;
(c7) a $(C_1\text{-}C_6)$ alkylsulfinyl $(C_1\text{-}C_6)$ alkyl group; or
(c8) a $(C_1\text{-}C_6)$ alkylsulfonyl $(C_1\text{-}C_6)$ alkyl group,
$R^4$ represents
(d1) a hydrogen atom;
(d2) a halogen atom;
(d3) a cyano group;
(d4) a $(C_1\text{-}C_6)$ alkyl group;
(d5) a $(C_2\text{-}C_6)$ alkenyl group;
(d6) a $(C_3\text{-}C_6)$ cycloalkyl group;
(d7) a $(C_3\text{-}C_6)$ cycloalkyl $(C_2\text{-}C_6)$ alkynyl group;
(d8) a $(C_1\text{-}C_6)$ alkoxy group;
(d9) a $(C_1\text{-}C_6)$ alkylthio group;

(d10) an $R^6(R^7)N$ group wherein $R^6$ and $R^7$ may be the same or different and each represent a hydrogen atom, a $(C_1-C_6)$ alkyl group, a halo $(C_1-C_6)$ alkyl group, a $(C_1-C_6)$ alkoxycarbonyl group, a $(C_1-C_6)$ alkylcarbonyl group, or a $(C_3-C_6)$ cycloalkylcarbonyl group;
(d11) an $NR^6CON(R^6)R^7$ group wherein $R^6$ and $R^7$ are the same as above;
(d12) an aryl group;
(d13) an aryl group having, on the ring, 1 to 4 substituting groups which may be the same or different and are selected from (a) a halogen atom, (b) a cyano group, (c) a nitro group, (d) a $(C_1-C_6)$ alkyl group, (e) a halo $(C_1-C_6)$ alkyl group, (f) a $(C_1-C_6)$ alkoxy group, (g) a halo $(C_1-C_6)$ alkoxy group, (h) a $(C_1-C_6)$ alkylthio group, (i) a halo $(C_1-C_6)$ alkylthio group, (j) a $(C_1-C_6)$ alkylsulfinyl group, (k) a halo $(C_1-C_6)$ alkylsulfinyl group, (l) a $(C_1-C_6)$ alkylsulfonyl group, and (m) a halo $(C_1-C_6)$ alkylsulfonyl group;
(d14) a heterocyclic group; or
(d15) a heterocyclic group having, on the ring, 1 to 3 substituting groups which may be the same or different and are selected from (a) a halogen atom, (b) a cyano group, (c) a nitro group, (d) a $(C_1-C_6)$ alkyl group, (e) a halo $(C_1-C_6)$ alkyl group, (f) a $(C_1-C_6)$ alkoxy group, (g) a halo $(C_1-C_6)$ alkoxy group, (h) a $(C_1-C_6)$ alkylthio group, (i) a halo $(C_1-C_6)$ alkylthio group, (j) a $(C_1-C_6)$ alkylsulfinyl group, (k) a halo $(C_1-C_6)$ alkylsulfinyl group, (l) a $(C_1-C_6)$ alkylsulfonyl group, and (m) a halo $(C_1-C_6)$ alkylsulfonyl group, and
A represents a nitrogen atom or $C-R^5$ wherein $R^5$ represents (e1) a hydrogen atom, (e2) a $(C_1-C_6)$ alkyl group, or (e3) a halo $(C_1-C_6)$ alkyl group, or a salt thereof.

2. The condensed heterocyclic compound which has a bridgehead nitrogen atom and is bound to a pyridine ring containing an oxime group or the salt thereof according to claim 1, wherein
$R^1$ represents
(a1) a hydrogen atom; or
(a4) a halo $(C_1-C_6)$ alkyl group,
$R^2$ represents
(b1) a hydrogen atom; or
(b2) a $(C_1-C_6)$ alkyl group,
$R^3$ represents
(c2) a $(C_1-C_6)$ alkyl group;
(c3) a halo $(C_1-C_6)$ alkyl group;
(c6) a $(C_1-C_6)$ alkylthio $(C_1-C_6)$ alkyl group;
(c7) a $(C_1-C_6)$ alkylsulfinyl $(C_1-C_6)$ alkyl group; or
(c8) a $(C_1-C_6)$ alkylsulfonyl $(C_1-C_6)$ alkyl group,
$R^4$ represents
(d1) a hydrogen atom;
(d2) a halogen atom;
(d3) a cyano group;
(d4) a $(C_1-C_6)$ alkyl group;
(d5) a $(C_2-C_6)$ alkenyl group;
(d6) a $(C_3-C_6)$ cycloalkyl group;
(d7) a $(C_3-C_6)$ cycloalkyl $(C_2-C_6)$ alkynyl group;
(d8) a $(C_1-C_6)$ alkoxy group;
(d9) a $(C_1-C_6)$ alkylthio group;
(d10) an $R^6(R^7)N$ group wherein $R^6$ and $R^7$ are the same as above;
(d11) an $NR^6CON(R^6)R^7$ group wherein $R^6$ and $R^7$ are the same as above;
(d12) an aryl group;
(d13) an aryl group having, on the ring, 1 to 4 substituting groups which may be the same or different and are selected from (a) a halogen atom, (b) a cyano group, (c) a nitro group, (d) a $(C_1-C_6)$ alkyl group, (e) a halo $(C_1-C_6)$ alkyl group, (f) a $(C_1-C_6)$ alkoxy group, (g) a halo $(C_1-C_6)$ alkoxy group, (h) a $(C_1-C_6)$ alkylthio group, (i) a halo $(C_1-C_6)$ alkylthio group, (j) a $(C_1-C_6)$ alkylsulfinyl group, (k) a halo $(C_1-C_6)$ alkylsulfinyl group, (l) a $(C_1-C_6)$ alkylsulfonyl group, and (m) a halo $(C_1-C_6)$ alkylsulfonyl group;
(d14) a heterocyclic group; or
(d15) a heterocyclic group having, on the ring, 1 to 3 substituting groups which may be the same or different and are selected from (a) a halogen atom, (b) a cyano group, (c) a nitro group, (d) a $(C_1-C_6)$ alkyl group, (e) a halo $(C_1-C_6)$ alkyl group, (f) a $(C_1-C_6)$ alkoxy group, (g) a halo $(C_1-C_6)$ alkoxy group, (h) a $(C_1-C_6)$ alkylthio group, (i) a halo $(C_1-C_6)$ alkylthio group, (j) a $(C_1-C_6)$ alkylsulfinyl group, (k) a halo $(C_1-C_6)$ alkylsulfinyl group, (l) a $(C_1-C_6)$ alkylsulfonyl group, and (m) a halo $(C_1-C_6)$ alkylsulfonyl group, and
A represents a nitrogen atom or $C-R^5$ wherein $R^5$ represents (e1) a hydrogen atom, (e2) a $(C_1-C_6)$ alkyl group, or (e3) a halo $(C_1-C_6)$ alkyl group.

3. The condensed heterocyclic compound which has a bridgehead nitrogen atom and is bound to a pyridine ring containing an oxime group or the salt thereof according to claim 1, wherein
$R^1$ represents
(a1) a hydrogen atom; or
(a4) a halo $(C_1-C_6)$ alkyl group,
$R^2$ represents
(b1) a hydrogen atom; or
(b2) a $(C_1-C_6)$ alkyl group,
$R^3$ represents
(c2) a $(C_1-C_6)$ alkyl group;
(c3) a halo $(C_1-C_6)$ alkyl group;
(c6) a $(C_1-C_6)$ alkylthio $(C_1-C_6)$ alkyl group; or
(c8) a $(C_1-C_6)$ alkylsulfonyl $(C_1-C_6)$ alkyl group,
$R^4$ represents
(d1) a hydrogen atom;
(d2) a halogen atom;
(d6) a $(C_3-C_6)$ cycloalkyl group;
(d8) a $(C_1-C_6)$ alkoxy group;
(d12) an aryl group; or
(d13) an aryl group having, on the ring, 1 to 4 substituting groups which may be the same or different and are selected from (a) a halogen atom, (b) a cyano group, (c) a nitro group, (d) a $(C_1-C_6)$ alkyl group, (e) a halo $(C_1-C_6)$ alkyl group, (f) a $(C_1-C_6)$ alkoxy group, (g) a halo $(C_1-C_6)$ alkoxy group, (h) a $(C_1-C_6)$ alkylthio group, (i) a halo $(C_1-C_6)$ alkylthio group, (j) a $(C_1-C_6)$ alkylsulfinyl group, (k) a halo $(C_1-C_6)$ alkylsulfinyl group, (l) a $(C_1-C_6)$ alkylsulfonyl group, and (m) a halo $(C_1-C_6)$ alkylsulfonyl group, and
A represents a nitrogen atom or $C-R^5$ wherein $R^5$ represents (e1) a hydrogen atom or (e3) a halo $(C_1-C_6)$ alkyl group.

4. An agricultural or horticultural insecticide comprising, as an active ingredient, the condensed heterocyclic compound which has a bridgehead nitrogen atom and is bound to a pyridine ring containing an oxime group or the salt thereof according to claim 1.

5. A method for using an agricultural or horticultural insecticide, comprising treating plants or soil with an effective amount of the condensed heterocyclic compound which has a bridgehead nitrogen atom and is bound to a pyridine ring containing an oxime group or the salt thereof according to claim 1.

6. An animal ectoparasite or endoparasite control agent comprising, as an active ingredient, an effective amount of the condensed heterocyclic compound which has a bridgehead nitrogen atom and is bound to a pyridine ring containing an oxime group or the salt thereof according to claim 1.

7. A method for using an animal ectoparasite or endoparasite control agent, comprising transdermally applying or orally administering, to an animal, an effective amount of the condensed heterocyclic compound which has a bridgehead nitrogen atom and is bound to a pyridine ring containing an oxime group or the salt thereof according to claim 1.

* * * * *